US009540434B2

(12) United States Patent
Pfeifer et al.

(10) Patent No.: US 9,540,434 B2
(45) Date of Patent: Jan. 10, 2017

(54) PHOSPHOSPECIFIC ANTIBODIES RECOGNISING TAU

(71) Applicants: AC IMMUNE S.A., Lausanne (CH); KATHOLIEKE UNIVERSITEIT LEUVEN, Leuven (BE)

(72) Inventors: Andrea Pfeifer, St-Legier (CH); Andreas Muhs, Pully (CH); Maria Pihlgren, Mont-sur-Lausanne (CH); Oskar Adolfsson, Bercher (CH); Fred Van Leuven, Linden (BE)

(73) Assignees: AC IMMUNE S.A., Lausanne (CH); KATHOLIEKE UNIVERSITEIT LEUVEN, Leuven (BE)

( * ) Notice: Subject to any disclaimer, the term of this patent is extended or adjusted under 35 U.S.C. 154(b) by 0 days.

(21) Appl. No.: 14/348,918

(22) PCT Filed: Oct. 5, 2012

(86) PCT No.: PCT/EP2012/069783
§ 371 (c)(1),
(2) Date: Apr. 1, 2014

(87) PCT Pub. No.: WO2013/050567
PCT Pub. Date: Apr. 11, 2013

(65) Prior Publication Data
US 2014/0294731 A1    Oct. 2, 2014

(30) Foreign Application Priority Data

Oct. 7, 2011   (WO) .................. PCT/EP2011/067604
Apr. 5, 2012   (EP) ..................................... 12163319

(51) Int. Cl.
| | |
|---|---|
| *C07K 16/00* | (2006.01) |
| *C12P 21/08* | (2006.01) |
| *A61K 39/395* | (2006.01) |
| *A61K 39/00* | (2006.01) |
| *C07K 16/18* | (2006.01) |
| *G01N 33/68* | (2006.01) |

(52) U.S. Cl.
CPC ........... *C07K 16/18* (2013.01); *A61K 39/0005* (2013.01); *A61K 39/3955* (2013.01); *G01N 33/6896* (2013.01); *A61K 2039/505* (2013.01); *C07K 2317/30* (2013.01); *C07K 2317/34* (2013.01); *C07K 2317/76* (2013.01); *G01N 2800/2821* (2013.01)

(58) Field of Classification Search
CPC . C07K 16/18; C07K 2317/34; C07K 2317/76; C07K 14/4711; C07K 2317/24; C07K 2317/30; C07K 2317/70; C07K 16/46; C07K 2317/565; C07K 2317/622; G01N 33/6896; G01N 2800/2821; G01N 2800/28; G01N 33/6803; G01N 33/53; G01N 2800/52; G01N 33/5058; A61K 2039/505; A61K 39/0005; A61K 39/3955; A61K 39/0007; A61K 39/395; Y10S 435/962; Y10S 435/975; C12N 15/02

See application file for complete search history.

(56) References Cited

U.S. PATENT DOCUMENTS

| | | | |
|---|---|---|---|
| 8,012,936 B2 * | 9/2011 | Sigurdsson et al. | ......... 514/17.8 |
| 8,748,386 B2 * | 6/2014 | Sigurdsson | .................. 514/17.8 |
| 2002/0086009 A1 | 7/2002 | Ishiguro et al. | |
| 2005/0221391 A1 | 10/2005 | Davies | |
| 2008/0050383 A1 | 2/2008 | Sigurdsson et al. | |
| 2008/0220449 A1 | 9/2008 | Vasan et al. | |
| 2011/0318358 A1 | 12/2011 | Sigurdsson et al. | |
| 2012/0276009 A1 | 11/2012 | Pfeifer et al. | |
| 2014/0302046 A1 * | 10/2014 | Sigurdsson | ................ 424/139.1 |

FOREIGN PATENT DOCUMENTS

| | | | | |
|---|---|---|---|---|
| CN | 102070718 | | 5/2011 | |
| EP | 2210901 | | 7/2010 | |
| WO | 93/11231 | | 6/1993 | |
| WO | 96/13590 | | 5/1996 | |
| WO | 96/29605 | | 9/1996 | |
| WO | 98/22120 | | 5/1998 | |
| WO | WO98/22120 | * | 5/1998 | ............. A61K 38/00 |
| WO | 2004/058258 | | 7/2004 | |
| WO | 2008/157302 | | 12/2008 | |
| WO | 2010/106127 | | 9/2010 | |
| WO | 2010/115843 | | 10/2010 | |
| WO | 2010/144711 | | 12/2010 | |
| WO | 2011/013034 | | 2/2011 | |
| WO | 2012/045882 | | 4/2012 | |
| WO | WO2012/0445882 | * | 4/2012 | ............. A61K 39/00 |

(Continued)

OTHER PUBLICATIONS

Rosenmann et al. Neurosci. Lett. 2004; 410; 90-93.*
Bartos et al., J. Neuroimmunol. 2012; 252:100-105.*
Hoffmann et al., Biochemistry, 1997; 36:8114-8124.*
"Instructions for Authors", The Journal of Neuroscience, published [online]Jun. 29, 1998. Retrieved [online] from <web.archive.org/web/19980629153321 /http://www.jneurosci.org/misc/itoa.shtml> on Jan. 7, 2015.
Bhaskar, K. et al., "Tyrosine Phosphorylation of Tau Accompanies Disease Progression inTransgenic Mouse Models of Tauopathy," Neuropathology and Applied Neurobiology, 2010, vol. 36, No. 6, PQS. 462-477.

(Continued)

*Primary Examiner* — Chang-Yu Wang
(74) *Attorney, Agent, or Firm* — McNeill Baur PLLC

(57) ABSTRACT

The present invention relates to methods and compositions for the therapeutic and diagnostic use in the treatment of diseases and disorders which are caused by or associated with neurofibrillary tangles, in particular, the invention relates to antibodies, which specifically recognize and bind to phosphorylated pathological protein tau-conformers and (Continued)

to methods and compositions involving said antibodies for the therapeutic and diagnostic use in the treatment of tauopathies including Alzheimer's Disease (AD).

17 Claims, 17 Drawing Sheets

(56) References Cited

FOREIGN PATENT DOCUMENTS

WO 2013/050567 4/2013
WO 2013/166302 11/2013

OTHER PUBLICATIONS d'Abramo et al., PLOSone, 8(4): e62402, published Apr. 29, 2013.
Hirata-Fukae, C. et al., "Levels of Soluble and Insoluble Tau Reflect Overall Status of TauPhosphorylation in Vivo," Neuroscience Letters, Jan. 23, 2009, vol. 450, No. 1, pp. 51-55.
Hoffman, R. et al., "Unique Alzheimer's Disease Paired Helical Filament Specific EpitopesInvolve Double Phosphorylation at Specific Sites," Biochemistry, Jul. 1, 1997, vol. 36, No. 26. pp. 8114-8124.
International Preliminary Report on Patentability date of issuance of Apr. 9, 2013 for application PCT/EP2011/067604.
International Preliminary Report on Patentability date of issuance of Oct. 7, 2014 for application PCT/US2013/032341.
International Preliminary Report on Patentability date of mailing of Apr. 17, 2014, for application PCT/EP2012/069783.
International Search Report and Written Opinion date of mailing of Sep. 3, 2013, for application PCT/US2013/032341.
International Search Report and Written Opinion dated Apr. 11, 2013 for application PCT/EP2012/069783.
International Search Report and Written Opinion dated Apr. 3, 2012 in InternationalApplication No. PCT/EP2011/067604.
Jicha, "Camp-Dependent Protein Kinase Phosphorylations on Tau in Alzheimer's Disease," Journal of Neuroscience, Jan. 1, 1999, vol. 19, No. 17, p. 7486.
Lee, G. et al., "Phosphorylation of Tau by Fyn: Implications for Alzheimer's Disease," Journal ofNeuroscience, Mar. 3, 2004, vol. 24, No. 9, pp. 2304-2312.
Lichtenberg-Kraag, B. et al., "Phosphorylation-Dependent Epitopes of NeurofilamentAntibodies on Tau Protein and Relationship with Alzheimer Tau," Proceedings of the NationalAcademy of Sciences of USA, Jun. 1, 1992, vol. 89, No. 12, pp. 5384-5388.
Oddo, S. et al., "Reduction of Soluble Abeta and Tau, but not Soluble Abeta Alone, AmelioratesCognitive Decline in Transgenic Mice with Plaques and Tangles," Journal of Biological Chemistry,Jan. 1, 2006, vol. 281, No. 51, pp. 39413-39423.
Otvos, L. et al., "Monoclonal Antibody PHF4 Recognizes Tau Protein Phosphorylated at SerineResidues 396 and 404," Journal of Neuroscience Research, Jan. 1, 1994, vol. 39, pp. 669-673.
File History for U.S. Appl. No. 13/500,608.
Roder, H. et al., "Phosphorylation-Dependent Monoclonal Tau Antibodies no not Reliably ReportPhosphorylation by Extracellular Signal-Regulated Kinase 2 at Specific Sites," Journal of BiologicalChemistry, Feb. 14, 1997, vol. 272, No. 7, pp. 4509-4515.
Singer, D. et al., "Characterization of Phosphorylation Dependent Antibodies to Study thePhosphorylation Dependent Antibodies to Study the Phosphorylation Status of the Tau Protein," International Journal of Peptide Research and Therapeutics (formerly known as Letters in PepdtideScience), Dec. 1, 2005. vol. 11, No. 4, pp. 279-289.
Singer, D. et al., "Immuno-PCR-Based Quantification of Multiple Phosphorylated Tau-EpitopesLinked to Alzheimer's Disease," Analytical and Bioanalytical Chemistry, vol. 395, No. 7, Oct. 11, 2009, pp. 2263-2267.
Torreilles, F. et al., "Binding Specificty of Monoclonal Antibody AD2: Influence of thePhosphorylation State of Tau," Molecular Brain Research, Jan. 1, 2000, vol. 78, pp. 181-185.
Vanderbroek. T., et al., "Identification and isolation of a hyperphosphorylated, conformationally changed intermediate of human protein tau expressed in yeast", Biochemistry, 2005, vol. 44, pp. 11466-11475.
Vanhelmont, T. et al., "Serine-409 Phosphorylation and Oxidative Damage Define Aggregationof Human Protein Tau in Yeast," Fems Yeast Research, Dec. 1, 2010, vol. 10, No. 8, pp. 992-1005.
Zemlan, F. et al., "Monoclonal Antibody PHF-9 Recognizes Phosphorylated Serine 404 of TauProtein and Labels Paired Helical Filaments," Journal of Neuroscience Research, Oct. 1, 1996,vol. 46, No. 1, pp. 90-97.
Zheng-Fischhoefer, Q. et al., "Sequential Phosphorylation of Tau by Glycogen SynthaseKinase-3beta and Protein Kinase A at Thr212 and Ser214 Generates the Alzheimer-SpecificEpitope of Antibody A T100 and Requires a Paired-Helical-Filament-Like Conformation," EuropeanJournal of Biochemistry, Mar. 1, 1998, vol. 252, No. 3, pp. 542-552.
Rankin et al., "Tau Phosphorylation by GSK-3beta Promotes Tangle-Like Filament Morphology," Mol. Neurodegener, 2007, 2:12.
English translation of Search Report for Chinese Patent Application No. 201280080349.3, dated Jul. 20, 2015 (2 pages).
Boutajangout et al., "Passive immunization targeting pathological phosphho-tau protein in a mouse model reduces functional decline and clears tau aggregates from the brain," J. Neurochem., 118: 658-667 (2011).
Sahara et al., "Phosphorylated p38MAPK specific antibodies cross-react with sarkosyl-insoluble hyperphosphorylated tau proteins," J. Neurochem., 90: 829-838 (2009).

* cited by examiner

PHOSPHOSPECIFIC ANTIBODIES RECOGNISING TAU

This application claims the benefit of European Patent Application No. EP12163319.2 filed on Apr. 5, 2012 and International Patent Application No. PCT/EP2011/067604 filed on Oct. 7, 2011, the contents of each of which is hereby incorporated by reference it its entirety.

The present invention is related to methods and compositions for the therapeutic and diagnostic use in the treatment of diseases and disorders which are caused by or associated with neurofibrillary tangles. In particular, the invention relates to antibodies, which specifically recognize and bind to phosphorylated pathological protein tau-conformers and to methods and compositions involving said antibodies for the therapeutic and diagnostic use in the treatment of tauopathies including Alzheimer's Disease (AD).

Neurofibrillary tangles and neuropil threads (NTs) are the major neuropathological hallmarks of Alzheimer's Disease (AD). They are composed of the microtubule-associated protein tau that has undergone posttranslational modifications, including phosphorylation, deamidation and isomerization on asparaginyl or aspartyl residues. They originate by the aggregation of hyper-phosphorylated protein tau and its conformers. AD shares this pathology with many neurodegenerative tauopathies, in particularly with specified types of frontotemporal dementia (FTD).

Protein Tau is a freely soluble, "naturally unfolded" protein that binds avidly to microtubules (MTs) to promote their assembly and stability. MTs are of major importance for the cytoskeletal integrity of neurons—and thereby for the proper formation and functioning of neuronal circuits, hence for learning and memory. The binding of tau to MT is controlled by dynamic phosphorylation and de-phosphorylation, as demonstrated mainly in vitro and in non-neuronal cells. Due to the large number of possible phosphorylation sites (>80), the exact contribution of each and the identity of the responsible kinases remain largely undefined in vivo.

In AD brain, tau pathology develops later than, and therefore probably in response to amyloid pathology, which constitutes the essence of the amyloid cascade hypothesis. This is based on and indicated by studies in AD and Down syndrome patients, and is corroborated by studies in transgenic mice with combined amyloid and tau pathology (Lewis et al., 2001; Oddo et al., 2004; Ribe et al., 2005; Muyllaert et al, 2006; 2008; Terwel et al, 2008).

The exact timing of both pathologies in human AD patients as well as mechanisms that link amyloid to tau pathology remain largely unknown, but are proposed to involve activation of neuronal signaling pathways that act on or by GSK3 and cdk5 as the major "tau-kinases" (reviewed by Muyllaert et al, 2006, 2008).

The hypothesis that tauopathy is not an innocent side-effect but a major pathological executor in AD is based on sound genetic, pathological and experimental observations that corroborate each other fully:

in early-onset familial AD cases that are due to mutations in amyloid protein precursor (APP) or presenilin, the obligate pathogenic cause is amyloid accumulation, but invariably the pathology comprises collateral tauopathy, identical to that in the late-onset sporadic AD cases;
  severity of cognitive dysfunction and dementia correlates with tauopathy, not with amyloid pathology, exemplified most recently by several clinical phase-1&2 studies that include PIB-PET imaging for amyloid and identify many "false positives": cognitively normal individuals with high brain amyloid load;
  in familial FTD, the tauopathy is provoked by mutant tau and causes neurodegeneration directly, without amyloid pathology;
  in experimental mouse models the cognitive defects caused by amyloid pathology are nearly completely alleviated by the absence of protein tau (Roberson et al, 2007).

The combined arguments support the hypothesis that protein tau is a major player in the cognitive demise in AD and related neurodegenerative tauopathies.

A prominent emerging treatment of AD is by passive immunotherapy with specific mAbs, to clear amyloid peptides and their aggregates that are presumed to be neurotoxic or synapto-toxic.

Immunotherapy targeting tau pathology, as proposed here, is anticipated to counteract the pathological protein tau-conformers that are known or postulated to cause synaptic dysfunction and neurodegeneration.

Other therapeutic approaches that target protein tau are scarce and comprise mainly:
  inhibitors of the kinases that are thought to increase the phosphorylation of tau to pathological levels
  compounds that block the cytoplasmic aggregation of hyper-phosphorylated protein tau.

These approaches suffer various draw-backs of specificity and efficacy, a problem they share with attempts to modify the metabolism of APP and amyloid, all emphasizing the importance of a continuous search for additional treatment options, including immunotherapy against tau. Indeed, immunotherapy targeting amyloid in a preclinical mouse model with combined AD-like pathology demonstrated also an effect on tau pathology although tau aggregates persisted (Oddo et al., 2004).

Some doubts have been cast on the feasibility of approaching intra-cellular protein tau by immunotherapy. These have been countered by the most recent experimental study in a tauopathy mouse model (Asuni et al., 2007). They showed reduction in tangle pathology and functional improvements by vaccination with a protein tau derived phospho-peptide. These data corroborate previous reports of immunotherapy targeting α-synuclein in Parkinson's Disease (PD) and Lewy body disease models (Masliah et al., 2005, 2011) and of superoxide dismutase in an amyotrophic lateral sclerosis (ALS) model (Urushitiani et al., 2007). These diseases are examples wherein intra-cellular proteins lead to synaptic defects and neurodegeneration by as yet not fully understood mechanisms.

There is an unmet need for passive and/or active immunotherapies that work to counteract the pathological protein conformers that are known—or presumed—to cause neurodegenerative disorders, such as amyloid pathology in AD caused, for example, by intra-neuronal aggregates of hyper-phosphorylated protein tau that are as typical for AD as amyloid.

This unmet need is met by the present invention which provides for binding proteins recognizing and binding to major pathological phospho-epitopes of the tau protein. In particular, the present invention provides specific antibodies against linear and conformational, simple and complex phospho-epitopes on protein tau, particularly on aggregated tau protein that are believed to be responsible for synapto- and neuro-toxicity in tauopathies, including AD.

Accordingly, the present invention relates in one embodiment to a binding peptide or protein or a functional part thereof, particularly to an antibody, particularly to a monoclonal antibody or a functional part thereof, which binding peptide or protein or antibody recognizes and specifically binds to a phospho-epitope on a mammalian, particularly on the human Tau protein or on a fragment thereof, particularly to a phospho-epitope on aggregated Tau protein, particularly to a pathological protein tau conformer, but, in one embodiment, does not bind to the corresponding unphosphorylated epitope and/or to non-related epitopes, wherein said binding peptide or antibody has a high binding affinity to soluble, oligomeric and insoluble phosphorylated Tau protein and is capable of detecting and/or modulating levels of soluble, oligomeric and insoluble phosphorylated Tau protein in vivo, particularly in the brain, particularly with a dissociation constant of at least 10 nM, particularly of at least 8 nM, particularly of at least 5 nM, particularly of at least 2 nM, particularly of at least 1 nM, particularly of at least 500 pM, particularly of at least 400 pM, particularly of at least 300 pM, particularly of at least 200 pM, particularly of at least 100 pM, particularly of at least 50 pM.

In particular, the dissociation constant is in a range of between 2 nM and 80 nM, particularly between 2 nM and 40 nM, particularly between 2 nM and 10 nM.

In a certain aspect, provided herein is an antibody or a functional fragment thereof, wherein said antibody or antibody fragment binds to a phospho-epitope having, or within, the amino acid sequence VYKSPVVSGDTSPRHL (SEQ ID NO: 62) (Tau aa 393-408 of SEQ ID NO: 67, e.g., as set forth in Table 1) comprising a phosphorylated Ser at position 396 (pS396) and at position 404 (pS404).

In a second embodiment, the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes, wherein said binding peptide or antibody has a high binding affinity to soluble, oligomeric and insoluble phosphorylated Tau protein and is capable of detecting and/or modulating levels of soluble, oligomeric and insoluble phosphorylated Tau protein in vivo and has an association rate constant of $10^4$ $M^{-1}$ $s^{-1}$ or greater, particularly of between 3-5×$10^4$ $M^{-1}$ $s^{-1}$ or greater, particularly of $10^5$ $M^{-1}$ $s^{-1}$ or greater; particularly of 2-9×$10^5$ $M^{-1}$ $s^{-1}$ or greater; particularly of $10^6$ $M^{-1}$ $s^{-1}$ or greater, particularly of 1-4×$10^6$ $M^{-1}$ $s^{-1}$ or greater, particularly of $10^7$ $M^{-1}$ $s^{-1}$ or greater.

In particular, the association rate constant is in a range of between 1.6×$10^3$ and 5×$10^5$, particularly between 2.4×$10^4$ and 5×$10^5$, between 3×$10^3$ and 5×$10^5$.

In a third embodiment, the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes, wherein said binding peptide or antibody has a high binding affinity to soluble, oligomeric and insoluble phosphorylated Tau protein and is capable of detecting and/or modulating levels of soluble, oligomeric and insoluble phosphorylated Tau protein in vivo and has a high binding affinity with a dissociation constant of at least 4 nM and an association rate constant of $10^5$ $M^{-1}$ $s^{-1}$ or greater, particularly a dissociation constant of at least 3 nM and an association rate constant of $10^6$ $M^{-1}$ $s^{-1}$ or greater, particularly a dissociation constant of at least 2 nM and an association rate constant of $10^4$ $M^{-1}$ $s^{-1}$ or greater, particularly a dissociation constant of at least 1 nM and an association rate constant of $10^5$ $M^{-1}$ $s^{-1}$ or greater, particularly a dissociation constant of at least 200 pM and an association rate constant of $10^5$ $M^{-1}$ $s^{-1}$ or greater, particularly a dissociation constant of at least 100 pM and an association rate constant of $10^6$ $M^{-1}$ $s^-$ or greater.

In particular, the dissociation constant is in a range of between 2 nM and 80 nM and the association rate constant is in a range of between 1.6×$10^3$ and 5×$10^5$, particularly the dissociation constant is in a range of between 2 nM and 40 nM and the association rate constant is in a range of between 2.4×$10^4$ and 5×$10^5$, particularly the dissociation constant is in a range of between 2 nM and 10 nM and the association rate constant is in a range of between 3×$10^3$ and 5×$10^5$.

One embodiment (4) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes, wherein said binding peptide or antibody has a high binding affinity to soluble, oligomeric and insoluble phosphorylated Tau protein and is capable of detecting and/or modulating levels of soluble, oligomeric and insoluble phosphorylated Tau protein in vivo and wherein said binding peptide or antibody binds to an epitope on a mammalian, particularly on the human Tau protein as shown in SEQ ID NO: 67, selected from the group consisting of Tau aa 393-401, comprising a phosphorylated Ser at position 396 (pS396), Tau aa 396-401 comprising a phosphorylated Ser at position 396 (pS396), Tau aa 394-400 comprising a phosphorylated Ser at position 396 (pS396), Tau aa 402-406 comprising a phosphorylated Ser at position 404 (pS404) and Tau aa 393-400 comprising a phosphorylated Ser at position 396 (pS396).

One embodiment (5) relates to the binding peptide or antibody of any of the preceding embodiments, wherein said peptide binds to an epitope on a mammalian, particularly on the human Tau protein, but especially the human Tau protein as shown in SEQ ID NO: 67, comprising Tau aa 393-401 comprising a phosphorylated Ser at position 396 (pS396).

One embodiment (6) relates to the binding peptide or antibody of any of the preceding embodiments, wherein said peptide binds to an epitope on a mammalian, particularly on the human Tau protein, but especially the human Tau protein as shown in SEQ ID NO: 67, comprising Tau aa 396-401 comprising a phosphorylated Ser at position 396 (pS396).

One embodiment (7) relates to the binding peptide or antibody of any of the preceding embodiments, wherein said peptide binds to an epitope on a mammalian, particularly on the human Tau protein, but especially the human Tau protein as shown in SEQ ID NO: 67, comprising Tau aa 394-400 comprising a phosphorylated Ser at position 396 (pS396).

One embodiment (8) relates to the binding peptide or antibody of any of the preceding embodiments, wherein said peptide binds to an epitope on a mammalian, particularly on the human Tau protein, but especially the human Tau protein as shown in SEQ ID NO: 67, comprising Tau aa 402-406 comprising a phosphorylated Ser at position 404 (pS404).

One embodiment (9) relates to the binding peptide or antibody of any of the preceding embodiments, wherein said peptide binds to an epitope on a mammalian, particularly on the human Tau protein, but especially the human Tau protein as shown in SEQ ID NO: 67, comprising Tau aa 393-400 comprising a phosphorylated Ser at position 396 (pS396).

One embodiment (10) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody has a high binding affinity to soluble, oligomeric and insoluble phosphorylated Tau protein and is capable of detecting and/or modulating levels of soluble, oligomeric and insoluble phosphorylated Tau protein in vivo and wherein said binding peptide or antibody comprises a first binding domain comprising in sequence a CDR1 with the amino acid sequence shown in SEQ ID NO: 73, a CDR2 with the amino acid sequence shown in SEQ ID NO: 74, and a CDR3 with the amino acid sequence shown in SEQ ID NO: 75, or an amino acid sequence at least at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto and/or a second binding domain comprising in sequence a CDR1 with the amino acid sequence shown in SEQ ID NO: 70, or an amino acid sequence at least 95%, particularly 98%, particularly 99% identical thereto, a CDR2 with the amino acid sequence shown in SEQ ID NO: 71, or an amino acid sequence at least 94%, 95%, 96%, 97%, 98%, or 99% identical thereto, and a CDR3 with the amino acid sequence shown in SEQ ID NO: 72, or an amino acid sequence at least at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto.

In one aspect, provided herein is an antibody or a functional fragment thereof, which antibody or fragment thereof recognizes and specifically binds to a phospho-epitope on a mammalian Tau protein or on a fragment thereof, wherein said antibody or fragment thereof comprises:
(a) a first binding domain comprising a CDR1 comprising the amino acid sequence shown in SEQ ID NO: 73, a CDR2 comprising the amino acid sequence shown in SEQ ID NO: 74, and a CDR3 comprising the amino acid sequence shown in SEQ ID NO: 75; and/or
(b) a second binding domain comprising an amino acid sequence comprising a CDR1 comprising the amino acid sequence shown in SEQ ID NO: 70, a CDR2 comprising the amino acid sequence shown in SEQ ID NO: 71, and a CDR3 comprising the amino acid sequence shown in SEQ ID NO: 72.

One embodiment (11) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody has a high binding affinity to soluble, oligomeric and insoluble phosphorylated Tau protein and is capable of detecting and/or modulating levels of soluble, oligomeric and insoluble phosphorylated Tau protein in vivo and wherein said binding peptide or antibody comprises a first binding domain comprising in sequence a CDR1 with the amino acid sequence shown in SEQ ID NO: 81, a CDR2 with the amino acid sequence shown in SEQ ID NO: 82, and a CDR3 with the amino acid sequence shown in SEQ ID NO: 83, or an amino acid sequence at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto and/or a second binding domain comprising in sequence a CDR1 with the amino acid sequence shown in SEQ ID NO: 78, a CDR2 with the amino acid sequence shown in SEQ ID NO: 79, and a CDR3 with the amino acid sequence shown in SEQ ID NO: 80, or an amino acid sequence at least at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto.

In one aspect, provided herein is an antibody or a functional fragment thereof, which antibody or fragment thereof recognizes and specifically binds to a phospho-epitope on a mammalian Tau protein or on a fragment thereof, wherein said antibody or fragment thereof comprises:
(a) a first binding domain comprising a CDR1 comprising the amino acid sequence shown in SEQ ID NO: 81, a CDR2 comprising the amino acid sequence shown in SEQ ID NO: 82, and a CDR3 comprising the amino acid sequence shown in SEQ ID NO: 83; and/or
(b) a second binding domain comprising an amino acid sequence comprising a CDR1 comprising the amino acid sequence shown in SEQ ID NO: 78, a CDR2 comprising the amino acid sequence shown in SEQ ID NO: 79, and a CDR3 comprising the amino acid sequence shown in SEQ ID NO: 80.

One embodiment (12) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody has a high binding affinity to soluble, oligomeric and insoluble phosphorylated Tau protein and is capable of detecting and/or modulating levels of soluble, oligomeric and insoluble phosphorylated Tau protein in vivo and wherein said binding peptide or antibody comprises a first binding domain comprising in sequence a CDR1 with the amino acid sequence shown in SEQ ID NO: 93, a CDR2 with the amino acid sequence shown in SEQ ID NO: 94, and a CDR3 with the amino acid sequence shown in SEQ ID NO: 95, or an amino acid sequence at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical to any one of the above CDRs and/or a second binding domain comprising in sequence a CDR1 with the amino acid sequence shown in SEQ ID NO: 89, a CDR2 with the amino acid sequence shown in SEQ ID NO: 90, and a CDR3 with the amino acid sequence shown in SEQ ID NO: 91, or an amino acid sequence at least at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical to any one of the above CDRs.

In a certain aspect, provided herein is an antibody or a functional part thereof, which antibody or fragment thereof recognizes and specifically binds to a phospho-epitope on a mammalian Tau protein or on a fragment thereof, wherein said antibody or fragment thereof comprises:
  (a) a first binding domain comprising a CDR1 comprising the amino acid sequence shown in SEQ ID NO: 93, a CDR2 comprising the amino acid sequence shown in SEQ ID NO: 94, and a CDR3 comprising the amino acid sequence shown in SEQ ID NO: 95; and/or
  (b) a second binding domain comprising an amino acid sequence comprising a CDR1 comprising the amino acid sequence shown in SEQ ID NO: 89, a CDR2 comprising the amino acid sequence shown in SEQ ID NO: 90, and a CDR3 comprising the amino acid sequence shown in SEQ ID NO: 91.

One embodiment (13) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody has a high binding affinity to soluble, oligomeric and insoluble phosphorylated Tau protein and is capable of detecting and/or modulating levels of soluble, oligomeric and insoluble phosphorylated Tau protein in vivo and wherein said binding peptide or antibody comprises a first binding domain comprising in sequence a CDR1 with the amino acid sequence shown in SEQ ID NO: 101, a CDR2 with the amino acid sequence shown in SEQ ID NO: 102, and a CDR3 with the amino acid sequence shown in SEQ ID NO: 103, or an amino acid sequence at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical to any one of the above CDRs and/or a second binding domain comprising in sequence a CDR1 with the amino acid sequence shown in SEQ ID NO: 98, a CDR2 with the amino acid sequence shown in SEQ ID NO: 99, and a CDR3 with the amino acid sequence shown in SEQ ID NO: 100, or an amino acid sequence at least at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical to any one of the above CDRs.

In one aspect, provided herein is an antibody or a functional fragment thereof, which antibody or fragment thereof recognizes and specifically binds to a phospho-epitope on a mammalian Tau protein or on a fragment thereof, wherein said antibody or fragment thereof comprises:
  (a) a first binding domain comprising a CDR1 comprising the amino acid sequence shown in SEQ ID NO: 101, a CDR2 comprising the amino acid sequence shown in SEQ ID NO: 102, and a CDR3 comprising the amino acid sequence shown in SEQ ID NO: 103; and/or
  (b) a second binding domain comprising an amino acid sequence comprising a CDR1 comprising the amino acid sequence shown in SEQ ID NO: 98, a CDR2 comprising the amino acid sequence shown in SEQ ID NO: 99, and a CDR3 comprising the amino acid sequence shown in SEQ ID NO: 100.

One embodiment (14) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody has a high binding affinity to soluble, oligomeric and insoluble phosphorylated Tau protein and is capable of detecting and/or modulating levels of soluble, oligomeric and insoluble phosphorylated Tau protein in vivo and wherein said binding peptide or antibody comprises a first binding domain comprising in sequence a CDR1 with the amino acid sequence shown in SEQ ID NO: 106, a CDR2 with the amino acid sequence shown in SEQ ID NO: 107, and a CDR3 with the amino acid sequence shown in SEQ ID NO: 108, or an amino acid sequence at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical to any one of the above CDRs and/or a second binding domain comprising in sequence a CDR1 with the amino acid sequence shown in SEQ ID NO: 89, a CDR2 with the amino acid sequence shown in SEQ ID NO: 115, and a CDR3 with the amino acid sequence shown in SEQ ID NO: 91, or an amino acid sequence at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical to any one of the above CDRs.

In a particular aspect, provided herein is an antibody or a functional fragment thereof, which antibody or fragment thereof recognizes and specifically binds to a phospho-epitope on a mammalian Tau protein or on a fragment thereof, wherein said antibody or fragment thereof comprises:
(a) a first binding domain comprising a CDR1 comprising the amino acid sequence shown in SEQ ID NO: 106, a CDR2 comprising the amino acid sequence shown in SEQ ID NO: 107, and a CDR3 comprising the amino acid sequence shown in SEQ ID NO: 108; and/or
(b) a second binding domain comprising an amino acid sequence comprising a CDR1 comprising the amino acid sequence shown in SEQ ID NO: 89, a CDR2 comprising the amino acid sequence shown in SEQ ID NO: 115, and a CDR3 comprising the amino acid sequence shown in SEQ ID NO: 91.

In a certain embodiment, the first binding domain of an antibody or antibody fragment thereof described herein is a light chain variable region, and the second binding domain of an antibody or antibody fragment thereof described herein is a heavy chain variable region.

In another embodiment (15), the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes, wherein said binding peptide or antibody has a high binding affinity to soluble, oligomeric and insoluble phosphorylated Tau protein and is capable of detecting and/or modulating levels of soluble, oligomeric and insoluble phosphorylated Tau protein in vivo and wherein said binding peptide or antibody comprises a first binding domain comprising the amino acid sequence shown in SEQ ID NO: 69, 77, 116/92, 118, 97, 105, or an amino acid sequence particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto, and/or a second binding domain comprising the amino acid sequence shown in SEQ ID NO: 68, 76, 88, 96, 104, or an amino acid sequence at least 80%, particularly at least 85%, particularly at least 86%, particularly at least 87%, particularly at least 88%, particularly at least 89%, particularly at least 90%, at least 91%, at least 92%, at least 93%, at least 94%, particularly at least 95%, particularly at least 96%, particularly at least 97%, particularly at least 98%, particularly at least 99% or 100% identical thereto.

One embodiment (16) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody has a high binding affinity to soluble, oligomeric and insoluble phosphorylated Tau protein and is capable of detecting and/or modulating levels of soluble, oligomeric and insoluble phosphorylated Tau protein in vivo and wherein said binding peptide or antibody comprises a first binding domain comprising the amino acid sequence shown in SEQ ID NO: 69, or an amino acid sequence at least 98% or 99% identical thereto; and/or a second binding domain comprising the amino acid sequence shown in SEQ ID NO: 68, or an amino acid sequence at least 90%, 91%, 92% or 93% identical thereto.

One embodiment (17) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody has a high binding affinity to soluble, oligomeric and insoluble phosphorylated Tau protein and is capable of detecting and/or modulating levels of soluble, oligomeric and insoluble phosphorylated Tau protein in vivo and wherein said binding peptide or antibody comprises a first binding domain comprising the amino acid sequence shown in SEQ ID NO: 77, or an amino acid sequence at least 93%, 94% or 95% identical thereto; and/or a second binding domain comprising the amino acid sequence shown in SEQ ID NO: 76, or an amino acid sequence at least 88%, 89%, or 90% identical thereto.

One embodiment (18) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody has a high binding affinity to soluble, oligomeric and insoluble phosphorylated Tau protein and is capable of detecting and/or modulating levels of soluble, oligomeric and insoluble phosphorylated Tau protein in vivo and wherein said binding peptide or antibody comprises a first binding domain comprising the amino acid sequence shown in SEQ ID NO: 116, 92, or 118, or an amino acid sequence at least 93%, 94% or 95% identical thereto; and/or a second binding domain comprising the amino acid sequence shown in SEQ ID NO: 88, or an amino acid sequence at least 90%, 91%, 92% or 93% identical thereto.

One embodiment (19) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody has a high binding affinity to soluble, oligomeric and insoluble phosphorylated Tau protein and is capable of detecting and/or modulating levels of soluble, oligomeric and insoluble phosphorylated Tau protein in vivo and wherein said binding peptide or antibody comprises a first binding domain comprising the amino acid sequence shown in SEQ ID NO: 97, or an amino acid sequence at least 99% identical thereto; and/or a second binding domain comprising the amino acid sequence shown in SEQ ID NO: 96, or an amino acid sequence at least 86%, 87%, 88% or 90% identical thereto.

One embodiment (20) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody has a high binding affinity to soluble, oligomeric and insoluble phosphorylated Tau protein and is capable of detecting and/or modulating levels of soluble, oligomeric and insoluble phosphorylated Tau protein in vivo and wherein said binding peptide or antibody comprises a first binding domain comprising the amino acid sequence shown in SEQ ID NO: 105, or an amino acid sequence at least 98%, or 99% identical thereto; and/or a second binding domain comprising the amino acid sequence shown in SEQ ID NO: 104, or an amino acid sequence at least 88%, 89%, or 90% identical thereto.

One embodiment (21) of the present invention relates to a binding peptide or protein or a functional part thereof, particularly to an antibody, particularly a monoclonal antibody or a functional part thereof, particularly a binding peptide or antibody of any of the preceding embodiments, wherein said binding peptide or antibody comprises a first binding domain the amino acid sequence shown in SEQ ID NO: 69, or an amino acid sequence at least 99% identical thereto; and/or a second binding domain comprising the amino acid sequence shown in SEQ ID NO: 68, or an amino acid sequence at least 93% identical thereto.

One embodiment (22) of the present invention relates to a binding peptide or protein or a functional part thereof, particularly to an antibody, particularly a monoclonal antibody or a functional part thereof, particularly a binding peptide or antibody of any of the preceding embodiments, wherein said binding peptide or antibody comprises a first binding domain comprising the amino acid sequence shown in SEQ ID NO: 77, or an amino acid sequence at least 95% identical thereto and/or a second binding domain comprising the amino acid sequence shown in SEQ ID NO: 76, or an amino acid sequence at least 90% identical thereto.

One embodiment (23) of the present invention relates to a binding peptide or protein or a functional part thereof, particularly to an antibody, particularly a monoclonal antibody or a functional part thereof, particularly a binding peptide or antibody of any of the preceding embodiments, wherein said binding peptide or antibody comprises a first binding domain comprising the amino acid sequence shown in SEQ ID NO: 116, 92, or 118, or an amino acid sequence at least 93 95% identical thereto; and/or a second binding domain comprising the amino acid sequence shown in SEQ ID NO: 88, or an amino acid sequence at least 93% identical thereto.

One embodiment (24) of the present invention relates to a binding peptide or protein or a functional part thereof, particularly to an antibody, particularly a monoclonal antibody or a functional part thereof, particularly a binding peptide or antibody of any of the preceding embodiments, wherein said binding peptide or antibody comprises a first binding domain comprising the amino acid sequence shown in SEQ ID NO: 97, or an amino acid sequence at least 99% identical thereto; and/or a second binding domain comprising the amino acid sequence shown in SEQ ID NO: 96, or an amino acid sequence at least 90% identical thereto.

One embodiment (25) of the present invention relates to a binding peptide or protein or a functional part thereof, particularly to an antibody, particularly a monoclonal antibody or a functional part thereof, particularly a binding peptide or antibody of any of the preceding embodiments, wherein said binding peptide or antibody comprises a first binding domain comprising the amino acid sequence shown in SEQ ID NO: 105, or an amino acid sequence at least 98%, or 99% identical thereto; and/or a second binding domain comprising the amino acid sequence shown in SEQ ID NO: 104, or an amino acid sequence at least 90% identical thereto.

One embodiment (26) of the present invention relates to a binding peptide or protein or a functional part thereof, particularly to an antibody, particularly a monoclonal antibody or a functional part thereof, according to embodiment (16), wherein said first binding domain contains the CDRs as shown in SEQ ID NOs: 73-75, and said second binding domain contains the CDRs as shown in SEQ ID NOs: 70-72.

One embodiment (27) of the present invention relates to a binding peptide or protein or a functional part thereof, particularly to an antibody, particularly a monoclonal antibody or a functional part thereof, according to embodiment (17), wherein said first binding domain contains the CDRs as shown in SEQ ID NOs: 81-83, and said second binding domain contains the CDRs as shown in SEQ ID NOs: 78-80.

One embodiment (28) of the present invention relates to a binding peptide or protein or a functional part thereof, particularly to an antibody, particularly a monoclonal antibody or a functional part thereof, according to embodiment (18), wherein said first binding domain contains the CDRs as shown in SEQ ID NOs: 93-95, and said second binding domain contains the CDRs as shown in SEQ ID NOs: 89-91.

One embodiment (29) of the present invention relates to a binding peptide or protein or a functional part thereof, particularly to an antibody, particularly a monoclonal antibody or a functional part thereof, according to embodiment (19), wherein said first binding domain contains the CDRs as shown in SEQ ID NOs: 101-103, and said second binding domain contains the CDRs as shown in SEQ ID NOs: 98-100.

One embodiment (30) of the present invention relates to a binding peptide or protein or a functional part thereof, particularly to an antibody, particularly a monoclonal antibody or a functional part thereof, according to embodiment (18), wherein said first binding domain contains the CDRs as shown in SEQ ID NOs: 89, 115, and 91, and said second binding domain contains the CDRs as shown in SEQ ID NOs: 106-108.

In still another embodiment (31), the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody has a high binding affinity to soluble, oligomeric and insoluble phosphorylated Tau protein and is capable of detecting and/or modulating levels of soluble, oligomeric and insoluble phosphorylated Tau protein in vivo and wherein said binding peptide or antibody comprises a
- a. first binding domain comprising the amino acid sequence shown in SEQ ID NO: 69 and/or a second binding domain comprising the amino acid sequence shown in SEQ ID NO: 68; or a
- b. first binding domain comprising the amino acid sequence shown in SEQ ID NO: 77 and/or a second binding domain comprising the amino acid sequence shown in SEQ ID NO: 76; or a
- c. first binding domain comprising the amino acid sequence shown in SEQ ID NO: 116 and/or a second binding domain comprising the amino acid sequence shown in SEQ ID NO: 88; or a;
- d. first binding domain comprising the amino acid sequence shown in SEQ ID NO: 92 and/or a second binding domain comprising the amino acid sequence shown in SEQ ID NO: 88; or a
- e. first binding domain comprising the amino acid sequence shown in SEQ ID NO: 97 and/or a second binding domain comprising the amino acid sequence shown in SEQ ID NO: 96; or a
- f. first binding domain comprising the amino acid sequence shown in SEQ ID NO: 105 and/or a second binding domain comprising the amino acid sequence shown in SEQ ID NO: 104.
- g. first binding domain comprising the amino acid sequence shown in SEQ ID NO: 118 and/or a second binding domain comprising the amino acid sequence shown in SEQ ID NO: 88

In one embodiment (32) of the invention, the binding peptide of any of the preceding embodiments is an antibody, particularly an antibody of the IgG2a, IgG2b or the IgG3 isotype, particularly a polyclonal antibody, a monoclonal antibody, a chimeric antibody, a humanized antibody or a fully human antibody.

One embodiment (33) of the invention relates to a polynucleotide encoding the binding peptide of any one of the preceding embodiments.

In one embodiment (34), said polynucleotide comprises a nucleic acid molecule selected from the group consisting of
- a. a nucleic acid molecule comprising a nucleotide sequence encoding a polypeptide comprising the amino acid sequence as depicted in SEQ ID NOs: 84-87, SEQ ID NO: 109-114, 117 and 119;
- b. a nucleic acid molecule comprising a nucleotide sequence that has at least 85% sequence identity to the sequence shown in SEQ ID NOs: 84-87, SEQ ID NO: 109-114, 117 and 119;
- c. a nucleic acid molecule comprising a nucleotide sequence that has at least 90% sequence identity to the sequence shown in SEQ ID NOs: 84-87, SEQ ID NO: 109-114, 117 and 119;
- d. a nucleic acid molecule comprising a nucleotide sequence that has at least 95% sequence identity to the sequence shown in SEQ ID NOs: 84-87, SEQ ID NO: 109-114, 117 and 119;
- e. a nucleic acid molecule comprising a nucleotide sequence that has at least 98% sequence identity to the sequence shown in SEQ ID NOs: 84-87, SEQ ID NO: 109-114, 117 and 119;
- f. a nucleic acid molecule comprising a nucleotide sequence that has at least 99% sequence identity to the sequence shown in SEQ ID NOs: 84-87, SEQ ID NO: 109-114, 117 and 119;
- g. a nucleic acid molecule comprising a nucleotide sequence the complementary strand of which hybridizes to the nucleic acid molecule of any of a)-f);
- h. a nucleic acid molecule comprising a nucleotide sequence that deviates from the nucleotide sequence defined in any of a)-g) by the degeneracy of the genetic code, wherein said nucleic acid molecule as defined in any of a)-h) recognizes and specifically binds to a phospho-epitope on a mammalian, particularly on the human Tau protein or on a fragment thereof, particularly on the human Tau protein as shown in SEQ ID NO: 67, selected from the group consisting of Tau aa 393-401, comprising a phosphorylated Ser at position 396 (pS396), Tau aa 396-401 comprising a phosphorylated Ser at position 396 (pS396), Tau aa 394-400 comprising a phosphorylated Ser at position 396 (pS396), Tau aa 402-406 comprising a phosphorylated Ser at position 404 (pS404), and Tau aa 393-400 comprising a phosphorylated Ser at position 396 (pS396), wherein, in one embodiment, said binding peptide has a high binding affinity with a dissociation constant of at least 10 nM, particularly of at least 8 nM, particularly of at least 5 nM, particularly of at least 2 nM, particularly of at least 1 nM, particularly of at least 500 pM, particularly of at least 400 pM, particularly of at least 300 pM, particularly of at least 200 pM, particularly of at least 100 pM, particularly of at least 50 pM and/or has an association rate constant of $10^4$ $M^{-1}$ $s^{-1}$ or greater, particularly of between $3-5 \times 10^4$ $M^{-1}$ $s^{-1}$ or greater, particularly of $10^5$ $M^{-1}$ $s^{-1}$ or greater; particularly of $6-9 \times 10^5$ $M^{-1}$ $s^{-1}$ or greater; particularly of $10^6$ $M^{-1}$ $s^{-1}$ or greater, particularly of $1-4 \times 10^6$ $M^{-1}$ $s^{-1}$ or greater, particularly of $10^7$ $M^{-1}$ $s^{-1}$ or greater, but, in one embodiment, does not bind to the corresponding unphosphorylated epitope and/or to non-related epitopes.

In various embodiments (35) of the invention, a binding peptide is provided or a functional part thereof, particularly an antibody, particularly a monoclonal antibody or a functional part thereof, or a polynucleotide, according to any one of the preceding embodiments, or a combination thereof, which is capable of specifically recognizing and binding to a phospho-epitope on a mammalian, particularly on the human Tau protein, particularly a microtubule-associated protein tau, particularly an aggregated microtubule-associated and hyperphosphorylated protein tau such as that present in paired helical filaments (PHF), which are the predominant structures in neurofibrillary tangles, neuropil threads and dystrophic neurites, but, in one embodiment, does not bind to the corresponding unphosphorylated epitope and/or to non-related epitopes.

In a specific embodiment (36) of the invention, the human tau protein is the human Tau protein as shown in SEQ ID NO: 67.

The binding peptides and antibodies according to any one of the preceding embodiments can thus be used (37) for reducing the levels of total soluble tau protein, particularly of soluble phosphorylated tau protein, in the brain, particularly in the brain cortex and/or hippocampus, of a mammal or a human containing increased levels of soluble tau protein and/or soluble phosphorylated tau protein.

The binding peptides and antibodies according to any one of the preceding embodiments can also be used (38) for reducing the levels of paired helical filaments containing hyperphosphorylated tau protein (pTau PHF) in the brain, particularly in the brain cortex and/or hippocampus, of a mammal or a human containing increased levels of said pTau paired helical filaments.

Reduction of the level of total soluble tau protein and/or soluble phosphorylated tau protein and/or pTau paired helical filaments in the brain, particularly in the brain cortex and/or hippocampus, of a mammal or a human containing increased levels of said tau protein variants, which contribute to tau-protein-associated diseases, disorders or conditions in said mammal or human, may lead to an improvement and/or alleviation of the symptoms associated with such tau-protein-associated diseases, disorders or conditions (39).

The binding peptides and antibodies according to any one of the preceding embodiments can therefore be used (40) in therapy, particularly in human therapy, for slowing or halting the progression of a tau-protein-associated disease, disorder or condition.

The binding peptides and antibodies according to any one of the preceding embodiments can further be used (41) in therapy, particularly in human therapy, for improving or alleviating the symptoms associated with tau-protein-associated diseases, disorders or conditions such as, for example, impairment or loss of cognitive functions including reasoning, situational judgement, memory capacity, learning, special navigation, etc.

In one embodiment (42), the invention relates to the binding peptides and antibodies according to any one of the preceding embodiments for use in therapy, particularly for use in the treatment of tauopathies, a group of tau-protein-associated diseases and disorders, or for alleviating the symptoms associated with tauopathies.

In one embodiment (43), the invention relates to the binding peptides and antibodies according to any one of the preceding embodiments for retaining or increasing cognitive memory capacity in a mammal suffering from a tauopathy.

In another specific embodiment (44) of the invention, binding peptides and antibodies comprising at least one or all of the light chain CDRs of antibodies ACI-35-2A1-Ab1; ACI-35-2A1-Ab2; ACI-35-4A6-Ab1; ACI-35-4A6-Ab2; ACI-35-1D2-Ab1; ACI-35-2G5-Ab1; ACI-35-2G5-Ab2; ACI-35-2G5-Ab3; as given in SEQ ID NOs: 73-75, 81-83, 93-95, 101-103, 106-108 and/or at least one or all of the heavy chain CDRs of antibodies ACI-35-2A1-Ab1; ACI-35-2A1-Ab2; ACI-35-4A6-Ab1; ACI-35-4A6-Ab2; ACI-35-1D2-Ab1; ACI-35-2G5-Ab1; ACI-35-2G5-Ab2; ACI-35-2G5-Ab3; as given in SEQ ID NOs: 70-72, 78-80, 89-91, 98-100, (89, 115, 91) are used in therapy, particularly in human therapy, for improving or alleviating the symptoms associated with tau-protein-associated diseases, disorders or conditions such as, for example, impairment or loss of cognitive functions including reasoning, situational judgement, memory, learning, special navigation, etc.

In another specific embodiment (45) of the invention, binding peptides and antibodies comprising at least one or all of the light chain CDRs of antibodies ACI-35-2G5-Ab2; ACI-35-2G5-Ab3 as given in SEQ ID NOs: 106-108 and/or at least one or all of the heavy chain CDRs of antibodies ACI-35-2G5-Ab2; ACI-35-2G5-Ab3; as given in SEQ ID NOs: 89, 115 and 91, are used in therapy, particularly in human therapy, for improving or alleviating the symptoms associated with tau-protein-associated diseases, disorders or conditions such as, for example, impairment or loss of cognitive functions including reasoning, situational judgement, memory, learning, special navigation, etc.

Binding of the peptides or antibodies according to the preceding embodiments to tau tangles and pTau on brains may be determined by applying protein immuno-reactivity testing of selected brain sections and by Western blotting of brain homogenates, respectively, as described in the Examples.

In another embodiment (46), the present invention provides a pharmaceutical composition comprising a binding peptide or a functional part thereof, particularly an antibody, particularly a monoclonal antibody or a functional part thereof, or a polynucleotide, according to any one of the preceding embodiments, or a combination thereof, in a therapeutically effective amount together with a pharmaceutically acceptable carrier.

In one embodiment (47), the binding peptide or a functional part thereof, particularly an antibody, particularly a monoclonal antibody or a functional part thereof, or a polynucleotide, or a pharmaceutical composition, according to any one of the preceding embodiments, or a combination thereof, is used in therapy, particularly in human therapy for the treatment or alleviation of the symptoms of tau-protein-associated diseases or disorders including neurodegenerative disorders such as tauopathies.

The binding peptides, antibodies and/or pharmaceutical compositions according to any one of the preceding embodiments may thus be used (48) for slowing or halting the progression of a tau-protein-associated disease, disorder or condition, upon administration of said binding peptides, antibodies and/or pharmaceutical compositions to an animal, particularly a mammal, particularly a human, suffering from such a disease or condition.

The binding peptides, antibodies and/or pharmaceutical compositions according to any one of the preceding embodiments may further be used (49) for improving or alleviating the symptoms associated with tau-protein-associated diseases, disorders or conditions such as, for example, impairment or loss of cognitive functions including reasoning, situational judgement, memory capacity, learning, special navigation, etc, upon administration of said binding peptides, antibodies and/or pharmaceutical compositions to an animal, particularly a mammal, particularly a human, suffering from such a disease or condition.

In one embodiment (50), the binding peptide or a functional part thereof, particularly an antibody, particularly a monoclonal antibody or a functional part thereof, or a polynucleotide or a pharmaceutical composition, according to any one of the preceding embodiments, or a combination thereof, is used in the treatment of diseases and disorders which are caused by or associated with the formation of neurofibrillary lesions, the predominant brain pathology in tauopathy comprising a heterogeneous group of neurodegenerative diseases or disorders including diseases or disorders which manifest both tau and amyloid pathologies including, but not limited to, Alzheimer's Disease, Creutzfeldt-Jacob disease, Dementia pugilistica, Down's Syndrome, Gerstmann-Sträussler-Scheinker disease, inclusion-body myositis, and prion protein cerebral amyloid angiopathy, traumatic brain injury and further diseases or disorders which do not show a distinct amyloid pathology including, but not limited to, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia with parkinsonism linked to chromosome 17, Hallevorden-Spatz disease, multiple system atrophy, Niemann-Pick disease, type C, Pallido-ponto-nigral degeneration, Pick's disease, progressive subcortical gliosis, progressive supranuclear palsy, Subacute sclerosing panencephalitis, Tangle-only dementia, Postencephalitic Parkinsonism, Myotonic dystrophy.

In one embodiment (51), the binding peptide or a functional part thereof, particularly an antibody, particularly a monoclonal antibody or a functional part thereof, or a polynucleotide or a pharmaceutical composition, according to any one of the preceding embodiments, or a combination thereof, is used in the treatment of Alzheimer's Disease.

In one embodiment (52) of the invention, a method is provided for detecting and/or modulating levels of soluble and/or, oligomeric and/or insoluble phosphorylated Tau protein, particularly in vivo, particularly in the brain, particularly in the brain cortex and/or hippocampus, of an animal, particularly a mammal or a human, comprising administering to said animal, particularly to said mammal or human, the binding peptide or a functional part thereof, particularly an antibody, particularly a monoclonal antibody or a functional part thereof, or a polynucleotide or a pharmaceutical composition, according to any one of the preceding embodiments, or a combination thereof.

In one aspect, modulation relates to reducing the levels of soluble tau protein, particularly of soluble phosphorylated tau protein, in the brain, particularly in the brain cortex and/or hippocampus, of an animal, particularly a mammal or a human containing increased levels of soluble tau protein and/or soluble phosphorylated tau protein.

In one embodiment (53) of the invention, a method is provided for reducing the levels of insoluble tau protein, particularly of paired helical filaments containing hyperphosphorylated tau protein (pTau PHF) in the brain, particularly in the brain cortex and/or hippocampus, of an animal, particularly a mammal or a human, containing increased levels of insoluble tau protein, particularly of pTau paired helical filaments (pTau PHF) comprising administering to said animal, particularly to said mammal or human, the binding peptide or a functional part thereof, particularly an antibody, particularly a monoclonal antibody or a functional part thereof, or a polynucleotide or a pharmaceutical composition, according to any one of the preceding embodiments, or a combination thereof.

In one embodiment (54), the present invention relates to a method for slowing or halting the progression of a tau-protein-associated disease, disorder or condition in an animal, particularly a mammal or human comprising administering to said animal, particularly said mammal or human, suffering from such a disease or condition, the binding peptide or a functional part thereof, particularly an antibody, particularly a monoclonal antibody or a functional part thereof, or a polynucleotide or a pharmaceutical composition, according to any one of the preceding embodiments, or a combination thereof.

In one embodiment (55), the present invention relates to a method for improving or alleviating the symptoms associated with tau-protein-associated diseases, disorders or conditions such as, for example, impairment or loss of cognitive functions including reasoning, situational judgement, memory capacity, learning, special navigation, etc., in an animal, particularly a mammal or a human, comprising administering to said animal, particularly to said mammal or human, suffering from such a disease or condition, the binding peptide or a functional part thereof, particularly an antibody, particularly a monoclonal antibody or a functional part thereof, or a polynucleotide or a pharmaceutical composition, according to any one of the preceding embodiments, or a combination thereof.

In one embodiment (56), the present invention relates to a method for retaining or increasing cognitive memory capacity in a mammal suffering from a tauopathy.

In still another embodiment (57) of the invention, a method is provided for the treatment of a tau-protein-associated disease or disorder including a neurodegenerative disease or disorder such as a tauopathy comprising administering to an animal, particularly to a mammal, but especially to human, suffering from such a disease or disorder, the binding peptide or a functional part thereof, particularly an antibody, particularly a monoclonal antibody or a functional part thereof, or a polynucleotide or a pharmaceutical composition, according to any one of the preceding embodiments, or a combination thereof.

In one embodiment (58) of the invention, a method is provided for the treatment of diseases and disorders which are caused by or associated with the formation of neurofibrillary lesions, the predominant brain pathology in tauopathy comprising a heterogeneous group of neurodegenerative diseases or disorders including diseases or disorders which manifest both tau and amyloid pathologies including, but not limited to, Alzheimer's Disease, Creutzfeldt-Jacob disease, Dementia pugilistica, Down's Syndrome, Gerstmann-Sträussler-Scheinker disease, inclusion-body myositis, and prion protein cerebral amyloid angiopathy, traumatic brain injury and further diseases or disorders which do not show a distinct amyloid pathology including, but not limited to, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia with parkinsonism linked to chromosome 17, Hallevorden-Spatz disease, multiple system atrophy, Niemann-Pick disease, type C, Pallido-ponto-nigral degeneration, Pick's disease, progressive subcortical gliosis, progressive supranuclear palsy, Subacute sclerosing panencephalitis Tangle-only dementia, Postencephalitic Parkinsonism, Myotonic dystrophy, which method comprises administering to an animal, particularly to a mammal, but especially to human, suffering from such a disease or disorder, the binding peptide or a functional part thereof, particularly an antibody, particularly a monoclonal antibody or a functional part thereof, or a polynucleotide or a pharmaceutical composition according to any one of the preceding embodiments, or a combination thereof.

In another embodiment (59) of the invention, a method is provided for inducing a passive immune response in an animal, particularly a mammal or a human, suffering from a neurodegenerative disorder such as tauopathy by administering to said animal or human the binding peptide or a functional part thereof, particularly an antibody, particularly a monoclonal antibody or a functional part thereof, or a polynucleotide, or a pharmaceutical composition, according to any one of the preceding embodiments, or a combination thereof.

In still another embodiment (60) of the invention, a method of diagnosing a tau-protein-associated disease, disorder or condition in a patient is provided comprising detecting the immunospecific binding of a binding peptide or an active fragment thereof, particularly an antibody, particularly a monoclonal antibody or a functional part thereof, according to any one of the preceding embodiments, to an epitope of the tau protein in a sample or in situ which includes the steps of a. bringing the sample or a specific body part or body area suspected to contain the tau protein into contact with a binding peptide or a fragment thereof, particularly an antibody, particularly a monoclonal antibody or a functional part thereof, according to any one of the preceding claims, wherein said binding peptide or antibody or fragment thereof binds an epitope of the tau protein;
b. allowing said binding peptide, particularly said antibody, particularly said monoclonal antibody or a functional part thereof, to bind to the tau protein to form an immunological complex;
c. detecting the formation of the immunological complex; and
d. correlating the presence or absence of the immunological complex with the presence or absence of tau protein in the sample or specific body part or area.

In still another embodiment (61) of the invention, a method for diagnosing a predisposition to tau-protein-associated disease, disorder or condition in a patient is provided comprising detecting the immunospecific binding of a binding peptide or an active fragment thereof, particularly an antibody, particularly a monoclonal antibody or a functional part thereof, according to any one of the preceding embodiments, to an epitope of the tau protein in a sample or in situ, which includes the steps of
a. bringing the sample or a specific body part or body area suspected to contain the tau antigen into contact with a binding peptide or an active fragment thereof, particularly an antibody, particularly a monoclonal antibody or a functional part thereof, according to any one of the preceding embodiments, which peptide or fragment thereof binds an epitope of the tau protein;
b. allowing said binding peptide, particularly said antibody, particularly said monoclonal antibody or a functional part thereof, to bind to the tau antigen to form an immunological complex;
c. detecting the formation of the immunological complex; and
d. correlating the presence or absence of the immunological complex with the presence or absence of tau antigen in the sample or specific body part or area;
e. comparing the amount of said immunological complex to a normal control value;
wherein an increase in the amount of said aggregate compared to a normal control value indicates that said patient is suffering from or is at risk of developing an tau-protein-associated disease or condition.

In one embodiment (62) of the invention, a method is provided for monitoring minimal residual disease in a patient following treatment with the binding peptide or a functional part thereof, particularly an antibody, particularly a monoclonal antibody or a functional part thereof, or a polynucleotide, or a pharmaceutical composition, according to any one of the preceding embodiments, wherein said method comprises:
a. bringing the sample or a specific body part or body area suspected to contain the tau antigen into contact with the binding peptide or a functional part thereof, particularly an antibody, particularly a monoclonal antibody or a functional part thereof, according to any one of the preceding embodiments, which peptide or fragment thereof binds to an epitope of the tau protein;
b. allowing said binding peptide, particularly said antibody, particularly said monoclonal antibody or a functional part thereof, to bind to the tau antigen to form an immunological complex;
c. detecting the formation of the immunological complex; and
d. correlating the presence or absence of the immunological complex with the presence or absence of tau antigen in the sample or specific body part or area,
e. comparing the amount of said immunological complex to a normal control value,
wherein an increase in the amount of said aggregate compared to a normal control value indicates that said patient still suffers from a minimal residual disease.

In one embodiment (63), a method is provided for predicting responsiveness of a patient being treated with the binding peptide or a functional part thereof, particularly an antibody, particularly a monoclonal antibody or a functional part thereof, or a polynucleotide, or a pharmaceutical composition, according to any one of the preceding embodiments, comprising
a. bringing the sample or a specific body part or body area suspected to contain the tau antigen into contact with a binding peptide or an active fragment thereof, particularly an antibody, particularly a monoclonal antibody or a functional part thereof according to any one of the preceding embodiments, which peptide or fragment thereof binds to an epitope of the tau protein;
b. allowing said binding peptide, particularly said antibody, particularly said monoclonal antibody or a functional part thereof, to bind to the tau antigen to form an immunological complex;
c. detecting the formation of the immunological complex; and
d. correlating the presence or absence of the immunological complex with the presence or absence of tau antigen in the sample or specific body part or area,
e. comparing the amount of said immunological complex before and after onset of the treatment,
wherein a decrease in the amount of said aggregate indicates that said patient has a high potential of being responsive to the treatment.

Anti-Tau antibodies and fragments thereof may be used in the above methods of the invention. In the above methods the sample containing the antibody or fragment thereof may be immune-enriched to increase the concentration of Tau protein in the sample by contacting the sample with an anti-Tau antibody or a fragment thereof attached to a solid support.

Prior to the step (a), the sample is immune-enriched to increase the concentration of Tau protein in the sample by contacting the sample with an anti-Tau antibody or a fragment thereof attached to a solid support In another embodiment (64), the invention relates to a test kit for detection and diagnosis of tau-protein-associated diseases, disorders or conditions comprising a binding peptide or an active fragment thereof, particularly an antibody, particularly a monoclonal antibody or a functional part thereof, according to any one of the preceding embodiments.

In one embodiment (65) said test kit comprises a container holding one or more binding peptides or active fragments thereof, particularly an antibody, particularly a monoclonal antibody or a functional part thereof, according to any one of the preceding embodiments and instructions for using the binding peptides or antibodies for the purpose of binding to tau antigen to form an immunological complex and detecting the formation of the immunological complex such that presence or absence of the immunological complex correlates with presence or absence of tau antigen.

In still another embodiment (66), the present invention relates to an epitope on a mammalian, particularly on the human Tau protein as shown in SEQ ID NO: 67, selected from the group consisting of Tau aa 393-401, comprising a phosphorylated Ser at position 396 (pS396), Tau aa 396-401 comprising a phosphorylated Ser at position 396 (pS396), Tau aa 394-400 comprising a phosphorylated Ser at position 396 (pS396), Tau aa 402-406 comprising a phosphorylated Ser at position 404 (pS404) and Tau aa 393-400 comprising a phosphorylated Ser at position 396 (pS396).

In one embodiment (67), said epitope consists of Tau aa 393-401, comprising a phosphorylated Ser at position 396 (pS396).

In one embodiment (68), said epitope consists of Tau aa 396-401 comprising a phosphorylated Ser at position 396 (pS396).

In one embodiment (69), said epitope consists of Tau aa 394-400 comprising a phosphorylated Ser at position 396 (pS396).

In one embodiment (70), said epitope consists of Tau aa 402-406 comprising a phosphorylated Ser at position 404 (pS404).

In one embodiment (71), said epitope consists of Tau aa 393-400 comprising a phosphorylated Ser at position 396 (pS396).

In another embodiment (72), the invention relates to a cell line producing a binding peptide or an active fragment thereof, particularly an antibody, particularly a monoclonal antibody or a functional part thereof according to any one of the preceding embodiments.

In one embodiment (73), the invention relates to a cell line, which is hybridoma cell line A4-4A6-48 deposited on Aug. 30, 2011 as DSM ACC3136.

In one embodiment (74), the invention relates to a cell line, which is hybridoma cell line A6-2G5-30 deposited on Aug. 30, 2011 as DSM ACC3137.

In one embodiment (75), the invention relates to a cell line, which is hybridoma cell line A6-2G5-41 deposited on Aug. 30, 2011 as DSM ACC3138.

In one embodiment (76), the invention relates to a cell line, which is hybridoma cell line A4-2A1-18 deposited on Aug. 30, 2011 as DSM ACC3139.

In one embodiment (77), the invention relates to a cell line, which is hybridoma cell line A4-2A1-40 deposited on Aug. 30, 2011 as DSM ACC3140.

In one embodiment (78), the invention relates to a cell line, which is hybridoma cell line A6-1D2-12 deposited on Sep. 6, 2011 as DSM ACC3141.

In one embodiment (79), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line A4-2A1-18 deposited on Aug. 30, 2011 as DSM ACC3139 using
   a. a primer pair comprising a 5'-primer of SEQ ID NO: 149 and a 3'-primer of SEQ ID NO: 51 for amplification of a first binding domain; and/or
   b. a mix of primers comprising a 5'-primer selected from the group consisting of SEQ ID NOs: 120, 123, 124, 136, 137, 138, 139, and 140 and a 3'-primer selected from the group consisting of SEQ ID NOs: 131, 134, and 141-148, for amplification of a second binding domain.

In one embodiment (80), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line A6-2G5-30 deposited on Aug. 30, 2011 as DSM ACC3137 using
   a. a mix of primers comprising a 5'-primer selected from the group consisting of SEQ ID NOs: 51 and 169-174 and a 3'-primer of SEQ ID NO: 51, for amplification of a first binding domain; and/or
   b. a mix of primers comprising a 5'-primer selected from the group consisting of SEQ ID NOs: 124, 127, and 150-158 and a 3'-primer selected from the group consisting of SEQ ID NOs: 130, and 159-168, for amplification of a second binding domain.

In one embodiment (81), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line A4-2A1-40 deposited on Aug. 30, 2011 as DSM ACC3140 using
   a. a mix of primers comprising a 5'-primer selected from the group consisting of SEQ ID NOs: 178, 179 and 180 and a 3'-primer of SEQ ID NO: 51, for amplification of a first binding domain; and/or
   b. a mix of primers comprising a 5'-primer selected from the group consisting of SEQ ID NOs: 121, 127, 139, 154, 155, and 175 and a 3'-primer selected from the group consisting of SEQ ID NOs: 128, 129, 147, 176, and 177, for amplification of a second binding domain.

In one embodiment (82), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line A6-2G5-41 deposited on Aug. 30, 2011 as DSM ACC3138 using
   a. a mix of primers comprising a 5'-primer selected from the group consisting of SEQ ID NOs: 51 and 188-192 and a 3'-primer of SEQ ID NO: 51, for amplification of a first binding domain; and/or
   b. a mix of primers comprising a 5'-primer selected from the group consisting of SEQ ID NOs: 120, 124, 126, 181, 182 and 183 and a 3'-primer selected from the group consisting of SEQ ID NOs: 144, 145 and 184-187, for amplification of a second binding domain.

In one embodiment (83), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line A4-4A6-48 deposited on Aug. 30, 2011 as DSM ACC3136 using
   a. a mix of primers comprising a 5'-primer selected from the group consisting of SEQ ID NOs: 50 and 201-204 and a 3'-primer of SEQ ID NO: 51, for amplification of a first binding domain; and/or
   b. a mix of primers comprising a 5'-primer selected from the group consisting of SEQ ID NOs: 121, 137, 151 and 193-197 and a 3'-primer selected from the group consisting of SEQ ID NOs: 131, 141, 144, 166, 198, 199 and 200, for amplification of a second binding domain.

In one embodiment (84), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line A6-1D2-12 deposited on Sep. 6, 2011 as DSM ACC3141 using
  a. a mix of primers comprising a 5'-primer selected from the group consisting of SEQ ID NOs: 209-214, and 219-221 a 3'-primer of SEQ ID NO: 215, for amplification of a first binding domain; and/or
  b. a mix of primers comprising a 5'-primer selected from the group consisting of SEQ ID NOs: 216, 217 and 218 and a 3'-primer of SEQ ID NOs: 208, for amplification of a second binding domain.

In one embodiment (85), the antibody according to any one of the preceding embodiments may be a polyclonal antibody, a monoclonal antibody, a chimeric antibody, a humanized antibody, a human antibody, a camelid antibody, a diabody, or a modified or engineered antibody.

In one embodiment (86), the invention provides a method for producing the binding peptides or antibodies of any one of the preceding embodiments, comprising the step of culturing the cell line of any of the preceding embodiments in a suitable cultivation medium and, optionally, purifying the binding peptides or antibody from the cell line or cultivation medium.

In another embodiment (87), the present invention provides a method of detecting phosphoTau (pTau) multimers in a brain sample comprising
  a. bringing the sample into contact with an antibody or a fragment thereof according to any one of the preceding claims, which peptide or fragment thereof binds an epitope of the phosphoTau protein;
  b. allowing the antibody to bind to the tau protein to form an immunological complex;
  c. detecting the formation of the immunological complex, particularly by applying an ELISA assay.

In particular, the invention relates in a specific embodiment (88) to a method of post mortem detection of phosphoTau (pTau) multimers in brain homogenates from a subject suspected to suffer from a tau-associated disease or disorder and from a healthy control subject comprising
  a. bringing a sample of brain homogenates from both subjects into contact with an antibody or a fragment thereof according to any one of the preceding claims, which peptide or fragment thereof binds an epitope of the phosphoTau protein;
  b. allowing the antibody to bind to the tau protein to form an immunological complex;
  c. detecting the formation of the immunological complex, particularly by applying an ELISA assay and
  d. comparing the amount or intensity of the immunological complex in the sample obtained from the subject suspected to suffer from a tau-associated disease or to that of the control sample,
wherein an increase in the amount or intensity of said immunological complex compared to the control value indicates that said patient had suffered from a minimal residual disease.

In one embodiment (89), the increase observed in the test sample compared to the control sample is between 30% and 50%, particularly between 35% and 45%.

In one embodiment (90) the invention provides an a binding peptide or protein or a functional part thereof, particularly to an antibody, particularly a monoclonal antibody or a functional part thereof, according to any one of the preceding embodiment, which antibody or fragment shows a favourable pK profile. In particular, said antibody or fragment has a high serum concentration up to 10-day post administration, which indicates a pharmacokinetic (PK) profile that favorably supports the use of said antibodies as a therapeutic antibody. (Deng et al., Expert Opin Drug Metab Toxicol, 2012, 8(2) 141-60; Putman et al., Trends Biotech, 2010 (28) 509-516; Bai, S. Clin Pharmacokinet 2012; 51 (2): 119-135.

BRIEF DESCRIPTION OF FIGURES AND SEQUENCES

Figures

SEQUENCES

Figure 1:
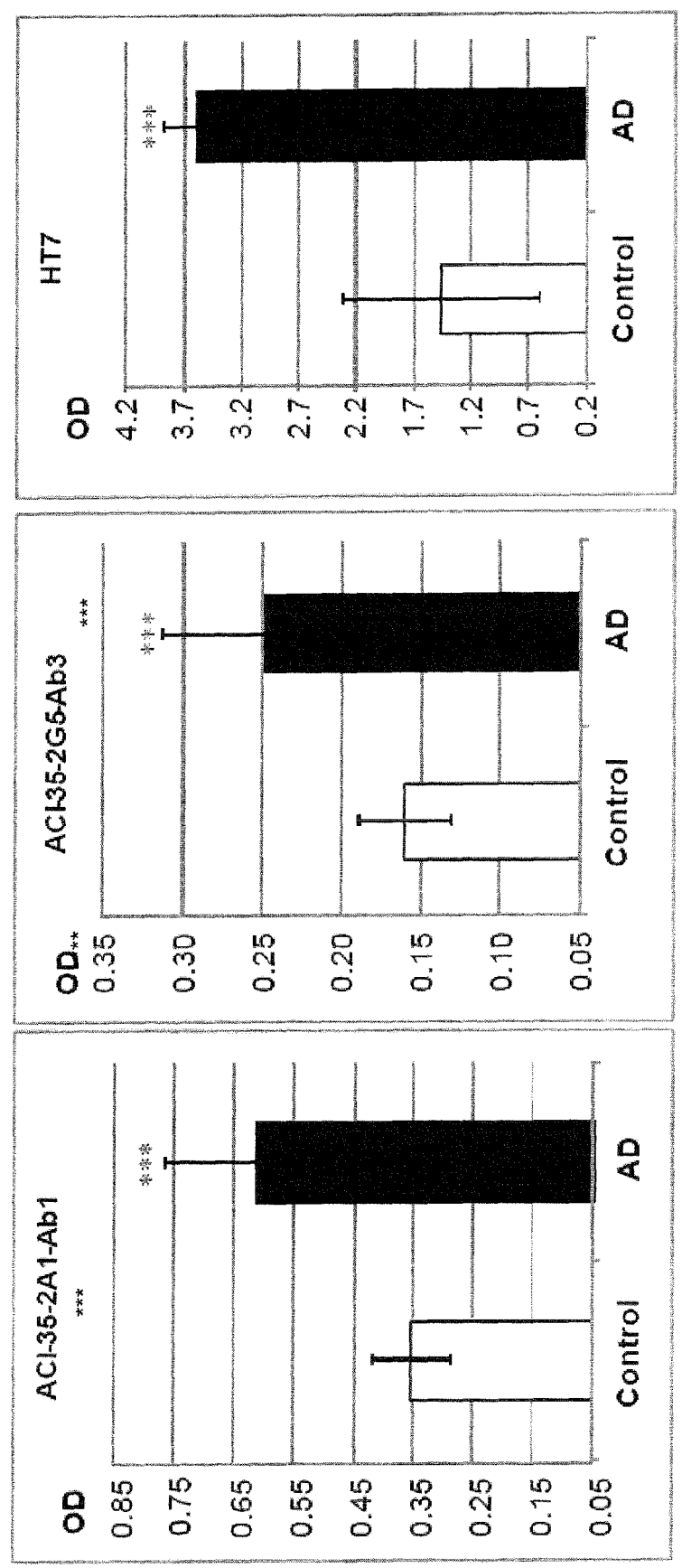
FIG. 1 shows results of detection of phosphorylated Tau multimers by ACI-35-2A1-Ab1 (left panel), ACI-35-2G5-Ab3 (middle panel), and a control antibody (HT7; right panel) in human brain homogenates from control and AD subjects.

SEQ ID NO: 46-57 depicts the nucleotide sequences of VM/VK forward and reverse primers.

SEQ ID NO: 62 depicts the amino acid sequence of Tau antigen, peptide T3 (see Table 1).

SEQ ID NO: 67 depicts the amino acid sequence of longest isoform of human tau (441 aa) also called Tau40.

SEQ ID NO: 68 depicts the amino acid sequence of the heavy chain variable region (VH) of monoclonal antibody ACI-35-4A6-Ab1 produced by hybridoma cell line A4-4A6-18.

SEQ ID NO: 69 depicts the amino acid sequence of the light chain variable region (VK) of monoclonal antibody ACI-35-4A6-Ab1 produced by hybridoma cell line A4-4A6-18.

SEQ ID NO: 70 depicts the amino acid sequence of the CDR1 of the heavy chain variable region (VH) of monoclonal antibody ACI-35-4A6-Ab1.

SEQ ID NO: 71 depicts the amino acid sequence of the CDR2 of the heavy chain variable region (VH) of monoclonal antibody ACI-35-4A6-Ab1.

SEQ ID NO: 72 depicts the amino acid sequence of the CDR3 of the heavy chain variable region (VH) of monoclonal antibody ACI-35-4A6-Ab1.

SEQ ID NO: 73 depicts the amino acid sequence of the CDR1 of the light chain variable region (VK) of monoclonal antibody ACI-35-4A6-Ab1.

SEQ ID NO: 74 depicts the amino acid sequence of the CDR2 of the light chain variable region (VK) of monoclonal antibody ACI-35-4A6-Ab1.

SEQ ID NO: 75 depicts the amino acid sequence of the CDR3 of the light chain variable region (VK) of monoclonal antibody ACI-35-4A6-Ab1.

SEQ ID NO: 76 depicts the amino acid sequence of the heavy chain variable region (VH) of monoclonal antibody ACI-35-1D2-Ab1 produced by hybridoma cell line A6-1D2-12.

SEQ ID NO: 77 depicts the amino acid sequence of the light chain variable region (VK) of monoclonal antibody ACI-35-1D2-Ab1 produced by hybridoma cell line A6-1D2-12.

SEQ ID NO: 78 depicts the amino acid sequence of the CDR1 of the heavy chain variable region (VH) of monoclonal antibody ACI-35-1D2-Ab1.

SEQ ID NO: 79 depicts the amino acid sequence of the CDR2 of the heavy chain variable region (VH) of monoclonal antibody ACI-35-1D2-Ab1.

SEQ ID NO: 80 depicts the amino acid sequence of the CDR3 of the heavy chain variable region (VH) of monoclonal antibody ACI-35-1D2-Ab1.

SEQ ID NO: 81 depicts the amino acid sequence of the CDR1 of the light chain variable region (VK) of monoclonal antibody ACI-35-1D2-Ab1.

SEQ ID NO: 82 depicts the amino acid sequence of the CDR2 of the light chain variable region (VK) of monoclonal antibody ACI-35-1D2-Ab1.

SEQ ID NO: 83 depicts the amino acid sequence of the CDR3 of the light chain variable region (VK) of monoclonal antibody ACI-35-1D2-Ab1.

SEQ ID NO: 84 depicts the nucleotide sequence of the heavy chain variable region (VH) of monoclonal antibody ACI-35-4A6-Ab1 produced by hybridoma cell line A4-4A6-18.

SEQ ID NO: 85 depicts the nucleotide sequence of the light chain variable region (VK) of monoclonal antibody ACI-35-4A6-Ab1 produced by hybridoma cell line A4-4A6-18.

SEQ ID NO: 86 depicts the nucleotide sequence of the heavy chain variable region (VH) of monoclonal antibody ACI-35-1D2-Ab1 produced by hybridoma cell line A6-1D2-12.

SEQ ID NO: 87 depicts the nucleotide sequence of the light chain variable region (VK) of monoclonal antibody ACI-35-1D2-Ab1 produced by hybridoma cell line A6-1D2-12.

SEQ ID NO: 88 depicts the amino acid sequence of the heavy chain variable region (VH) of monoclonal antibody ACI-35-2A1-Ab1, ACI-35-2A1-Ab2, and ACI-35-4A6-Ab2, respectively, produced by hybridoma cell line A4-2A1-18, A4-2A1-40 and A4-4A6-48, respectively.

SEQ ID NO: 89 depicts the amino acid sequence of the CDR1 of the heavy chain variable region (VH) of monoclonal antibody ACI-35-2A1-Ab1, ACI-35-2A1-Ab2, ACI-35-4A6-Ab2, ACI-35-2G5-AB2 and ACI-35-2G5-AB3, respectively.

SEQ ID NO: 90 depicts the amino acid sequence of the CDR2 of the heavy chain variable region (VH) of monoclonal antibody ACI-35-2A1-Ab1. ACI-35-2A1-Ab2, and ACI-35-4A6-Ab2, respectively.

SEQ ID NO: 91 depicts the amino acid sequence of the CDR3 of the heavy chain variable region (VH) of monoclonal antibody ACI-35-2A1-Ab1, ACI-35-2A1-Ab2, ACI-35-4A6-Ab2, ACI-35-2G5-AB2 and ACI-35-2G5-AB3, respectively.

SEQ ID NO: 92 depicts the amino acid sequence of the light chain variable region (VK) of monoclonal antibody ACI-35-2A1-Ab2 produced by hybridoma cell line A4-2A1-40

SEQ ID NO: 93 depicts the amino acid sequence of the CDR1 of the light chain variable region (VK) of monoclonal antibody ACI-35-2A1-Ab2.

SEQ ID NO: 94 depicts the amino acid sequence of the CDR2 of the light chain variable region (VK) of monoclonal antibody ACI-35-2A1-Ab2.

SEQ ID NO: 95 depicts the amino acid sequence of the CDR3 of the light chain variable region (VK) of monoclonal antibody ACI-35-2A1-Ab2.

SEQ ID NO: 96 depicts the amino acid sequence of the heavy chain variable region (VH) of monoclonal antibody ACI-35-2G5-Ab1 produced by hybridoma cell line A6-2G5-08.

SEQ ID NO: 97 depicts the amino acid sequence of the light chain variable region (VK) of monoclonal antibody ACI-35-2G5-Ab1 produced by hybridoma cell line A6-2G5-08.

SEQ ID NO: 98 depicts the amino acid sequence of the CDR1 of the heavy chain variable region (VH) of monoclonal antibody ACI-35-2G5-Ab1.

SEQ ID NO: 99 depicts the amino acid sequence of the CDR2 of the heavy chain variable region (VH) of monoclonal antibody ACI-35-2G5-Ab1.

SEQ ID NO: 100 depicts the amino acid sequence of the CDR3 of the heavy chain variable region (VH) of monoclonal antibody ACI-35-2G5-Ab1.

SEQ ID NO: 101 depicts the amino acid sequence of the CDR1 of the light chain variable region (VK) of monoclonal antibody ACI-35-2G5-Ab1.

SEQ ID NO: 102 depicts the amino acid sequence of the CDR2 of the light chain variable region (VK) of monoclonal antibody ACI-35-2G5-Ab1.

SEQ ID NO: 103 depicts the amino acid sequence of the CDR3 of the light chain variable region (VK) of monoclonal antibody ACI-35-2G5-Ab1.

SEQ ID NO: 104 depicts the amino acid sequence of the heavy chain variable region (VH) of monoclonal antibody ACI-35-2G5-AB2 and ACI-35-2G5-AB3, respectively, produced by hybridoma cell line A6-2G5-30 and A6-2G5-41, respectively.

SEQ ID NO: 105 depicts the amino acid sequence of the light chain variable region (VK) of monoclonal antibody ACI-35-2G5-AB2 and ACI-35-2G5-AB3, respectively, produced by hybridoma cell line A6-2G5-30 and A6-2G5-41, respectively.

SEQ ID NO: 106 depicts the amino acid sequence of the CDR1 of the light chain variable region (VK) of monoclonal antibody ACI-35-2G5-AB2 and ACI-35-2G5-AB3, respectively.

SEQ ID NO: 107 depicts the amino acid sequence of the CDR2 of the light chain variable region (VK) of monoclonal antibody ACI-35-2G5-AB2 and ACI-35-2G5-AB3, respectively.

SEQ ID NO: 108 depicts the amino acid sequence of the CDR3 of the light chain variable region (VK) of monoclonal antibody ACI-35-2G5-AB2 and ACI-35-2G5-AB3, respectively.

SEQ ID NO: 109 depicts the nucleotide sequence of the heavy chain variable region (VH) of monoclonal antibody ACI-35-2A1-Ab1, ACI-35-2A1-Ab2, and ACI-35-4A6-Ab2, respectively, produced by hybridoma cell line A4-2A1-18, A4-2A1-40 and A4-4A6-48, respectively.

SEQ ID NO: 110 depicts the nucleotide sequence of the light chain variable region (VK) of monoclonal antibody ACI-35-2A1-Ab2 produced by hybridoma cell line A4-2A1-40.

SEQ ID NO: 111 depicts the nucleotide sequence of the heavy chain variable region (VH) of monoclonal antibody ACI-35-2G5-AB1 produced by hybridoma cell line A6-2G5-08.

SEQ ID NO: 112 depicts the nucleotide sequence of the light chain variable region (VK) of monoclonal antibody ACI-35-2G5-AB1 produced by hybridoma cell line A6-2G5-08.

SEQ ID NO: 113 depicts the nucleotide sequence of the heavy chain variable region (VH) of monoclonal antibody ACI-35-2G5-AB2 and ACI-35-2G5-AB3, respectively, produced by hybridoma cell line A6-2G5-30 and A6-2G5-41, respectively.

SEQ ID NO: 114 depicts the nucleotide sequence of the light chain variable region (VK) of monoclonal antibody ACI-35-2G5-AB2 and ACI-35-2G5-AB3, respectively, produced by hybridoma cell line A6-2G5-30 and A6-2G5-41, respectively.

SEQ ID NO: 115 depicts the amino acid sequence of the CDR2 of the heavy chain variable region (VH) of monoclonal antibody ACI-35-2G5-AB2 and ACI-35-2G5-AB3.

SEQ ID NO: 116 depicts the amino acid sequence of the light chain variable region (VK) of monoclonal antibody ACI-35-2A1-Ab1 produced by hybridoma cell line A4-2A1-18.

SEQ ID NO: 117 depicts the nucleotide sequence of the light chain variable region (VK) of monoclonal antibody ACI-35-2A1-Ab1 produced by hybridoma cell line A4-2A1-18.

SEQ ID NO: 118 depicts the amino acid sequence of the light chain variable region (VK) of monoclonal antibody ACI-35-4A6-Ab2 produced by hybridoma cell line A4-4A6-48.

SEQ ID NO: 119 depicts the nucleotide sequence of the light chain variable region (VK) of monoclonal antibody ACI-35-4A6-Ab2 produced by hybridoma cell line A4-4A6-48.

SEQ ID NO: 120-221 depicts the nucleotide sequences of VH/VK forward and reverse primers.

DEFINITION OF TERMS

The terms "polypeptide", "peptide", and "protein", as used herein, are interchangeably and are defined to mean a biomolecule composed of amino acids linked by a peptide bond.

The term "peptides," or "binding peptide" are used herein interchangeably and refer to chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the peptide, or to the alpha-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide. A binding peptide may constitutes antibodies such as polyclonal or monoclonal antibodies, human or humanized antibodies, diabodies, camelid antibodies, etc., or functional parts thereof as defined herein.

The terms "fragment thereof" or "fragment" as used herein in the context of a peptide refer to a functional peptide fragment which has essentially the same (biological) activity as an intact peptide defined herein. The terms when used herein in the context of an antibody refers to an antibody fragment comprising a portion of an intact antibody that contains an antigen binding or variable region of the intact antibody. Examples of antibody fragments include Fab, Fab', F(ab')$_2$, and Fv fragments; diabodies; single-chain antibody molecules, including single-chain Fv (scFv) molecules; and bispecific and multispecific antibodies and/or antibody fragments.

Typically, the amino acids making up a peptide are numbered in order, starting at the amino terminal and increasing in the direction toward the carboxy terminal of the peptide. Thus, when one amino acid is said to "follow" another, that amino acid is positioned closer to the carboxy terminal of the peptide than the preceding amino acid.

The term "residue" is used herein to refer to an amino acid that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

The phrase "consisting essentially of" is used herein to exclude any elements that would substantially alter the essential properties of the peptides to which the phrase refers. Thus, the description of a peptide "consisting essentially of . . . " excludes any amino acid substitutions, additions, or deletions that would substantially alter the biological activity of that peptide.

Furthermore, one of skill will recognize that, as mentioned above, individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The phrases "isolated" or "biologically pure" refer to material which is substantially or essentially free from components which normally accompany it as found in its native state. Thus, the peptides described herein do not contain materials normally associated with their in situ environment. Typically, the isolated, immunogenic peptides described herein are at least about 80% pure, usually at least about 90%, and preferably at least about 95% as measured by band intensity on a silver stained gel.

Protein purity or homogeneity may be indicated by a number of methods well known in the art, such as polyacrylamide gel electrophoresis of a protein sample, followed by visualization upon staining. For certain purposes high resolution will be needed and HPLC or a similar means for purification utilized.

When the immunogenic peptides are relatively short in length (i.e., less than about 50 amino acids), they are often synthesized using standard chemical peptide synthesis techniques.

Solid phase synthesis in which the C-terminal amino acid of the sequence is attached to an insoluble support followed by sequential addition of the remaining amino acids in the sequence is a preferred method for the chemical synthesis of the immunogenic peptides described herein. Techniques for solid phase synthesis are known to those skilled in the art.

Alternatively, the immunogenic peptides described herein are synthesized using recombinant nucleic acid methodology. Generally, this involves creating a nucleic acid sequence that encodes the peptide, placing the nucleic acid in an expression cassette under the control of a particular promoter, expressing the peptide in a host, isolating the expressed peptide or polypeptide and, if required, renaturing the peptide. Techniques sufficient to guide one of skill through such procedures are found in the literature.

Once expressed, recombinant peptides can be purified according to standard procedures, including ammonium sulfate precipitation, affinity columns, column chromatography, gel electrophoresis and the like. Substantially pure compositions of about 50% to 95% homogeneity are preferred, and 80% to 95% or greater homogeneity is most preferred for use as therapeutic agents.

One of skill in the art will recognize that after chemical synthesis, biological expression or purification, the immunogenic peptides may possess a conformation substantially different than the native conformations of the constituent peptides. In this case, it is often necessary to denature and reduce the antiproliferative peptide and then to cause the peptide to re-fold into the preferred conformation. Methods of reducing and denaturing proteins and inducing re-folding are well known to those of skill in the art.

Antigenicity of the purified protein may be confirmed, for example, by demonstrating reaction with immune serum, or with antisera produced against the protein itself.

The terms "a", "an" and "the" as used herein are defined to mean "one or more" and include the plural unless the context is inappropriate.

The terms "detecting" or "detected" as used herein mean using known techniques for detection of biologic molecules such as immunochemical or histological methods and refer to qualitatively or quantitatively determining the presence or concentration of the biomolecule under investigation.

By "isolated" is meant a biological molecule free from at least some of the components with which it naturally occurs.

The terms "antibody" or "antibodies" or "functional parts thereof" as used herein is an art recognized term and is understood to refer to molecules or active fragments of molecules that bind to known antigens, particularly to immunoglobulin molecules and to immunologically active portions of immunoglobulin molecules, i.e molecules that contain a binding site that immunospecifically binds an antigen. The immunoglobulin according to the invention can be of any type (IgG, IgM, IgD, IgE, IgA and IgY) or class (IgG1, IgG2, IgG3, IgG4, IgA1 and IgA2) or subclasses of immunoglobulin molecule.

"Antibodies" are intended within the scope of the present invention to include monoclonal antibodies, polyclonal, chimeric, single chain, bispecific, simianized, human and humanized antibodies, camelid antibodies, diabodies, as well as functional parts or active fragments thereof. Examples of active fragments of molecules that bind to known antigens include Fab and F(ab')$_2$ fragments, including the products of a Fab immunoglobulin expression library and epitope-binding fragments of any of the antibodies and fragments mentioned above.

These active fragments can be derived from an antibody of the present invention by a number of techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, (1986).

A "humanized antibody" refers to a type of engineered antibody having its CDRs derived from a non-human donor immunoglobulin, the remaining immunoglobulin-derived parts of the molecule being derived from one (or more) human immunoglobulin(s).

A humanized antibody may further refer to an antibody having a variable region where one or more of its framework regions have human or primate amino acids. In addition, framework support residues may be altered to preserve binding affinity. Methods to obtain "humanized antibodies" are well known to those skilled in the art. (see, e.g., Queen et al., Proc. Natl Acad Sci USA, 86:10029-10032 (1989), Hodgson et al., Bio/Technoloy, 9:421 (1991)).

A "humanized antibody" may also be obtained by a novel genetic engineering approach that enables production of affinity-matured humanlike polyclonal antibodies in large animals such as, for example, rabbits (http://www.rctech.com/bioventures/therapeutic.php).

The term "fully human antibody" or "human" antibody is meant to refer to an antibody derived from transgenic mice carrying human antibody genes or from human cells. To the human immune system, however, the difference between "fully human", "human", and "humanized" antibodies may be negligible or nonexistent and as such all three may be of equal efficacy and safety.

The term "monoclonal antibody" is also well recognized in the art and refers to an antibody that is mass produced in the laboratory from a single clone and that recognizes only one antigen. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces large quantities of the antibody.

The term "antigen" refers to an entity or fragment thereof which can induce an immune response in an organism, particularly an animal, more particularly a mammal including a human. The term includes immunogens and regions responsible for antigenicity or antigenic determinants.

As used herein, the term "soluble" means partially or completely dissolved in an aqueous solution.

Also as used herein, the term "immunogenic" refers to substances which elicit or enhance the production of antibodies, T-cells and other reactive immune cells directed against an immunogenic agent and contribute to an immune response in humans or animals.

An immune response occurs when an individual produces sufficient antibodies, T-cells and other reactive immune cells against administered immunogenic compositions of the present invention to moderate or alleviate the disorder to be treated.

The term "hybridoma" is art recognized and is understood by those of ordinary skill in the art to refer to a cell produced by the fusion of an antibody-producing cell and an immortal cell, e.g. a multiple myeloma cell. This hybrid cell is capable of producing a continuous supply of antibody. See the definition of "monoclonal antibody" above and the Examples below for a more detailed description of the method of fusion.

The term "carrier" as used herein means a structure in which antigenic peptide or supramolecular construct can be incorporated into or can be associated with, thereby presenting or exposing antigenic peptides or part of the peptide to the immune system of a human or animal. Any particle that can be suitably used in animal or human therapy such as, for example, a vesicle, a particle or a particulate body may be used as a carrier within the context of the present invention.

The term "carrier" further comprises methods of delivery wherein supramolecular antigenic construct compositions comprising the antigenic peptide may be transported to desired sites by delivery mechanisms. One example of such a delivery system utilizes colloidal metals such as colloidal gold.

Carrier proteins that can be used in the supramolecular antigenic construct compositions of the present invention include, but are not limited to, maltose binding peptide "MBP"; bovine serum albumin "BSA"; keyhole lympet hemocyanin "KLH"; ovalbumin; flagellin; thyroglobulin; serum albumin of any species; gamma globulin of any species; syngeneic cells; syngeneic cells bearing Ia antigens; and polymers of D- and/or L-amino acids.

Further, the term "therapeutically effective amount" or "pharmaceutically effective amount" refers to the amount of binding peptide which, when administered to a human or animal, is sufficient to result in a therapeutic effect in said human or animal. The effective amount is readily determined by one of ordinary skill in the art following routine procedures.

"pTau PHF", "PHF", and "paired helical filaments" are used herein synonymously and refer to pairs of approximately 10 nm filaments wound into helices with a periodicity of 160 nm visible on electron microscopy. Width varies between 10 and 22 nm. PHF are the predominant structures in neurofibrillary tangles of Alzheimer's Disease (AD) and neuropil threads. PHF may also be seen in some but not all dystrophic neurites associated with neuritic plaques. The major component of PHF is a hyperphosphorylated form of microtubule-associated protein tau. PHF are composed of disulfide-linked antiparallel hyper-phosphorylated tau proteins. PHF tau may be truncated of its C-terminal 20 amino acid residues. The mechanisms underlying PHF formation are uncertain but hyper-phosphorylation of tau may disengage it from microtubules, increasing the soluble pool of tau.

Within the scope of the present invention, it was demonstrated that the antibody induced response to the antigenic composition according to the invention is largely T-cell independent. A nude mouse model was used in this respect and nude mice were vaccinated and antibody responses measured to evaluate the Aβ-specific antibody response induced by the antigenic composition according to the invention in the immunized nude mice. The nude mice carry the Foxn1nu mutation and as a consequence, have reduced T-cell function due to the lack of a proper thymus.

A "pharmaceutically effective amount" as used herein refers to a dose of the active ingredient in a pharmaceutical composition adequate to cure, or at least partially arrest, the symptoms of the disease, disorder or condition to be treated or any complications associated therewith.

The present invention provides binding peptides recognizing and binding to major pathological phospho-epitopes of the tau protein. In particular, the present invention provides specific antibodies against linear and conformational, simple and complex phospho-epitopes on protein tau that are believed to be responsible for synapto- and neuro-toxicity in tauopathies, including AD.

Accordingly, the present invention relates in one embodiment to a binding peptide or a functional part thereof, particularly to an antibody, particularly a monoclonal antibody or a functional part thereof, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes, wherein said binding peptide or antibody has a high binding affinity with a dissociation constant of at least 10 nM, particularly of at least 8 nM, particularly of at least 5 nM, particularly of at least 2 nM, particularly of at least 1 nM, particularly of at least 500 pM, particularly of at least 400 pM particularly of at least 300 pM, particularly of at least 200 pM, particularly of at least 100 pM, particularly of at least 50 pM.

"Soluble Tau" protein as used herein refers to proteins consisting of both completely solubilized Tau protein/peptide monomers or of Tau-like peptides/proteins, or of modified or truncated Tau peptides/proteins or of other derivates of Tau peptides/proteins monomers, and of Tau protein oligomers. "Soluble Tau" excludes particularly neurofibrillary tangles (NFT).

"Insoluble Tau" as used herein refers to multiple aggregated monomers of Tau peptides or proteins, or of Tau-like peptides/proteins, or of modified or truncated Tau peptides/proteins or of other derivates of Tau peptides/proteins forming oligomeric or polymeric structures which are insoluble both in vitro in aqueous medium and in vivo in the mammalian or human body more particularly in the brain, but particularly to multiple aggregated monomers of Tau or of modified or truncated Tau peptides/proteins or of derivatives thereof, which are insoluble in the mammalian or human body more particularly in the brain, respectively. "Insoluble Tau" particularly includes neurofibrillary tangles (NFT).

""Monomeric Tau" or "Tau monomer" as used herein refers to completely solubilized Tau proteins without aggregated complexes in aqueous medium.

"Aggregated Tau", "oligomeric Tau" and "Tau oligomer" refer to multiple aggregated monomers of Tau peptides or proteins, or of Tau-like peptides/proteins, or of modified or truncated Tau peptides/proteins or of other derivates of Tau peptides/proteins forming oligomeric or polymeric structures which are insoluble or soluble both in vitro in aqueous medium and in vivo in the mammalian or human body more particularly in the brain, but particularly to multiple aggregated monomers of Tau or of modified or truncated Tau peptides/proteins or of derivatives thereof, which are insoluble or soluble in the mammalian or human body more particularly in the brain, respectively."

A "modulating antibody" refers to an antibody or a functional fragment thereof as described herein in the various embodiments, which may either up-regulate (e.g., activate or stimulate), down-regulate (e.g., inhibit or suppress) or otherwise change a functional property, biological activity or level of soluble and/or insoluble and/or oligomeric Tau protein, particularly of soluble phosphorylated tau protein, in vivo, particularly in the brain, particularly in the brain cortex and/or hippocampus, of an animal, particularly a mammal or a human containing increased levels of soluble tau protein and/or soluble phosphorylated tau protein. A modulating antibody or functional fragment thereof may act to modulate a tau protein or a polypeptide encoding said tau protein either directly or indirectly. In certain embodiments, a modulating antibody or functional fragment thereof reduces the levels of soluble and/or insoluble and/or oligomeric, particularly soluble and insoluble tau protein, particularly soluble and insoluble and oligomeric tau protein. In one aspect, the soluble and/or insoluble and/or oligomeric tau protein is phosphorylated tau protein, particularly soluble phosphorylated tau protein, in the brain, particularly in the brain cortex and/or hippocampus, of an animal, particularly a mammal or a human containing increased levels of tau protein and/or phosphorylated tau protein, particularly of soluble tau protein and/or soluble phosphorylated tau protein."

In one embodiment, the present invention provides a pharmaceutical composition comprising a binding peptide or a functional part thereof, particularly an antibody, particularly a monoclonal antibody or a functional part thereof, or a polynucleotide comprising a nucleic acid sequence encoding said binding peptide or antibody, according to any one of the embodiments described and claimed herein, or a combination thereof, in a therapeutically effective amount together with a pharmaceutically acceptable carrier.

Suitable pharmaceutical carriers, diluents and/or excipients are well known in the art and include, for example, phosphate buffered saline solutions, water, emulsions such as oil/water emulsions, various types of wetting agents, sterile solutions, etc.

The binding peptides according to the invention including antibodies, particularly monoclonal antibodies and active fragments thereof, can be prepared in a physiologically acceptable formulation and may comprise a pharmaceutically acceptable carrier, diluent and/or excipient using known techniques. For example, the binding peptides according to the invention and as described herein including any functionally equivalent binding peptides or functional parts thereof, in particular, the monoclonal antibodies of the invention including any functionally equivalent antibodies or functional parts thereof, are combined with a pharmaceutically acceptable carrier, diluent and/or excipient to form a therapeutic composition. Suitable pharmaceutical carriers, diluents and/or excipients are well known in the art and include, for example, phosphate buffered saline solutions, water, emulsions such as oil/water emulsions, various types of wetting agents, sterile solutions, etc.

Formulation of the pharmaceutical composition according to the invention can be accomplished according to standard methodology know to those of ordinary skill in the art.

The compositions of the present invention may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. In general, the composition may be administered by topical, oral, rectal, nasal, interdermal, intraperitoneal, or parenteral (for example, intravenous, subcutaneous, or intramuscular) routes.

In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

It is well known to those of ordinary skill in the pertinent art that the dosage of the composition will depend on various factors such as, for example, the condition of being treated, the particular composition used, and other clinical factors such as weight, size, sex and general health condition of the patient, body surface area, the particular compound or composition to be administered, other drugs being administered concurrently, and the route of administration.

The composition according to the invention may be administered in combination with other compositions comprising an biologically active substance or compound such as, for example, a known compound used in the medication of tauopathies and/or of amyloidoses, a group of diseases and disorders associated with amyloid or amyloid-like protein such as the amyloid β protein involved in Alzheimer's Disease.

The other biologically active substance or compound may exert its biological effect by the same or a similar mechanism as the therapeutic vaccine according to the invention or by an unrelated mechanism of action or by a multiplicity of related and/or unrelated mechanisms of action.

Generally, the other biologically active compound may include neutron-transmission enhancers, psychotherapeutic drugs, acetylcholine esterase inhibitors, calcium-channel blockers, biogenic amines, benzodiazepine tranquilizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal antiinflammatory drugs, antioxidants, and serotonergic receptor antagonists.

In particular, the biologically active agent or compound may comprise at least one compound selected from the group consisting of compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), secretase activators, [beta]- and 7-secretase inhibitors, tau proteins, neurotransmitter, /3-sheet breakers, antiinflammatory molecules, "atypical antipsychotics" such as, for example clozapine, ziprasidone, risperidone, aripiprazole or olanzapine or cholinesterase inhibitors (ChEIs) such as tacrine, rivastigmine, donepezil, and/or galantamine and other drugs and nutritive supplements such as, for example, vitamin B 12, cysteine, a precursor of acetylcholine, lecithin, choline, Ginkgo biloba, acetyl-L-carnitine, idebenone, propentofylline, or a xanthine derivative, together with a binding peptide according to the invention including antibodies, particularly monoclonal antibodies and active fragments thereof, and, optionally, a pharmaceutically acceptable carrier and/or a diluent and/or an excipient and instructions for the treatment of diseases.

In a further embodiment, the composition according to the invention may comprise niacin or memantine together with a binding peptide according to the invention including antibodies, particularly monoclonal antibodies and active fragments thereof, and, optionally, a pharmaceutically acceptable carrier and/or a diluent and/or an excipient.

In still another embodiment of the invention compositions are provided that comprise "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with the binding peptide according to the invention including antibodies, particularly monoclonal antibodies and active fragments thereof, and, optionally, a pharmaceutically acceptable carrier and/or a diluent and/or an excipient.

Other compounds that can be suitably used in compositions in addition to the binding peptide according to the invention, are those disclosed, for example, in WO 2004/058258 (see especially pages 16 and 17) including therapeutic drug targets (page 36-39), alkanesulfonic acids and alkanolsulfuric acid (pages 39-51), cholinesterase inhibitors (pages 51-56), NMDA receptor antagonists (pages 56-58), estrogens (pages 58-59), non-steroidal antiinflammatory drugs (pages 60-61), antioxidants (pages 61-62), peroxisome proliferators-activated receptors (PPAR) agonists (pages 63-67), cholesterol-lowering agents (pages 68-75); amyloid inhibitors (pages 75-77), amyloid formation inhibitors (pages 77-78), metal chelators (pages 78-79), antipsychotics and anti-depressants (pages 80-82), nutritional supplements (pages 83-89) and compounds increasing the availability of biologically active substances in the brain (see pages 89-93) and prodrugs (pages 93 and 94), which document is incorporated herein by reference, but especially the compounds mentioned on the pages indicated above.

Proteinaceous pharmaceutically active matter may be present in amounts between 1 ng and 10 mg per dose. Generally, the regime of administration should be in the range of between 0.1 µg and 10 mg of the antibody according to the invention, particularly in a range 1.0 µg to 1.0 mg, and more particularly in a range of between 1.0 µg and 100 µg, with all individual numbers falling within these ranges also being part of the invention. If the administration occurs through continuous infusion a more proper dosage may be in the range of between 0.01 µg and 10 mg units per kilogram of body weight per hour with all individual numbers falling within these ranges also being part of the invention.

Administration will generally be parenterally, e.g. intravenously or subcutaneously. Preparations for parenteral administration include sterile aqueous or non-aqueous solutions, suspensions and emulsions. Non-aqueous solvents include, without being limited to, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, antioxidants, chelating agents, inert gases, etc.

The pharmaceutical composition may further comprise proteinaceous carriers such as, for example, serum albumin or immunoglobulin, particularly of human origin. Further biologically active agents may be present in the pharmaceutical composition of the invention dependent on its the intended use.

When the binding target is located in the brain, certain embodiments of the invention provide for the binding peptide according to the invention including antibodies, particularly monoclonal antibodies and active fragments thereof, to traverse the blood-brain barrier. Certain neurodegenerative diseases are associated with an increase in permeability of the blood-brain barrier, such that the binding peptide according to the invention including antibodies, particularly monoclonal antibodies or active fragment thereof can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the binding peptide according to the invention including antibodies, particularly monoclonal antibodies, or active fragment thereof across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., Gene Therapy 9: 398-406 (2002)) and implanting a delivery device in the brain (see, e.g., Gill et al., Nature Med. 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Vols 1 & 2, Plenum Press, N.Y. (1989)), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the binding peptide or antigen-binding fragment (see, e.g., U.S. Patent Publication No. 2003/0083299).

Lipid-based methods of transporting the binding peptide according to the invention including antibodies, particularly monoclonal antibodies, or an active fragment thereof across the blood-brain barrier include, but are not limited to, encapsulating the binding peptide according to the invention including antibodies, particularly monoclonal antibodies, or active fragment thereof in liposomes that are coupled to active fragments thereof that bind to receptors on the vascular endothelium of the blood-brain barrier (see, e.g., U.S. Patent Application Publication No. 20020025313), and coating the binding peptide according to the invention including antibodies, particularly monoclonal antibodies, or active fragment thereof in low-density lipoprotein particles (see, e.g., U.S. Patent Application Publication No. 20040204354) or apolipoprotein E (see, e.g., U.S. Patent Application Publication No. 20040131692).

Receptor and channel-based methods of transporting the binding peptide according to the invention including antibodies, particularly monoclonal antibodies, or active fragment thereof across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

Single or repeated administrations of the binding peptide according to the invention including antibodies, particularly monoclonal antibodies, or an active fragment thereof, or of a pharmaceutical composition according to the invention may be provided to a subject over an extended period of time. The duration of administration may be between 1 week and up to 12 month or more. During this time the binding peptide, antibody or pharmaceutical composition may be administered once a week, once every two weeks, three weeks, four weeks, etc, or at a higher or lower frequency depending on the needs of the subject to be treated.

In a further embodiment the present invention provides methods and kits for the detection and diagnosis of tau-protein-associated diseases, disorders or conditions, including neurodegenerative diseases or disorders such as tauopathies comprising a heterogeneous group of neurodegenerative diseases or disorders including diseases or disorders which manifest both tau and amyloid pathologies including, but not limited to, Alzheimer's Disease, Creutzfeldt-Jacob disease, Dementia pugilistica, Down's Syndrome, Gerstmann-Sträussler-Scheinker disease, inclusion-body myositis, and prion protein cerebral amyloid angiopathy, traumatic brain injury and further of diseases or disorders which do not show a distinct amyloid pathology including, but not limited to, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia with parkinsonism linked to chromosome 17, Hallevorden-Spatz disease, multiple system atrophy, Niemann-Pick disease, type C, Pallido-ponto-nigral degeneration, Pick's disease, progressive subcortical gliosis, progressive supranuclear palsy, Subacute sclerosing panencephalitis Tangle-only dementia, Postencephalitic Parkinsonism, Myotonic dystrophy. The pathological abnormalities may be caused by or associated with the formation of neurofibrillary lesions, the predominant brain pathology in tauopathy.

Further, the present invention provides methods and kits for diagnosing a predisposition to tau-protein-associated diseases, disorders or conditions, including neurodegenerative diseases or disorders such as tauopathies comprising a heterogeneous group of neurodegenerative diseases or disorders including diseases or disorders which show co-manifest both tau and amyloid pathologies, or for monitoring minimal residual disease in a patient or for predicting responsiveness of a patient to a treatment with a binding peptide according to the invention including antibodies, particularly monoclonal antibodies and active fragments thereof, or a composition according to the invention and as described herein. These methods include known immunological methods commonly used for detecting or quantifying substances in biological samples or in an in situ condition.

Diagnosis of a tau-protein-associated disease or condition or of a predisposition to an tau-protein-associated disease or condition in a subject in need thereof, particularly a mammal, more particularly a human, including neurodegenerative diseases or disorders such as tauopathies comprising a heterogeneous group of neurodegenerative diseases or disorders including diseases or disorders which manifest both of tau and amyloid pathologies, may be achieved by detecting the immunospecific binding of a binding peptide of the invention, particularly of an antibody, particularly of a monoclonal antibody or an active fragment thereof, to an epitope of the tau protein in a sample or in situ, which includes bringing the sample or a specific body part or body area suspected to contain the tau protein into contact with an antibody which binds an epitope of the tau protein, allowing the antibody to bind to the tau protein to form an immunologic complex, detecting the formation of the immunologic complex and correlating the presence or absence of the immunologic complex with the presence or absence of tau protein in the sample or specific body part or area, optionally comparing the amount of the immunologic complex to a normal control value, wherein an increase in the amount of the immunologic complex compared to a normal control value indicates that the subject is suffering from or is at risk of developing an tau protein-associated disease or condition.

Monitoring minimal residual disease in a subject, particularly a mammal, more particularly a human, following treatment with a binding peptide according to the invention including antibodies, particularly monoclonal antibodies and active fragments thereof, or a composition according to the invention may be achieved by detecting the immunospecific binding of a binding peptide of the invention, particularly of an antibody, particularly a monoclonal antibody or an active fragment thereof to an epitope of the tau protein in a sample or in situ, which includes bringing the sample or a specific body part or body area suspected to contain the tau protein into contact with a binding peptide according to the invention including antibodies, particularly monoclonal antibodies and active fragments thereof, which binds an epitope of the tau protein, allowing the binding peptide according to the invention including antibodies, particularly monoclonal antibodies and active fragments thereof, to bind to the tau protein to form an immunologic complex, detecting the formation of the immunologic complex and correlating the presence or absence of the immunologic complex with the presence or absence of tau protein in the sample or specific body part or area, optionally comparing the amount of said immunologic complex to a normal control value, wherein an increase in the amount of said immunologic complex compared to a normal control value indicates that the subject may still suffer from a minimal residual disease.

Predicting responsiveness of a subject, particularly a mammal, more particularly a human, to a treatment with a binding peptide according to the invention including antibodies, particularly monoclonal antibodies and active fragments thereof, or a composition according to the invention may be achieved by detecting the immunospecific binding of a binding peptide, particularly of a monoclonal antibody or an active fragment thereof to an epitope of the tau protein in a sample or in situ, which includes bringing the sample or a specific body part or body area suspected to contain the tau protein into contact with a binding peptide according to the invention including antibodies, particularly monoclonal antibodies and active fragments thereof, which binds an epitope of the tau protein, allowing the binding peptide according to the invention including antibodies, particularly monoclonal antibodies and active fragments thereof, to bind to the tau protein to form an immunologic complex, detecting the formation of the immunologic complex and correlating the presence or absence of the immunologic complex with the presence or absence of tau protein in the sample or specific body part or area, optionally comparing the amount of said immunologic complex before and after onset of the treatment, wherein an decrease in the amount of said immunologic complex indicates that said patient has a high potential of being responsive to the treatment.

Biological samples that may be used in the diagnosis of a tau protein-associated disease or condition, for diagnosing a predisposition to a tau protein-associated disease or condition, including neurodegenerative diseases or disorders such as tauopathies comprising a heterogeneous group of neurodegenerative diseases or disorders including diseases or disorders which manifest both tau and amyloid pathologies, or for monitoring minimal residual disease in a patient or for predicting responsiveness of a patient to a treatment with a binding peptide according to the invention including antibodies, particularly monoclonal antibodies and active fragments thereof, or a composition according to the invention and as described herein are, for example, fluids such as serum, plasma, saliva, gastric secretions, mucus, cerebrospinal fluid, lymphatic fluid and the like or tissue or cell samples obtained from an organism such as neural, brain, cardiac or vascular tissue. For determining the presence or absence of the tau protein in a sample, any immunoassay known to those of ordinary skill in the art may be used such as, for example, assays which utilize indirect detection methods using secondary reagents for detection, ELISA's and immunoprecipitation and agglutination assays. A detailed description of these assays is, for example, given in Harlow and Lane, Antibodies: A Laboratory Manual (Cold Spring Harbor Laboratory, New York 1988 555-612, WO96/13590 to Maertens and Stuyver, Zrein et al. (1998) and WO96/29605.

For in situ diagnosis, the binding peptide according to the invention including antibodies, particularly monoclonal antibodies and active fragments thereof, of the invention or any active and functional part thereof may be administered to the organism to be diagnosed by methods known in the art such as, for example, intravenous, subcutaneous, intranasal, intraperitoneal, intracerebral, intraarterial injection such that a specific binding between an antibody according to the invention with an eptitopic region on the amyloid protein may occur. The binding peptide/antigen complex may conveniently be detected through a label attached to the binding peptide according to the invention including antibodies, particularly monoclonal antibodies, or a functional fragment thereof or any other art—known method of detection.

The immunoassays used in diagnostic applications or in applications for diagnosing a predisposition to a tau protein-associated disease or condition, including neurodegenerative diseases or disorders such as tauopathies comprising a heterogeneous group of neurodegenerative diseases or disorders including diseases or disorders which manifest both tau and amyloid pathologies, or for monitoring minimal residual disease in a patient or for predicting responsiveness of a patient to a treatment with a binding peptide according to the invention including antibodies, particularly monoclonal antibodies and active fragments thereof, or a composition according to the invention and as described herein typically rely on labelled antigens, binding peptides, or secondary reagents for detection. These proteins or reagents can be labelled with compounds generally known to those of ordinary skill in the art including enzymes, radioisotopes, and fluorescent, luminescent and chromogenic substances including, but not limited to colored particles, such as colloidal gold and latex beads. Of these, radioactive labelling can be used for almost all types of assays and with most variations. Enzyme-conjugated labels are particularly useful when radioactivity must be avoided or when quick results are needed. Fluorochromes, although requiring expensive equipment for their use, provide a very sensitive method of detection. Binding peptides useful in these assays are those disclosed claimed herein including antibodies, particularly monoclonal antibodies, polyclonal antibodies, and affinity purified polyclonal antibodies.

Alternatively, the binding peptide according to the invention including antibodies, particularly monoclonal antibodies and active fragments thereof, may be labelled indirectly by reaction with labelled substances that have an affinity for immunoglobulin, such as protein A or G or second antibodies. The binding peptide according to the invention including antibodies, particularly monoclonal antibodies and active fragments thereof, may be conjugated with a second substance and detected with a labelled third substance having an affinity for the second substance conjugated to the antibody. For example, the binding peptide according to the invention including antibodies, particularly monoclonal antibodies and active fragments thereof, may be conjugated to biotin and the binding peptide/biotin conjugate detected using labelled avidin or streptavidin. Similarly, the binding peptide may be conjugated to a hapten and the binding peptide/hapten conjugate detected using labelled anti-hapten binding peptide.

Those of ordinary skill in the art will know of these and other suitable labels which may be employed in accordance with the present invention. The binding of these labels to binding peptides or fragments thereof can be accomplished using standard techniques commonly known to those of ordinary skill in the art. Typical techniques are described by Kennedy, J. H., et al., 1976 (Clin. Chim. Acta 70:1-31), and Schurs, A. H. W. M., et al. 1977 (Clin. Chim Acta 57:1-40). Coupling techniques mentioned in the latter are the glutaraldehyde method, the periodate method, the dimaleimide method, and others, all of which are incorporated by reference herein.

Current immunoassays utilize a double antibody method for detecting the presence of an analyte, wherein, the antibody is labeled indirectly by reactivity with a second antibody that has been labeled with a detectable label. The second antibody is preferably one that binds to antibodies of the animal from which the monoclonal antibody is derived. In other words, if the monoclonal antibody is a mouse antibody, then the labeled, second antibody is an anti-mouse antibody. For the antibody to be used in the assay described herein, this label is preferably an antibody-coated bead, particularly a magnetic bead. For the antibody to be employed in the immunoassay described herein, the label is preferably a detectable molecule such as a radioactive, fluorescent or an electrochemiluminescent substance.

An alternative double antibody system, often referred to as fast format systems because they are adapted to rapid determinations of the presence of an analyte, may also be employed within the scope of the present invention. The system requires high affinity between the antibody and the analyte. According to one embodiment of the present invention, the presence of the amyloid protein is determined using a pair of antibodies, each specific for amyloid protein. One of said pairs of antibodies is referred to herein as a "detector antibody" and the other of said pair of antibodies is referred to herein as a "capture antibody". The monoclonal antibody of the present invention can be used as either a capture antibody or a detector antibody. The monoclonal antibody of the present invention can also be used as both capture and detector antibody, together in a single assay. One embodiment of the present invention thus uses the double antibody sandwich method for detecting amyloid protein in a sample of biological fluid. In this method, the analyte (amyloid protein) is sandwiched between the detector antibody and the capture antibody, the capture antibody being irreversibly immobilized onto a solid support. The detector antibody would contain a detectable label, in order to identify the presence of the antibody-analyte sandwich and thus the presence of the analyte.

Exemplary solid phase substances include, but are not limited to, microtiter plates, test tubes of polystyrene, magnetic, plastic or glass beads and slides which are well known in the field of radioimmunoassay and enzyme immunoassay. Methods for coupling antibodies to solid phases are also well known to those of ordinary skill in the art. More recently, a number of porous material such as nylon, nitrocellulose, cellulose acetate, glass fibers and other porous polymers have been employed as solid supports.

The present invention also relates to a diagnostic kit for detecting tau protein in a biological sample comprising a composition as defined above. Moreover, the present invention relates to the latter diagnostic kit which, in addition to a composition as defined above, also comprises a detection reagent as defined above. The term "diagnostic kit" refers in general to any diagnostic kit known in the art. More specifically, the latter term refers to a diagnostic kit as described in Zrein et al. (1998).

It is still another object of the present invention to provide novel immunoprobes and test kits for detection and diagnosis of tau protein-associated diseases and conditions, comprising binding peptides according to the present invention. For immunoprobes, the binding peptides are directly or indirectly attached to a suitable reporter molecule, e.g., an enzyme or a radionuclide. The test kit includes a container holding one or more binding peptides according to the present invention and instructions for using the binding peptides for the purpose of binding to tau antigen to form an immunologic complex and detecting the formation of the immunologic complex such that presence or absence of the immunologic complex correlates with presence or absence of tau protein.

EXAMPLES

Example 1

Generation and Screening of Hybridomas and Antibodies

The objective of this study was to generate and screen anti-Tau mAbs (monoclonal antibodies). Hybridomas were generated by fusion of tau vaccine immunized mouse spleen cells with a myeloma cell line. The hybridomas were assessed for reactivity against both phosphorylated and non-phosphorylated full-length Tau protein, as well as the phosphorylated and non-phosphorylated Tau antigenic peptides used in the vaccine preparation. Hybridoma screening was also performed for reactivity of hybridomas supernatant for tau tangles using immunochemistry on Tau transgenic mouse brain slices.

1.1 Methods 1.1.1 Fusion

A wild type C57BL/6 mouse vaccinated with ACI-35 (Tau393-408 [pS396, pS404]) was used for hybridoma production. The mouse was boosted with ACI-35 vaccine on day 0 then again on day 4 and the fusion was performed on day 7.

$6 \times 10^7$ (ACI-35), splenocytes from the immunized mouse were fused with $2 \times 10^7$ SP2-O-Ag14 myeloma cells at a ratio of 3 splenocytes/1 myeloma cell.

The fusions resulted in 8×96 well plates and the clones were named according to the plate (1-8) then the row (A-G) and finally the column (1-12).

1.1.2 Screening Method to Select Clones

The 8×96 well plates were first screened twice for IgG expression. Positive expressing clones were then transferred in 24 well plates and cell supernatants (=clones) of growing cells were tested in a Tau ELISA screen and a immunohistochemistry TAUPIR screen. Positive supernatants in ELISA and/or TAUPIR were transferred to T25 flasks and clones were screened again for IgG expression in a Tau ELISA screen and TAUPIR screen.

1.1.3 IgG Screen

ELISA plates (Costar; Sigma) were coated with 50 µl/well of anti-mouse IgG antibody (AbD Serotec, Düsseldorf, Germany) in coating buffer for 16 hr at 4° C. After washing plates with PBS/TWEEN®, wells were blocked with 100 µl/well of blocking solution for 1 hr at ambient temperature. Undiluted hybridoma supernatants (50 µl per well) were incubated for 1 hr at ambient temperature. After a washing, a mix of horseradish peroxidase (HRP)-conjugated anti-mouse IgG1, IgG2a, IgG2b, IgG3, or IgM (AbD Serotec) was applied for 1 hr at ambient temperature. After a final wash, detection was performed with HRP substrate (TMB; 3-3',5,5'-tetramethylbenzidine), and plates were read at 405 nm using a microplate reader. Results are expressed as optical density (O.D.).

1.1.4 Hybridomas Tau ELISA Screen

Hybridomas ELISA screen was performed on pTau peptide (ACI-35, T3.5: Tau393-408[pS396/pS404; PolyPeptide Laboratories, Hillerød, Denmark), the corresponding non-phosphorylated Tau peptide (T3.6: Tau393-408, PolyPeptide Laboratories), phosphorylated full-length (441aa) Tau protein (pTau protein, Vandebroek et al., 2005) and full-length (441aa) Tau protein (Tau protein, SignalChem, Richmond, Canada). Finally Bovine Serum Albumin (BSA) was used as negative control.

Plates were coated with 10 µg/ml of corresponding Tau peptide and 1 µg/ml of corresponding Tau protein overnight at 4° C. After washing each well with PBS-0.05% TWEEN® 20 and blocking with 1% BSA in PBS-0.05% TWEEN® 20, undiluted hybridoma supernatant or medium negative control were added to the plates and incubated at 37° C. for 2 hours. After washing plates were incubated with an alkaline phosphatase (AP)-conjugated anti-mouse IgG total antibody (Jackson Laboratories, Baltimore, Pa., USA) for 2 hours at 37° C. After washing plates were incubated with pNPP (para-nitro-phenyl-phosphate), the phosphatase substrate for AP, and read at 405 nm using an ELISA plate reader. Results are expressed as O.D. (Optical Density).

1.1.5 Hybridomas IHC Screen: Binding of Anti-Tau Antibodies to Tangles in Brain Sections from Transgenic Mice (TAUPIR)

TAUPIR experiments were done according to protocol from EXAMPLE 3.1.2.

1.1.6 T25 Flasks IgG Screen

ELISA plates were coated with 5 ug/ml of anti-mouse IgG F(ab')2 fragment specific antibody (Jackson Laboratories, Baltimore, Pa., USA) in carbonate-bicarbonate coating buffer pH 9.6 (Sigma, Buchs, Switzerland) overnight at 4° C. After washing plates, undiluted hybridoma supernatant, positive control IgG1 antibody (6E10 at 1 ug/ml; Covance, Emeryville, Calif., USA) or negative control (culture medium alone) were incubated for 1 hr at RT. After a washing step, the secondary AP-conjugated goat anti-mouse IgG (subclasses 1+2a+2b+3) Fcγ fragment specific antibody (Jackson Laboratories, Baltimore, Pa., USA) was incubated on the plates for 2 hrs at 37° C. After a final washing, detection was performed with pNPP (para-nitro-phenyl-phosphate), the phosphatase substrate for AP, and plates were read at 405 nm using an ELISA plate reader. Results are expressed as O.D. (Optical Density).

1.2 Results

The cell supernatants from the 8×96 well plates resulting from the fusion were screened for production of IgG. Out of 768 wells (8×96 wells) tested, 48 wells positive for IgG production were selected based on the best binding to the vaccine phospho-peptide, and to full-length phospho-Tau. Selection was based on binding to the peptide and full-length phospho-Tau protein by ELISA, and also to selectivity when comparing to non-phospho-peptide and non-phospho full-length Tau protein. 24 selected hybridomas were subcloned by seeding 2 plates per hybridoma at 1 cell/well and 1 plate at 0.5 cell/well. Supernatants were tested again for binding to phospho-peptide and phospho-protein to verify binding profile, after which stability was evaluated in a 6-week culture. Eight stable clones were then selected and tested for isotyping, and binding using ELISA and TAUPIR as described in Methods.

1.3. Conclusion

The antibodies generated have shown high specificity to pTau peptides with only marginal binding to non-phosphorylated peptides.

A total of 8 clones were selected for further subcloning and were sequenced (see Table 6 and Table 7) and 6 clones were deposited at DSMZ (see Table 10).

The positive mother clones mentioned above were further cultivated in 96 well plates, then 24 well plates and finally T25 flasks. At each stage, the supernatants of the hybridoma clones were screened by ELISA, Taupir and Western Blot.

Example 2

Cloning of Antibody Light Chain and Heavy Chain Variable Regions

Antibody heavy and light variable region genes from the hybridoma cells are cloned and the DNA sequences and location of the complementarity determining regions (CDRs) determined as well as the antibodies binding features.

Total RNA was prepared from $3 \times 10^6$ hybridoma cells (1 vial) using the (Jiagen RNeasy mini kit (Cat No: 74104). RNA was eluted in 50 uL water and checked on a 1.2% agarose gel.

$V_H$ and $V_K$ cDNAs were prepared using reverse transcriptase with IgG and kappa constant region primers. The first strand cDNAs were amplified by PCR using a large set of signal sequence primers. The amplified DNAs were gel-purified and cloned into the vector pGem® T Easy (Promega). The $V_H$ and $V_K$ clones obtained were screened for inserts of the expected size. The DNA sequence of selected clones was determined in both directions by automated DNA sequencing. The locations of the complementarity determining regions (CDRs) in the sequences were determined with reference to other antibody sequences (Kabat E A et al., 1991).

Example 3

Binding Studies I

The objective was to measure the phospho-Tau (pTau) binding of the antibodies generated from subcloned hybridomas derived from mice immunized with the tau liposomal vaccines. To test this, an enzyme-linked immunosorbant assay (ELISA) was used to measure the binding of the purified antibodies to both phosphorylated and non-phosphorylated full-length Tau protein, as well as the phosphorylated and non-phosphorylated Tau antigenic peptides used for the liposomal vaccine preparation.

The screening was completed by two other methods. Immunohistochemistry (IHC) on brain sections from a Tau transgenic animal (TAUPIR) using an anti-tau antibody as the primary antibody was done. Additionally, a western blot (WB) on brain protein homogenates from Tau transgenic mice was performed, using an anti-tau antibody as the blotting antibody.

3.1 Methods 3.1.1. ELISAs: Phospho-Tau Binding Assay

To test the binding of the purified antibodies to Tau and pTau, an ELISA assay was used. Briefly, Nunc Maxi Sorp 96-well plates (Nunc, Roskilde, Denmark) were coated with 1 µg/mL of full-length (441 aa) Tau protein (SignalChem, Richmond, Canada) or phosphorylated full-length (441 aa) Tau protein (Vandebroek et al., 2005). Additionally, plates were coated with 10 µg/mL of the Tau-derived vaccine peptide, Tau393-408 (phosphorylated or not on S396 and S404). To test for cross-reactivity to Tau and pTau sequences of different pTau epitopes that were not used in the vaccine preparation, plates were coated with 10 µg/mL of the following peptides: Tau393-408 (phosphorylated or not on S396 and S404), Coating was done overnight in phosphate-buffered saline (PBS) at 4° C. Plates were washed thoroughly with 0.05% TWEEN®20/PBS and then blocked with 1% bovine serum albumin (BSA) in 0.05% TWEEN®20/PBS for 1 hr at 37° C. The antibody being tested was then added in an 8 or 16 two-fold dilution series between 20 and 0 µg/mL, and allowed to incubate for 2 hr at 37° C. Plates were then washed as described previously, and AP-conjugated anti-mouse IgG secondary antibody (Jackson ImmunoResearch Laboratories, Suffolk, England) was added at 1/6000 dilution in 0.05% TWEEN®20/PBS for 2 hr at 37° C. After washing, plates were incubated with p-nitrophenyl phosphate disodium hexahydrate (pNPP; Sigma-Aldrich, Buchs, Switzerland) phosphatase substrate solution, and read at 405 nm following 30 min, 1, 2 or 16 hr incubation times using an ELISA plate reader.

3.1.2. TAUPIR and Western-Blots: Binding of Anti-Tau Antibody to Tau Tangles in Brain Sections from a Tau Transgenic Animal (TAUPIR)

For TAUPIR staining, brain sections were from TPLH mice (transgenic mice expressing the longest isoform (441aa) of hTau$^{P301L}$), old (>18 months old) double transgenic biGT (GSK-3β transgenic mice crossed with TPLH) mice, and double transgenic biAT (hAPP$^{V717I}$ transgenic mice crossed with TPLH) mice. As a negative control, sections from Tau knock-out mice (TKO; 6 months old) were used. Brain sections were washed for 5 min in PBS then incubated for 15 min at RT in 1.5% $H_2O_2$ in PBS:MeOH (1:1) to block endogenous peroxidase activity. After washing the sections 3 times in PBST (PBS/0.1% TRITON™ X-100) they were incubated for 30 min at RT in PBST+10% FCS (fetal calf serum) blocking solution. The incubation with the anti-Tau antibody being tested was done overnight at 4° C. using the following antibody concentrations: ACI-35-2A1-Ab1 at 0.0053 µg/mL, ACI-35-2A1-Ab2 at 0.0048 µg/mL, ACI-35-4A6-Ab1 at 0.015 µg/mL, ACI-35-1D2-Ab1 at 0.0047 µg/mL, ACI-35-2G5-Ab1 at 0.0055 µg/mL, and ACI-35-2G5-Ab2 and ACI-35-2G5-Ab3 at 0.01 µg/mL in PBST/10% FCS. Sections were next washed 3 times in PBST before incubation with an HRP-conjugated goat anti-mouse (purchased from Dako, Glostrup, Denmark) secondary antibody in PBST/10% FCS for 1 hour at RT. Prior to detection, sections were washed 3 times with PBST and incubated in 50 mM Tris/HCl pH7.6 for 5 min. Detection was done by incubating the sections for 3 min in Diaminobenzidine (DAB: 1 tablet in 10 ml of 50 mM Tris.HCl+3 µl $H_2O_2$ 30%; MP Biomedicals, Solon, Ohio, USA). The reaction was stopped by washing the sections 3 times in PBST. Sections were then transferred onto silanized glass-plates and air-dried on warm-plate at 50° C. for 2 hours. Counterstaining was done using incubation with Mayers hematoxylin (Fluka Chemie, Buchs, Switzerland) for 1 min, followed by a washing step for 4 min in running tap-water. Sections were dehydrated by passing in 50%, 70%, 90% and twice in 100% ethanol bath then in Xylol 2 times for 1 min. Finally sections were mounted with DePeX (BDH Chemicals Ltd., Poole, England) under glass coverslips for imaging.

Additional staining (Western-blotting) was done on SDS-PAGE (10%) separated brain homogenate proteins from wild-type mice (FVB) Tau transgenic mice (TPLH and biGT), or Tau knock-out mice (TKO). For Western-blotting, antibodies were used at the following concentrations: ACI-35-2A1-Ab1 at 0.53 µg/mL, ACI-35-2A1-Ab2 at 0.48 µg/mL, ACI-35-4A6-Ab1 at 0.5 µg/mL, ACI-35-1D2-Ab1 at 0.47 µg/mL, ACI-35-2G5-Ab1 at 0.55 µg/mL, ACI-35-2G5-Ab2 at 0.33 µg/mL, and ACI-35-2G5-Ab3 at 0.5 µg/mL.

3.2 Results

Antibody ACI-35-2A1-Ab1, ACI-35-2A1-Ab2, ACI-35-1D2-Ab1, ACI-35-2G5-Ab2 and ACI-35-2G5-Ab3 demonstrated high binding activity and specificity to phosphorylated human Tau protein (Table 2), more specifically to the antigenic phospho-Tau peptide used in the corresponding vaccine. No cross-reactivity to non-phosphorylated Tau was observed, or to other phosphorylated and non-phosphorylated Tau-derived peptides tested. Antibody ACI-35-4A6-Ab1, as per its selection, displayed high binding activity only to the antigenic phospho-Tau peptide used in the vaccine preparation. Low cross-reactivity was found to the non-phospho counterpart of the antigenic peptide used in the vaccine preparation which was expected based on the clone selection. Antibody ACI-35-2G5-Ab1, displayed high binding activity only to the antigenic phospho-Tau peptide used in the vaccine preparation. Small cross-reactivity was observed to the T4.5 phospho-peptide, comprising part of the antigenic peptide sequence used in the vaccine.

TAUPIR and WBs were used to look at binding to Tau tangles in brains of mice with advanced tauopathy (biGT>18 months), and to full-length Tau in denatured homogenates derived from these mice. Different brain regions were analyzed: cortex and CA1. CA3 and dentate gyrus (DG) part of the hippocampus. Antibodies ACI-35-2A1-Ab1 and ACI-35-2A1-Ab2 displayed the best TAUPIR results with a dense cytoplasmic staining and clear neuropil threads, especially in the CA1 and CA3 regions of the hippocampus. Antibody ACI-35-4A6-Ab1 was negative in TAUPIR with only faint sporadic tangle like structures lightly stained. Antibody ACI-35-1D2-Ab1 showed a good cytoplasmic TAUPIR staining with neuropil threads in the CA1 region. Antibody ACI-35-2G5-Ab1 was negative in TAUPIR with nuclear staining and only some tangle staining. Finally. ACI-35-2G5-Ab2 and ACI-35-2G5-Ab3 antibodies displayed similar good cytoplasmic TAUPIR staining with neuropil threads observed in the CA1 and CA3 of the hippocampus. The rating of staining quality using + or – signs is shown in Table 2. Brain homogenates from Tau transgenic mice were blotted, showing that all antibodies bound well to expected Tau bands (Table 2, rated as +), with ACI-35-1D2-Ab1 and ACI-35-2G5-Ab1 also showing additional non-specific binding (–/+).

Example 4

Binding Studies II 4.1 Methods 4.1.1 SPR Binding Assay

All SPR experiments were carried out on a Biacore X instrument (GE Healthcare). Sensor chip SA (Streptavidin derivatized carboxymethyl dextran) was purchased from GE Healthcare. Running buffer was PBS (Dulbecco's PBS, Sigma D8537). Non-covalently bound Streptavidin was firstly removed from the sensor surface by injecting 8 pulses (each ~1 µL) of 16 mM NaOH (aq). Phospho-tau peptide was then solubilized in PBS to give a final peptide concentration of 1 µM and then injected (35 µL) over flow cell (fc) 2 of the sensor chip at 5 µl/min. After coupling, a final immobilization level of 130 RUs was obtained. To study the binding of the antibodies to the chip surface, several concentrations of antibodies were prepared by serial 2-fold dilutions with running buffer. The injections were performed over both fc 1 and 2 at a flow rate of 50 µL/min for 120 s. Flow cell 1 was not derivatized and responses of fc 1 were subtracted from fc 2 to correct for instrument noise and bulk refractive changes. After each injection, the surfaces were washed immediately with running buffer for 100 s. To remove any remaining bound antibody from the chip, surface regeneration was performed by injecting 1 µL of 10 mM Glycine-HCl pH 1.7. Kinetic analyses were performed using algorithms for numerical integration and global analysis using BIAevaluation 3.0. The sensograms obtained for injections of antibody at different concentrations were overlaid and the baselines adjusted to zero. For curve fitting, all data were fit simultaneously to a 1:1 homogeneous (Langmuir) model.

| Peptides used | | |
|---|---|---|
| T3.30 | Biotin-LC linker-GVYKS[PO3H2]PVVSGDTS[PO3H2]PRHL-NH2 (SEQ ID NO: 222) | lot MI89P9-P12-2 (64% pure) lot MI89P9-P12-3 (87% pure) |

4.2 Results

The binding of the anti-tau antibodies to the phosphorylated Tau peptide was monitored in real-time using SPR. Analyses of the association and dissociation phases of antibody binding could be used to determine the association rate constant ($k_a$), dissociation rate constant ($k_d$) as well as dissociation constant $K_D$.

All antibodies were found to bind specifically to peptide T3.30 over the non-derivatized carboxymethyl dextran surface in the range 46→734 nM of antibody analyzed (or 11.5→184 nM for ACI-35-4A6-Ab1). Kinetic analyses of the sensograms revealed the dissociation constant $K_D$ for the binding interaction between the different antibodies and T3.30 to be between 2 and 82 nM. This therefore demonstrates that the antibodies recognize the phosphopeptide T3.30 with very high affinity (Table 3).

Example 5

Binding Studies III ELISA on Human Brain Samples (ELISA for Detection of Multimers of Phosphorylated Tau)

5.1 Methods 5.1.1. Human Samples: Preparation of Human Brain Samples Used for the Assays Described Here Temporal post-mortem cortex for ten Alzheimer's disease (AD) and ten age-matched controls were obtained from the Brain Endowment Bank of the University of Miami. The mean age at death for the AD patients (seven females, three males) was 81.1±7.3 years and for the controls (free of neurological symptoms; nine females, one male) was 87.0±5.8 (not significantly different from the AD patients by student t-test). All samples were of Caucasian origin. The AD samples were characterized for Braak disease stage (Braak and Braak (1991) Neuropathological staging of Alzheimer-related changes. Acta Neuropathol 82:239-259) as shown in Table 4.

Temporal post-mortem cortex for ten AD and ten age-matched controls were homogenized according to the following protocol. Brain fragments were weighted and homogenized in 9 volumes of 25 mM Tris-HCl pH 7.4, 150 mM NaCl, 1 mM EDTA, 1 mM EGTA containing phosphatase inhibitors (30 mM NaF, 0.2 mM Na3VO4, 1 nM okadaic acid, 1 mM PMSF, 5 mM Na4P2O7) and protease inhibitors (Complete Mini; Roche, Switzerland). Homogenization was done on ice using a glass potter. This constitutes the Total Homogenate fraction (TH). Protein concentrations were measured using Bradford reagent (Sigma).

5.1.2. Setup 1 ELISA: Setup 1 ELISA Assay to Detect the Presence of Multimers of Phosphorylated Tau in Human Post-Mortem Cortical Brain Homogenates from AD-Affected Individuals and Age-Matched Controls Multititer 96-well plates were coated with antibodies overnight at 4° C. at 5 µg/ml in carbonate/bicarbonate buffer. After 4 washes in PBS-TWEEN®, plates were saturated with PBS-TWEEN® 10% BSA for 1 hr at 37° C. Brain homogenates were then added to the wells at a concentration of 100 ng/µL in 50 µL PBS, and incubated for 2 hr at 37° C. After washing the plates, the same antibody as used for coating, but biotinylated, was incubated for 1 hr at 37° C. at a final concentration of 5 µg/mL. Plates were washed and after addition of avidin-peroxydase (Vectastain ABC kit, Vector Laboratories) and its substrate (ABTS, Roche 10881420) the plates were read at different time points. Values are expressed as mean OD±SD for 10 AD and 10 control subjects.

5.2 Results

Antibodies ACI-35-2A1-Ab1 and ACI-35-2G5-Ab3 were tested for their ability to detect phosphoTau (pTau) multimers in brain homogenates from AD and control subjects, using a phospho- and multimer-specific Setup 1 ELISA. We observed a highly significant (p<0.001) difference between AD and age-matched controls (n=10) in this assay for both antibodies (FIG. 1). Using human post-mortem cortical homogenates from AD and age-matched control brain, we demonstrated the ability of ACI-35-2A1-Ab1 and ACI-35-2G5-Ab3 anti-pTau antibodies to detect multimers of Tau-pS396 in post-mortem human brain samples.

Example 6

Binding Studies IV—Western-Blots on Human Brain Samples 6.1 Methods 6.1.1. Human Samples: The Same Method for Preparation of Human Samples as Described in Method 5.1.1.

6.1.2. Western-Blots: Western-Blot Assay to Detect the Presence of Phosphorylated Tau in Human Post-Mortem Cortical Brain Homogenates from AD-Affected Individuals and Age-Matched Controls The anti-human Tau antibodies used in this study were the mouse ACI-35-2A1-Ab1, ACI-35-1D2-Ab1, and ACI-35-2G5-Ab3, all directed against Tau-pS396. The mouse monoclonal TAU-13 antibody (Abcam ab24636) directed against total human Tau, and the rabbit monoclonal antibody E178 directed against Tau-pS396 (Abcam ab32057) were used as controls. 20 µg of each total homogenate was loaded per lane of on a 10% polyacrylamide Bis-TRIS precast gel (NUPAGE® NOVEX® 10% Bis-TRIS Midi Gel, Invitrogen). Proteins were resolved as recommended by the manufacturer in NUPAGE® MOPS SDS running buffer (Invitrogen NP0001). Protein blotting was done for 3 hr in 25 mM TRIS pH 8.6, 190 mM Glycin buffer, 20% methanol, on ice on PVDF membranes (Immobilon-FL, Millipore IPFL00010).

Membranes were blocked for 1 hr in LICOR® blocking buffer (Odyssey) diluted ⅓ in PBS. Membranes were incubated overnight with primary antibodies at the following concentrations: TAU-13 at 0.6 μg/mL, E178 diluted 1/5000, ACI-35-2A1-Ab1 at 0.53 μg/mL, ACI-35-1D2-Ab1 at 0.47 μg/mL, and ACI-35-2G5-Ab3 at 0.5 μg/mL, diluted ⅓ in LICOR® buffer and ⅔ PBS with 0.1% 20 TWEEN® 20 (PBS-T). After 4 washes in PBS-T, membranes were incubated with a goat anti-mouse antibody coupled with the LICOR® 800 dye (Goat anti-mouse IRDYE® 800 CW, Odyssay) for 1 hr at room temperature, washed again 4 times with PBS-T, and scanned for image reproduction using the LICOR® system.

6.2 Results

Figure 2A:
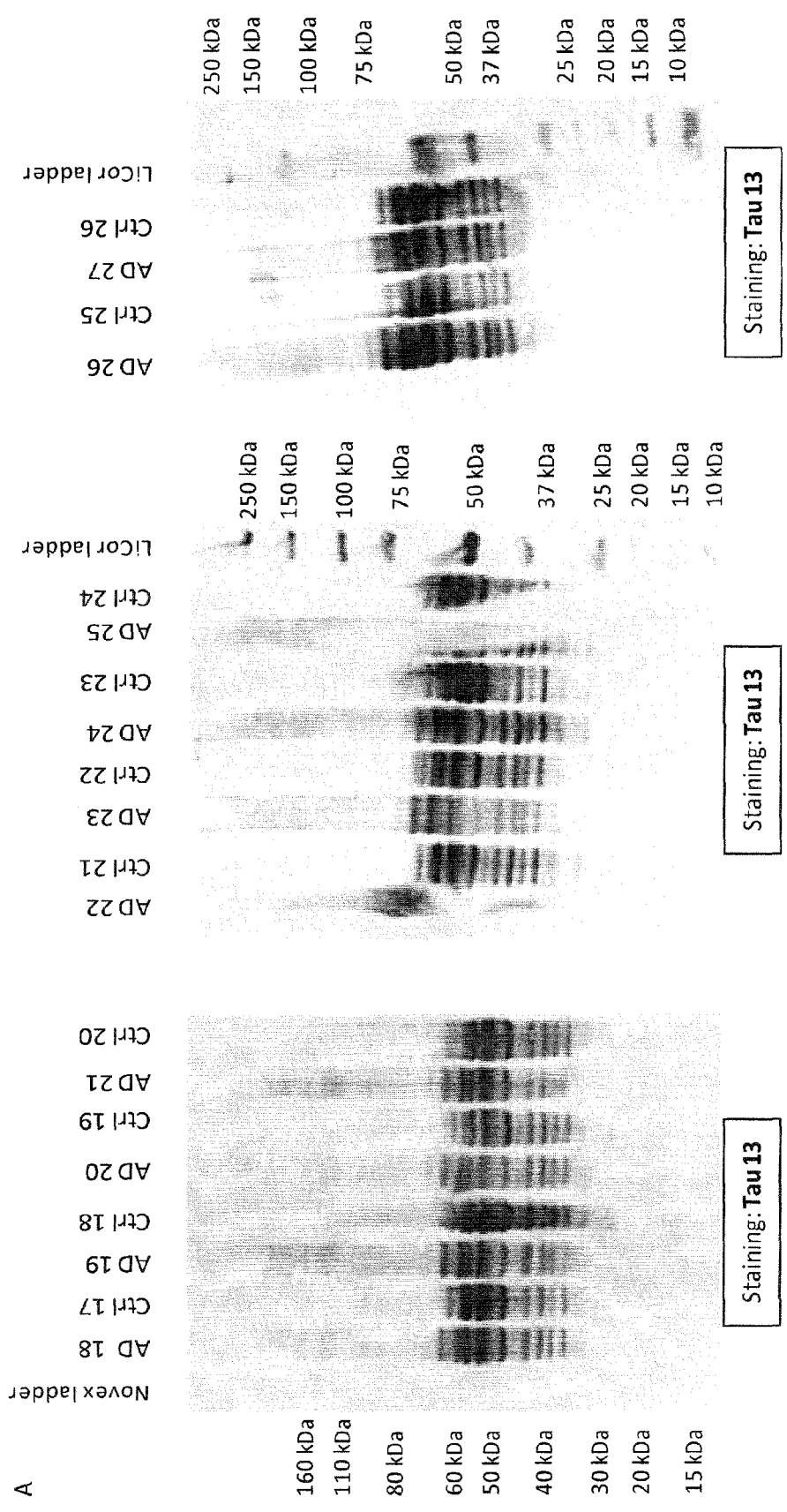
FIGS. 2 (2A and 2 B) shows results detection of total and p-Tau by commercial antibodies in human brain homogenates.
Figure 2B:
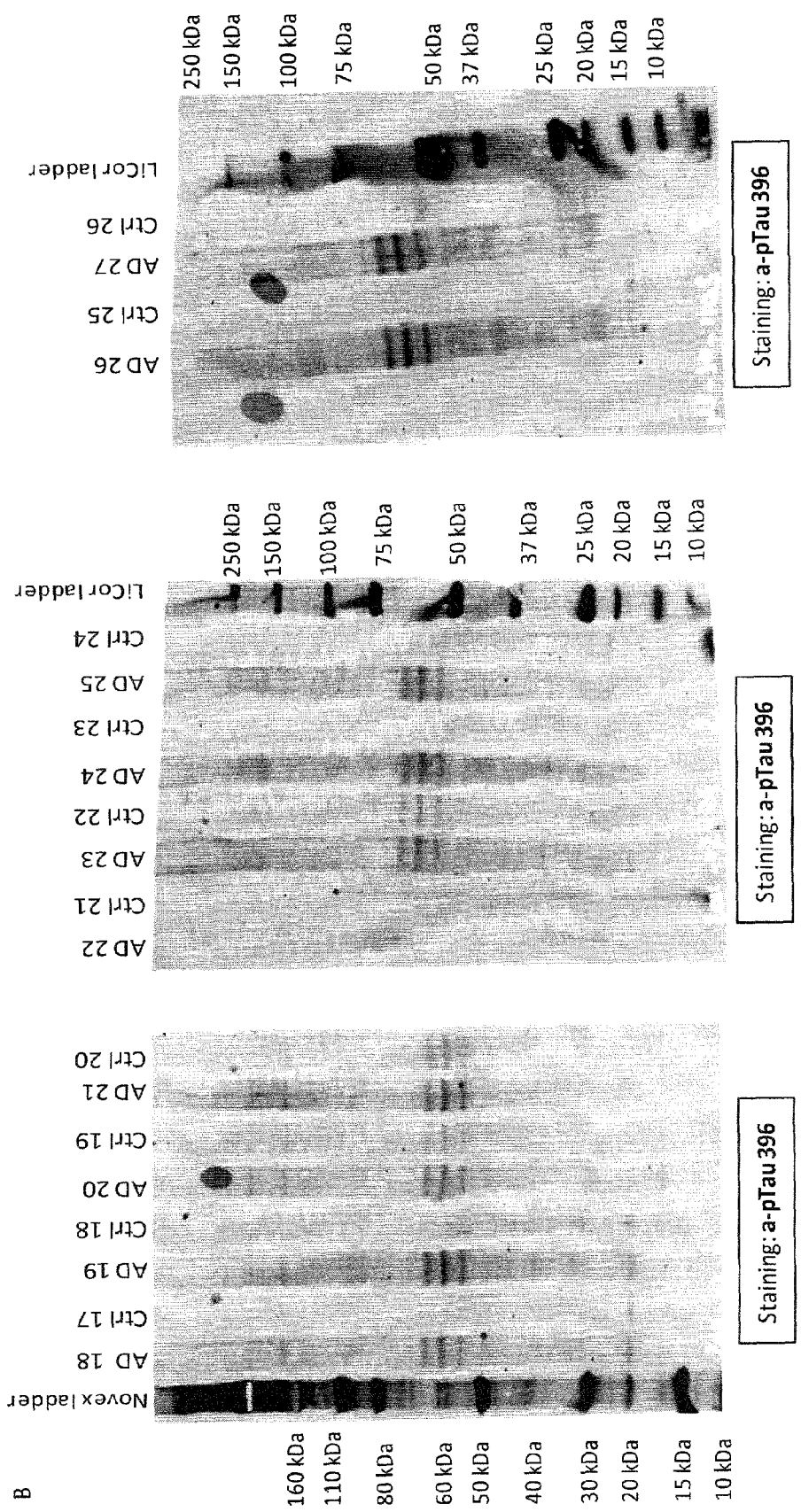

Antibodies ACI-35-2A1-Ab1, ACI-35-1D2-Ab1, and ACI-35-2G5-Ab3 were tested for their ability to detect phosphoTau (pTau) in brain homogenates from AD and control subjects, using a phospho-specific Western-blots. All post-mortem human cortex samples were first characterized using commercial antibodies against human Tau: anti-total Tau (TAU-13) and anti-pS396 Tau (E178) antibodies. As shown in FIG. 2A, using the TAU-13 antibody, we detected in all samples the characteristic Tau ladder corresponding to different Tau isoforms in the range of 50-70 kDa. Interestingly, in AD brain homogenates we also observed a relative shift in the migration pattern of Tau as expected for the presence of hyper-phosphorylated Tau in AD brains. Confirming this hypothesis, the commercial anti-pS396 Tau antibody discriminated very well controls and AD (FIG. 2B). Indeed, the anti-pS396 Tau antibody revealed three main immunoreactive bands corresponding to (hyper)-phosphorylated isoforms of Tau in all AD brain homogenates and with a very weak intensity, or absent in the healthy controls. In addition, the AD samples displayed a high molecular weight TAU-13 immunoreactive smear likely reflecting the presence of aggregated Tau (FIG. 2A).

Figure 3A:
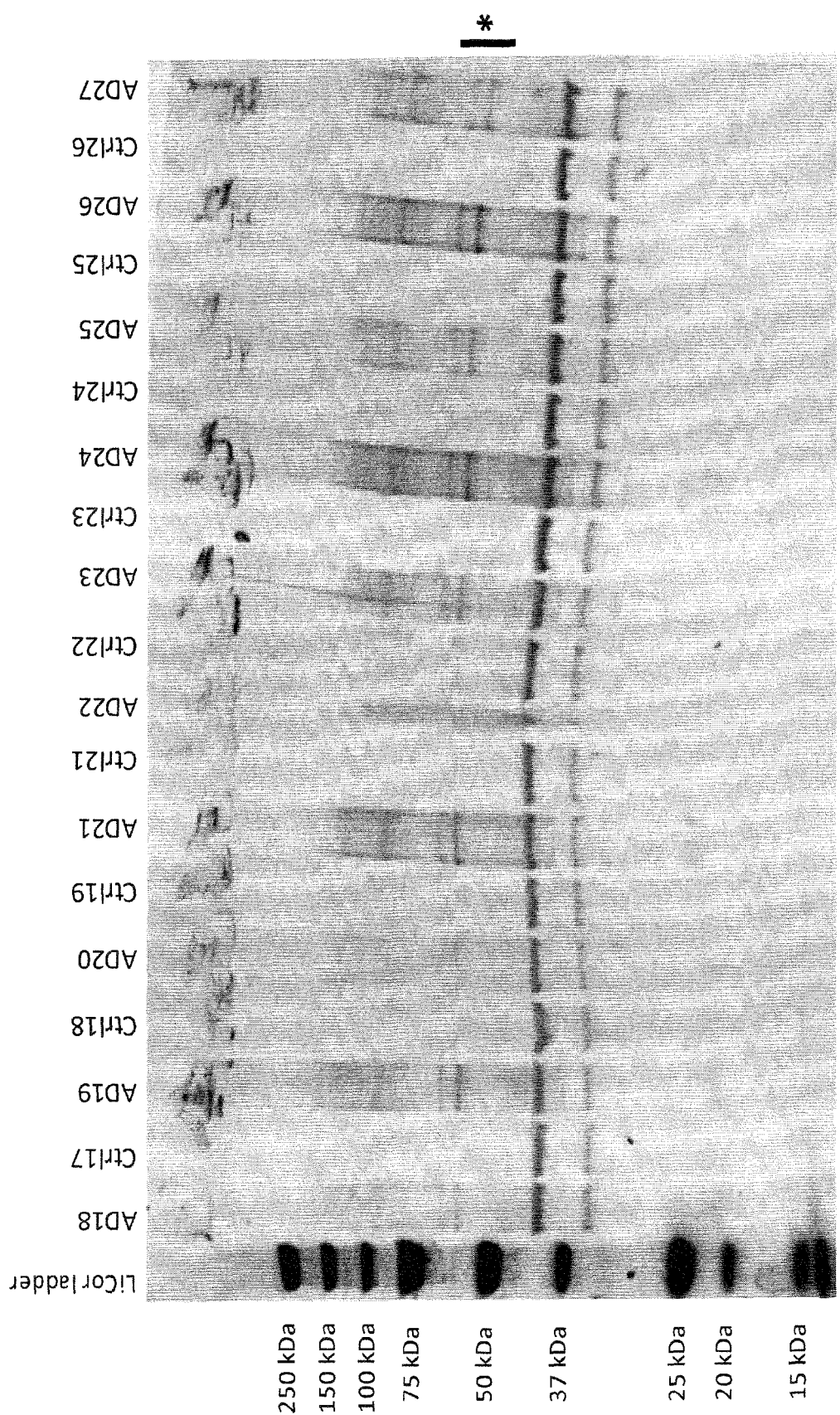
FIG. 3 (3A, 3B, 3C) shows Detection of phospho-Tau by ACI-35-2A1-Ab1 (A), ACI-35-1D2-Ab1 (B), and ACI-35-2G5-Ab3 (C) in human brain homogenates.
Figure 3B:
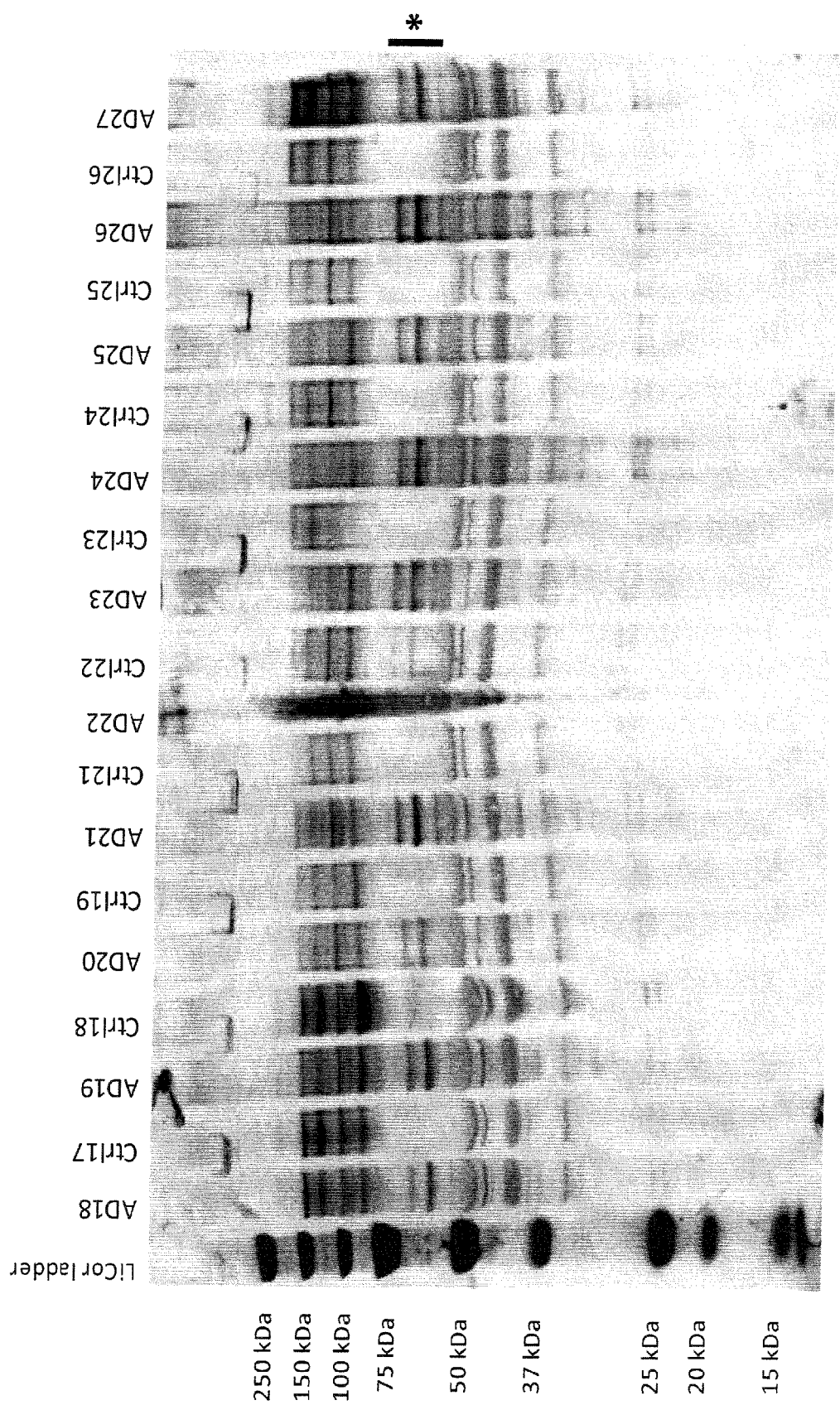
Figure 3C:
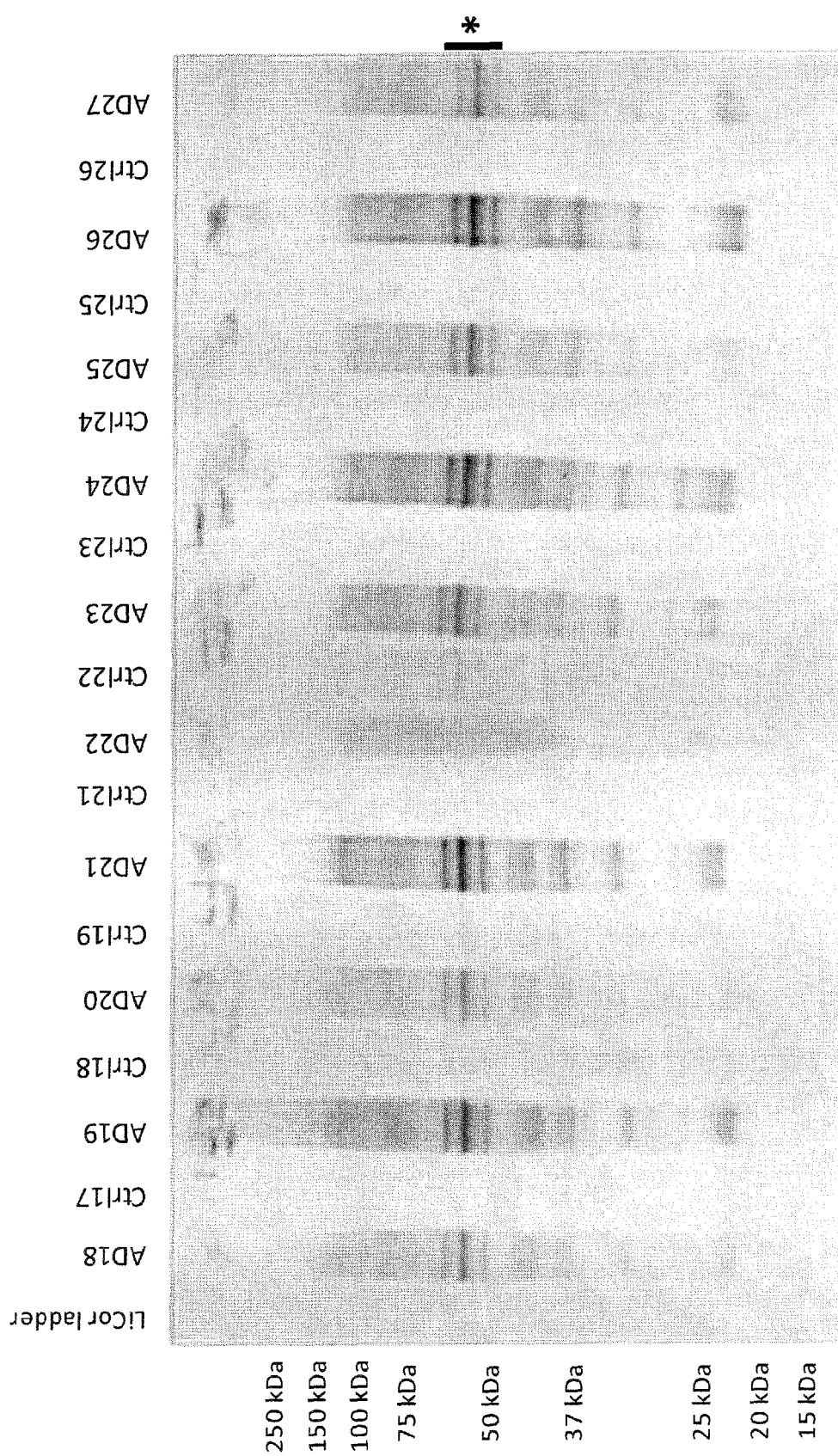

Western-blotting with ACI-35-2A1-Ab1 revealed the presence of two immunoreactive protein bands of the expected size for phospho Tau in the AD brain homogenates but not in controls (FIG. 3A). Weak immunoreactions by western blot using ACI-35-2A1-Ab1 may be explained by the presence of two major nonspecific bands at ~35 and ~40 kDa. Western-blotting with ACI-35-1 D2-Ab1 revealed the presence of two immunoreactive protein bands of the expected size for phospho Tau in the AD brain homogenates but not in controls (FIG. 3B). Weak immunoreactions by western blot using ACI-35-1D2-Ab1 may be explained by the presence of nonspecific bands at ~40 and ~50 kDa, as well as 4 nonspecific bands between 80 kDa and 150 kDa. Western-blotting with ACI-2G5-Ab3 revealed the presence of three main immunoreactive bands corresponding to (hyper)-phosphorylated isoforms of Tau in all AD brain homogenates and absent in the healthy controls, except for one control subject (C22), who has a family history of AD (FIG. 3C). This report demonstrated that ACI-35-2A1-Ab1, ACI-35-1D2-Ab1, and ACI-35-2G5-Ab3, can discriminate between AD and age-matched controls for the presence of pS396 Tau in human post-mortem cortex, and thus these monoclonal antibodies recognize AD-associated pathological Tau isoforms.

Example 7

Binding Studies V—Setup 1 (ELISA on Human Brain Samples)

7.1 Methods 7.1.1. Human Samples.

The same method for preparation of human samples as described in Method 5.1.1., except for the last part, S1 fraction preparation.

7.1.2. S1 Tau Protein Fraction: Subfractionation of Total Homogenate Fractions to Obtain Soluble Tau and Phospho-Tau Proteins.

To prepare the soluble Tau (S1) fraction used for the ALPHALISA™ assay, half volume of TH fraction was aliquoted and stored at −80° C. The remainder of the TH fraction was further processed by adding TRITON™ X-100 to a final concentration of 0.4%. Samples were mixed well and vortexed several times before being centrifuged at 5,000 rpm for 5 min at 4° C. The supernatant constitutes the S1 fraction. The samples were aliquoted and stored at −80° C. Protein concentrations were measured using Bradford reagent.

7.1.3. ALPHALISA™: ALPHALISA™ Assay to Detect the Presence Phosphorylated Tau in Human Post-Mortem Cortical Brain Homogenates from AD-Affected Individuals and Age-Matched Controls.

Antibodies ACI-35-2A1-Ab1, ACI-35-1D2-Ab1, and ACI-35-2G5-Ab3, all directed against Tau-pS396, were biotinylated using EZ LINK™ Micro Sulfo-NHS-LC-Biotinylation Kit (Thermo Scientific), according to manufacturer's instructions. Twentyfive-fold molar excess of Biotin over antibody was used in the labeling reaction. After biotinylation, the excess of free biotin was removed by dialysis against PBS using the SLIDE-A-LYZER™ MINI Dialysis Devices, 10K MWCO (Thermo Scientific). The biotinylated antibodies are designated as ACI-35-2A1-Ab1-BT, ACI-35-1D2-Ab1-BT, and ACI-35-2G5-Ab3-BT. Antibody Tau-13 was conjugated to the activated Alpha Acceptor beads (Perkin Elmer) using the following protocol: 0.1 mg of Tau-13 antibody solution (purified on Protein A column) was mixed with 1 mg of ALPHALISA™ Acceptor Bead pellets and complemented with 0.13 M phosphate buffer (pH 8.0) to a final reaction volume of 200 μL. Next, 1.25 μL of 10% TWEEN® 20 and 10 μL of a 25 mg/mL solution of $NaBH_3CN$ was added and the tube was incubated for 48 h at 37° C. with a mild rotation (7 rpm). After the conjugation reaction, the active sites on beads were blocked by adding 10 μL of a Carboxy-methoxylamine solution and further incubated at 37° C. for 1 h. Finally, the beads were washed two times with 200 μL of 0.1 M Tris-HCl pH 8.0 and stored at 4° C. in 200 μL storage buffer (PBS with 0.05% Proclin-300) that resulted in a final ALPHALISA™ Acceptor beads concentration of 5 mg/ml.

ALPHALISA™ is a homogenous assay based on bead proximity chemiluminescence. If Alpha Donor and Acceptor beads are in close proximity, upon laser excitation, a cascade of chemical reactions produces an amplified signal. Upon excitation at 680 nm, the photosensitizer contained in Donor beads converts ambient oxygen into more reactive singlet oxygen species. These singlets diffuse (up to 200 nm, within 4 μsec of a half-life) and produce a chemiluminescent reaction in the Acceptor beads, leading to light emission. The assay setting was as follows:

S1 samples were pre-diluted in Alpha Assay buffer (PerkinElmer AL000C) to obtain a 20 μg/mL stock concentration.

The following reagents were added to a 384-well white OPTIPLATE™ (PerkinElmer) to a final volume of 50 μL: S1 brain homogenate (5 μL), 10 μL of ACI-35-2A1-Ab1-BT, ACI-35-1D2-Ab1-BT, or ACI-35-2G5-Ab3-BT for a final antibody concentration of 0.2 nM, 0.5 nM, or 0.5 nM, respectively, and 10 μL of Tau13-Acceptor beads conjugate for a final bead concentration of 2.5 μg/mL. The reaction mix was incubated for 1 h at room-temperature, and 25 μL of Streptavidin Donor beads was added and further incubated for 2 h at room-temperature in the dark. Readout was done using EnSpire Alpha instrument and analysis using EnSpire Workstation version 3.00. Statistical analysis of data was performed using the GraphPad Prism software. Results are presented as Alpha units ±SD.

7.2 Results

Figure 4A:
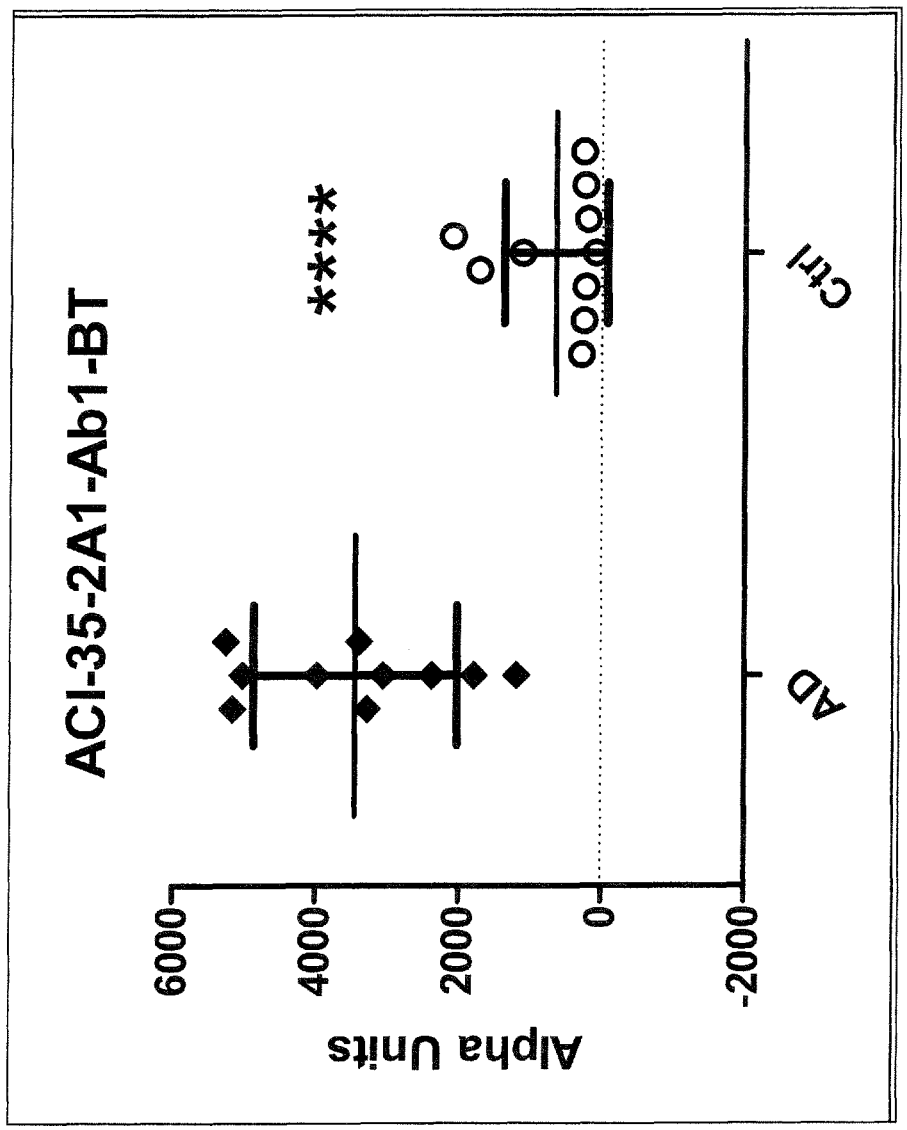
FIG. 4 (4A, 4B, 4C) shows results of detection of Tau-pS396 in human AD and control (Ctrl) brain by ACI-35-2A1-Ab1 (A), ACI-35-1D2-Ab1 (B), and ACI-35-2G5-Ab3 (C) antibodies using ALPHALISA™. **p<0.0001, p<0.01 by Mann-Whitney test.
Figure 4B:
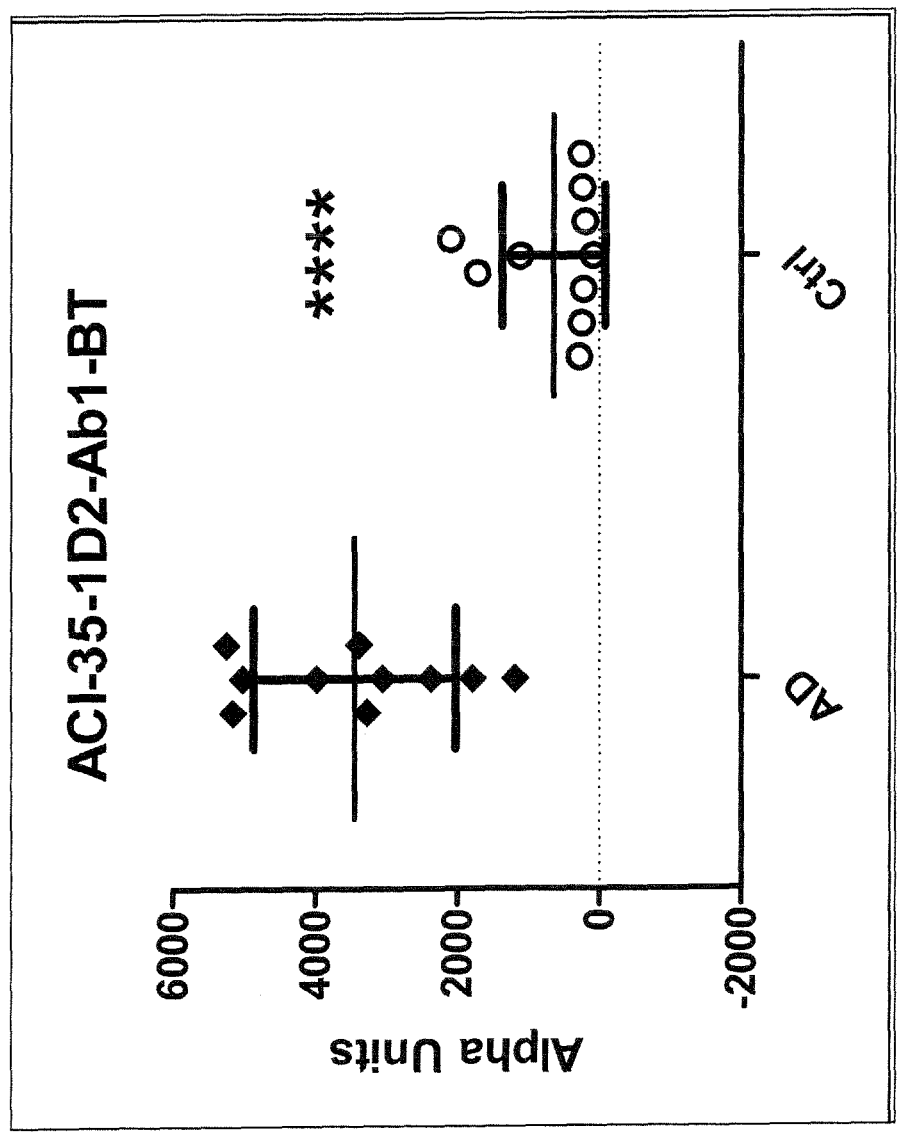
Figure 4C:
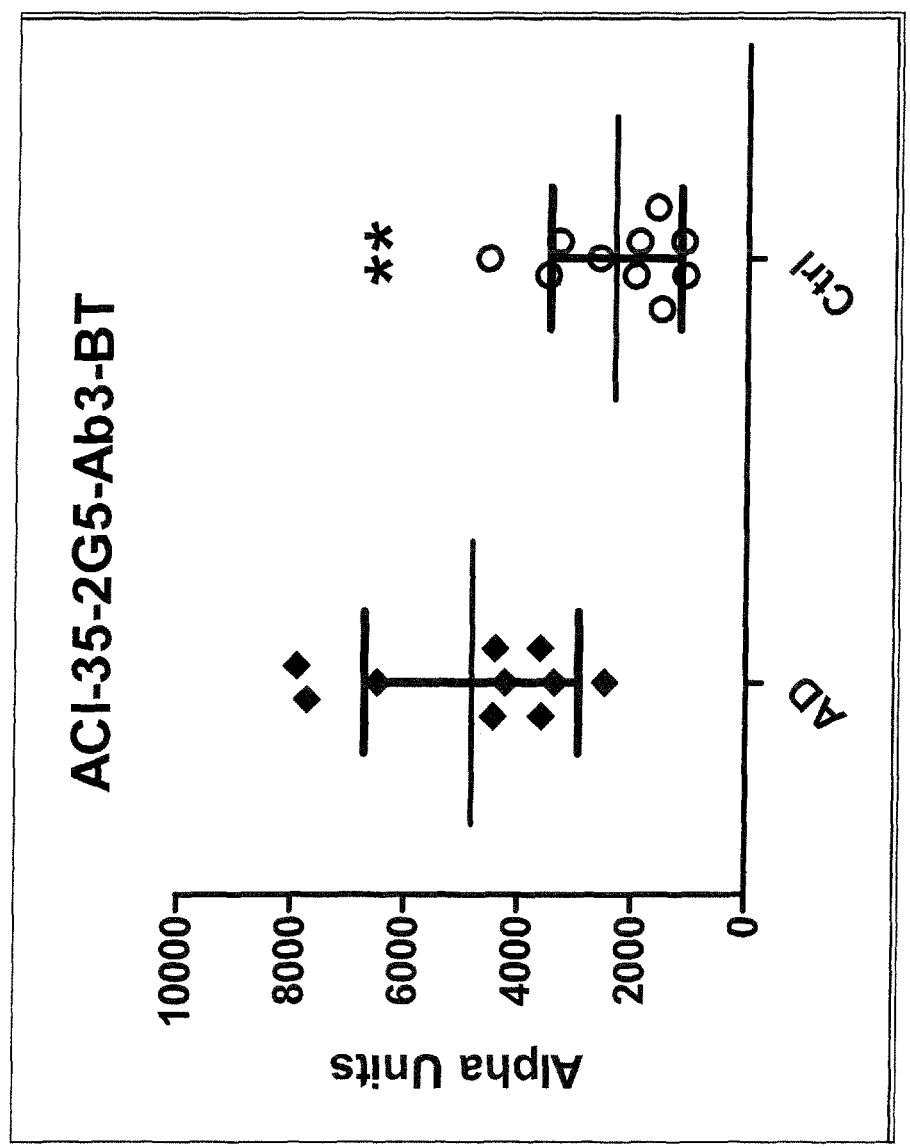

An ALPHALISA™ assay was used to test antibodies ACI-35-2A1-Ab1, ACI-35-1D2-Ab1, and ACI-35-2G5-Ab3 for the ability to detect Tau-pS396 in post-mortem human brain homogenates, and to discriminate AD from age-matched controls. All antibodies detected Tau-pS396 (FIGS. 4A, 4B, 4C). The difference in signal detection between AD and controls (n=10) was also highly significant for all antibodies, showing increased signal in brains of AD subjects; ACI-35-2A1-Ab1 ($p<0.0001$), ACI-35-1D2-Ab1 ($p<0.0001$), and ACI-35-2G5-Ab3 ($p=0.002$). In conclusion, ALPHALISA™ technology was used to demonstrate the capability of ACI-35-2A1-Ab1, ACI-35-1D2-Ab1, and ACI-35-2G5-Ab3 to detect pS396-Tau in brains of AD subject, and to differentiate between AD and control donors.

Example 8

In Vivo Efficacy of ACI-35-2G5-Ab3 Antibody 8.1 Methods 8.1.1. Study Setup: In Vivo Treatment Effects of 2 Administrations of Anti-pTau Antibody ACI-35-2G5-Ab3 in Tau Transgenic Mice Female and male Tau transgenic mice (TMHT) with a C57BL/6×DBA background, at an age of 6-7 months, were administered by i.p injection 3 or 10 mg/kg of ACI-35-2G5-Ab3, or vehicle control (PBS) two times, one week apart. On day 14, animals were euthanized, brains were harvested and processed for immunohistochemistry (IHC). For the determination of Tau pathology in the hippocampus and the amygdala 5 slices (1 from each level) per brain were labeled using AT180 (for Tau-pT231) and HT7 (for total human Tau) antibodies and subsequently immunoreactive area were evaluated using IMAGE-PRO® Plus (v6.2) software. Immunoreactive objects were measured above a size restriction (30 $\mu m^2$ in the amygdala, 7 $\mu m^2$ in the hippocampus) and above a dynamic intensity threshold. Total area and intensity of objects and the individual threshold were automatically filed. If used, a dynamic threshold was defined as mean intensity within area of intensity (AOI) plus a factor times the standard deviation of pixel intensities within the AOI. The region size was measured by manual delineation of the hippocampus and amygdala. AT180 and HT7 IR area data were normalized to the region (in hippocampus) or AOI size (in amygdala).

8.2 Results

The AT180 pTau antibody detects the endogenous and human pTau (doubly phosphorylated at Thr231 and Ser235).

Figure 5A:
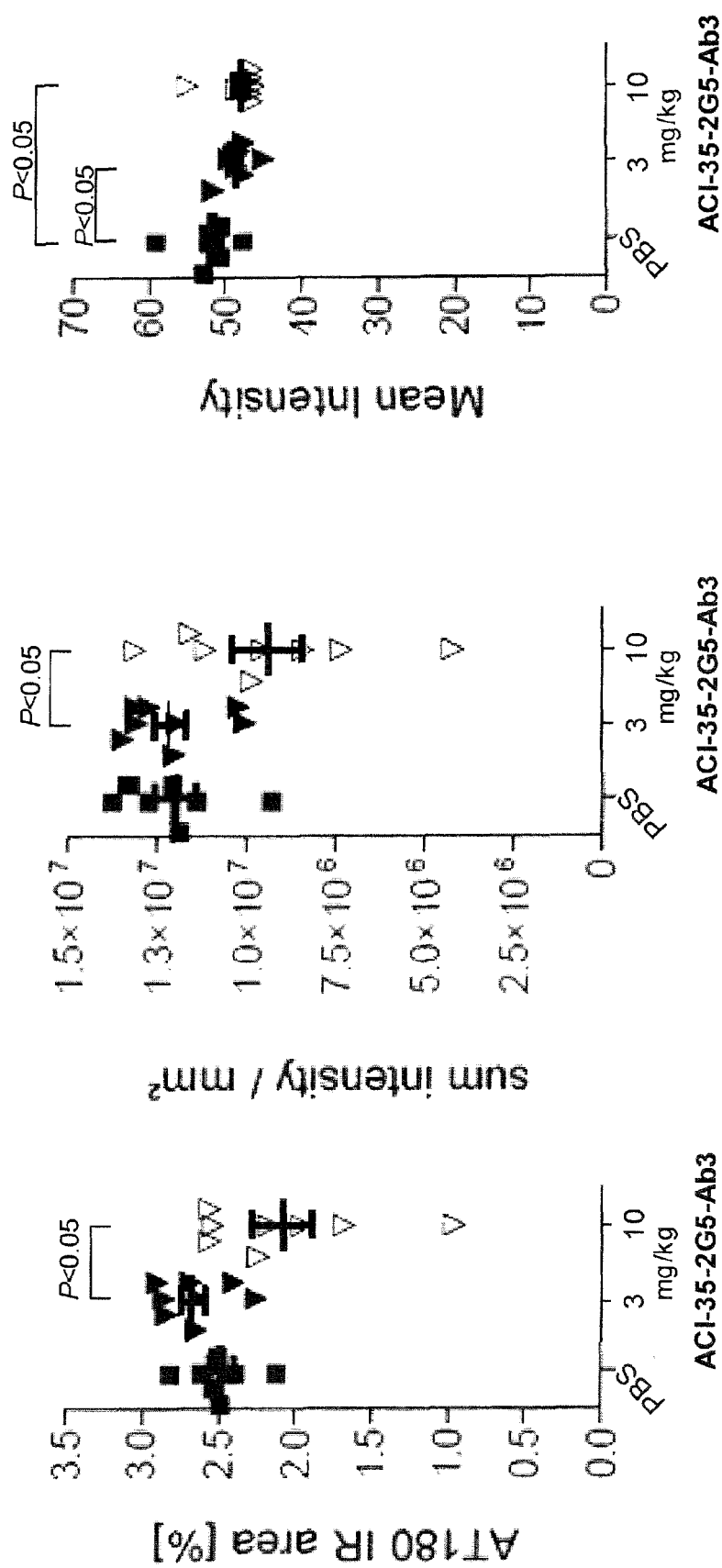
FIGS. 5 (5A and 5B) shows results of Tau-pT231 (AT180) IHC staining in the amygdala (A) and hippocampus (B), following treatment of Tau transgenic mice with ACI-35-2G5-Ab3.
Figure 5B:
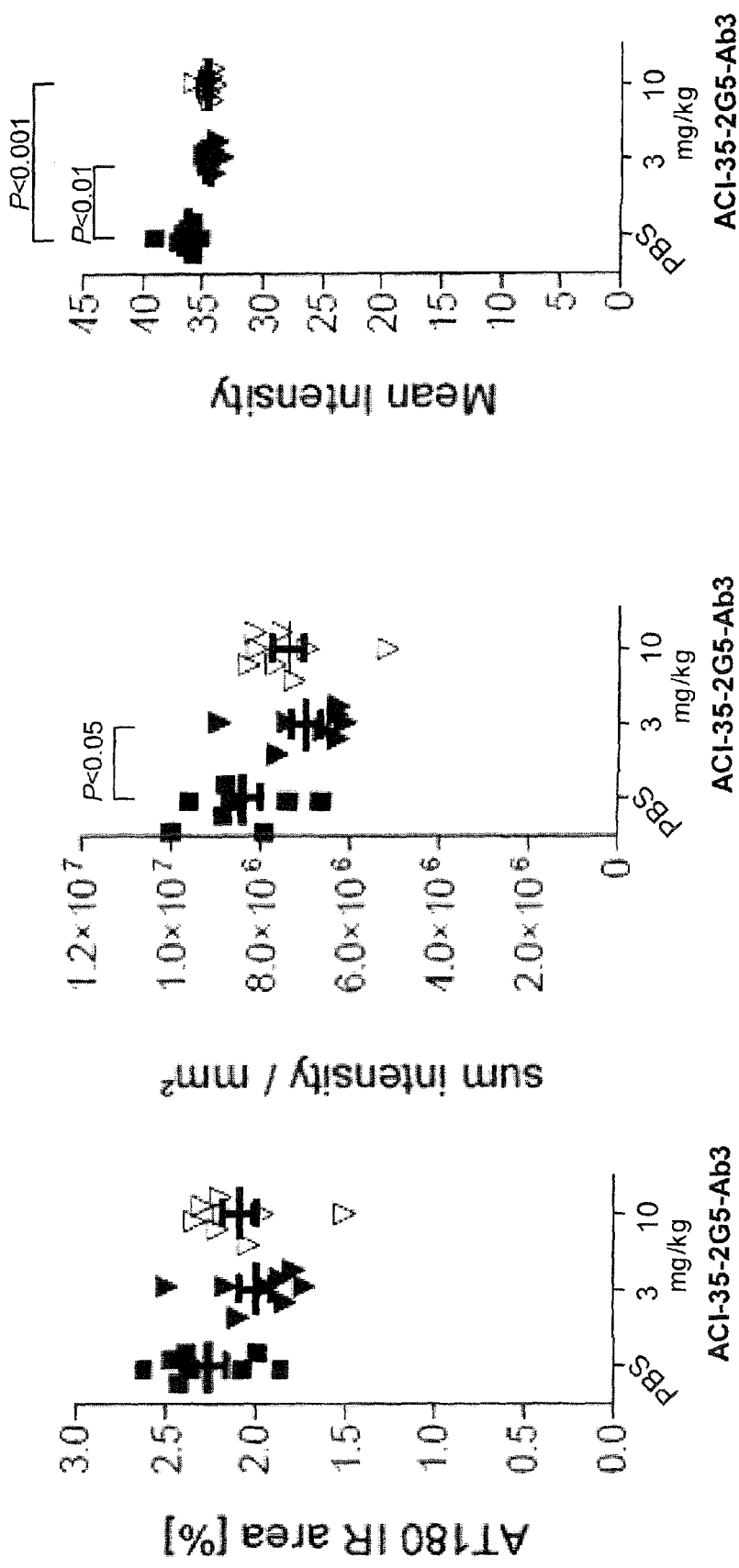

For the Tau transgenic mice used in this study. AT180 histological measurements concentrated on hippocampal and amygdaloideic neurons. Mice treated with ACI-35-2G5-Ab3 had a significant reduction for AT180 mean and normalized sum intensity of somal labeling, in both amygdala and hippocampus (FIGS. 5A and 5B), showing reduction of overall somal AT180-positive pTau in treated mice.

Figure 6A:
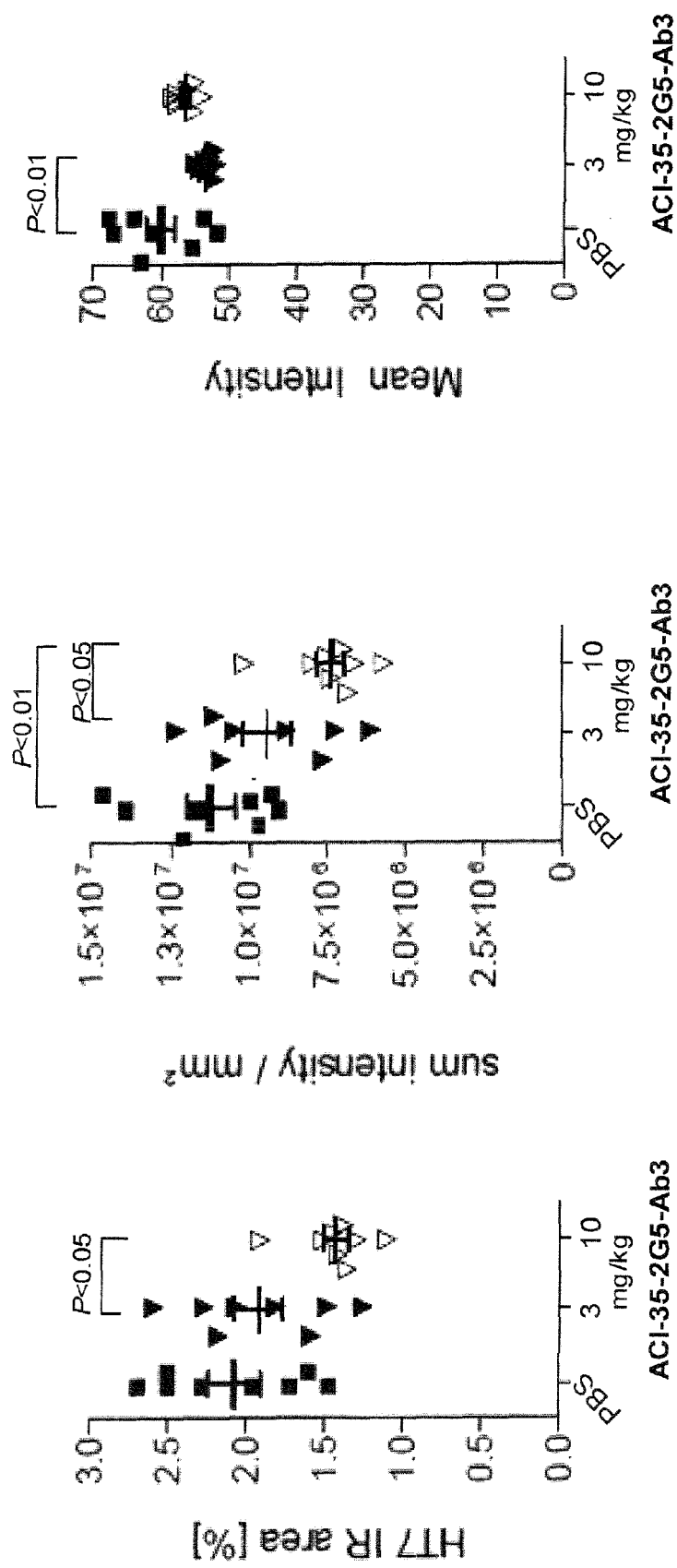
FIGS. 6 (6A and 6B) shows results of total Tau (HT7) IHC staining in the amygdala (A) and hippocampus (B), following treatment of Tau transgenic mice with ACI-35-2G5-Ab3.
Figure 6B:
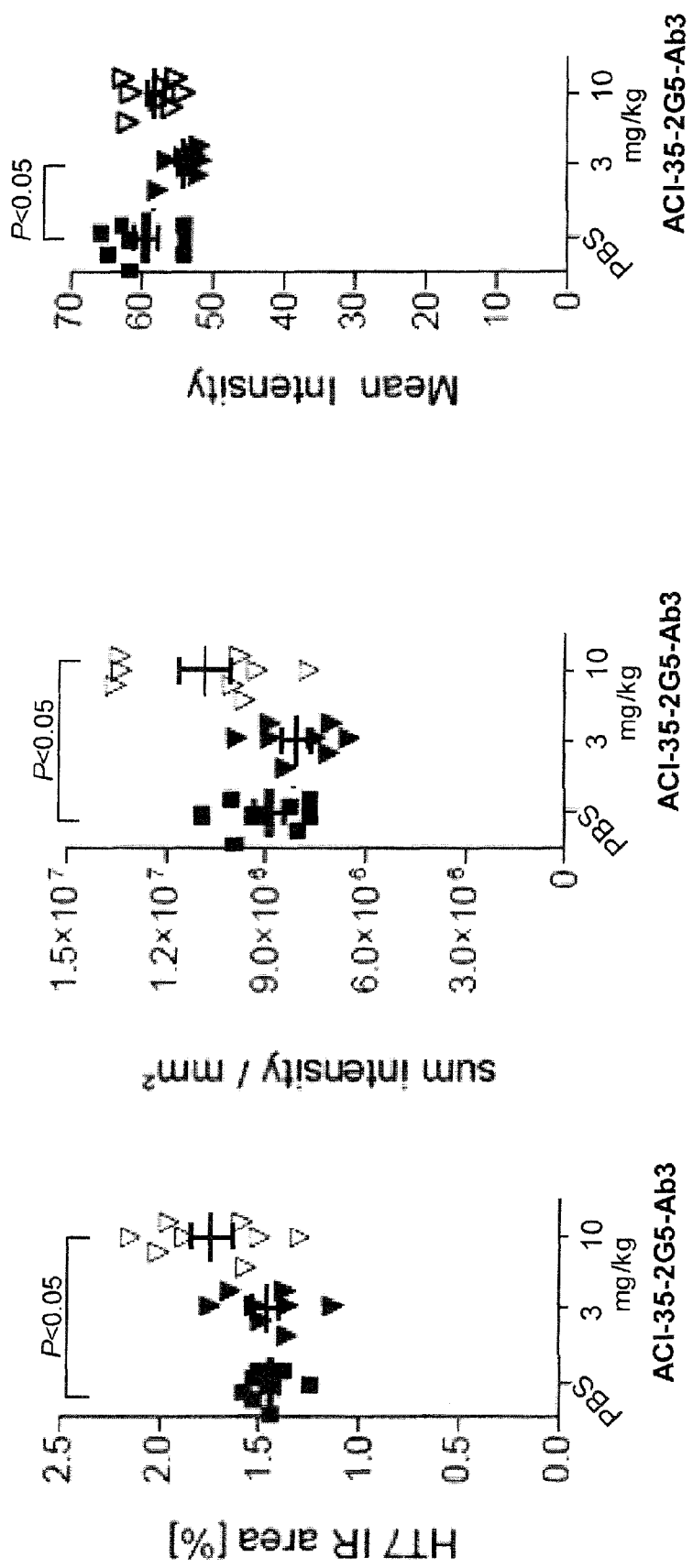

For total human (transgenic) Tau, the HT7 antibody was used. HT7 recognizes normal human Tau between residue 159 and 163. Histological measurements concentrated on immunoreactive somata of hippocampal and amygdaloideic neurons. Mice treated with ACI-35-2G5-Ab3 had reduced HT7 immunoreactive area, as well as sum and mean HT7 intensity of immunoreactivity in the amygdala (FIG. 6A). In the hippocampus, the same was observed for mean intensity (FIG. 6B). However, an increase in HT7 labeling was observed for immunoreactive area, and sum intensity in the hippocampus in mice treated at 10 mg/kg. This increase observed in the hippocampus was mainly due to three mice out of the total eight mice investigated.

ACI-35-2G5-Ab3 treatment significantly decreased AT180 immunoreactive pTau levels in both investigated regions, thus in somata of hippocampal and amygdaloideic neurons. In the amygdala, the sum intensity of labeling was decreased for both AT180 immunoreactive pTau and HT7 immunoreactive total human Tau. Treatment with a dose of 3 mg/kg also significantly decreased mean HT7 intensity in both regions. However, at 10 mg/kg the average HT7 immunoreactive area and sum intensity in the hippocampus were increased over that of control treated mice, suggesting that a ACI-35-2G5-Ab3 treatment leads to shift from pathological pTau.

Example 9

Epitope Mapping of Anti pTau Antibodies 9.1 Methods

Epitope mapping of anti-phospho Tau mouse monoclonal antibodies was performed by ELISA using different phospho and non-phospho peptide libraries. The amino acid sequences of peptide library T3 used are shown in Table 11A. Each library consisted of short biotinylated peptides spanning phospho and non-phospho sequences present in the peptide vaccine. Additionally, a peptide library was generated substituting each residue of a peptide sequence that binds to the antibody with Alanine (Ala), as shown in Tables 11B and 11C. Each library consisted of short biotinylated peptides spanning phospho and non-phospho sequences present in the peptide vaccine. Peptide libraries were purchased from ANAWA Trading SA. Peptide libraries were purchased from ANAWA Trading SA. Epitope mapping was done according to the manufacturer's (Mimotopes) instructions. Briefly, streptavidin coated plates (NUNC) were blocked with 0.1% BSA in phosphate-buffered saline (PBS) overnight at 4° C. After washing with PBS-0.05% TWEEN® 20, plates were coated for 1 hr at RT with the different peptides from each library, diluted in 0.1% BSA, 0.1% sodium azide in PBS to a final concentration of 10 μM. After washing, plates were incubated for 1 hr at RT with the antibody to be tested diluted to 40 ng/ml in 2% BSA, and 0.1% sodium azide in PBS. Plates were washed again and incubated with AP-conjugated anti-mouse IgG secondary antibody (Jackson ImmunoResearch Laboratories, Suffolk, England) at 1/6000 dilution for 1 hr at RT. After a final wash, plates were incubated with p-nitrophenyl phosphate disodium hexahydrate (pNPP; Sigma-Aldrich, Buchs, Switzerland) phosphatase substrate solution, and read at 405 nm following 2 hr incubation using an ELISA plate reader. Binding was considered positive if the optical density (O.D.) was at least 2-times over background O.D.

9.2 Results

As a result of the epitope mapping experiments, epitopes could be identified including the required phosphorylated amino acid residue (see table 5) to which the antibodies disclosed herein specifically bind.

Tau aa 393-401, with requirement for pS396 (ACI-35-2A1-Ab1; ACI-35-2A1-Ab2)

Tau aa 396-401, with requirement for pS396 (ACI-35-4A6-Ab1)

Tau aa 394-400, with requirement for pS396 (ACI-35-1D2-Ab1)

Tau aa 402-406, with requirement for pS404 (ACI-35-2G5-Ab1)

Tau aa 393-400, with requirement for p396 (ACI-35-2G5-Ab2; ACI-35-2G5-Ab3)

Example 10

Phosphorylation of Tau at Serine 396 (pS396) Using GSK3β Kinase, and SOS-PAGE/Western-Blot Analysis

10.1 Methods

The longest isoform of human full-length Tau (TAU441; SignalChem) at a final concentration of 16 µM (20 µg Tau/25 µL reaction) was incubated with 0.018 U GSK3β/pmol of Tau in phosphorylation buffer containing HEPES pH 7.64 (40 mM), EGTA (5 mM), $MgCl_2$ (3 mM), and ATP (2 mM) for 1, 6, or 20 h at 4, 30, or 37° C. One unit of GSK3β is defined by the manufacturer (New England BioLabs) as the amount of enzyme that will transfer 1 pmol phosphate from ATP to CREB phosphopeptide (KRREILSRRPpSYR; SEQ ID NO: 223) in 1 minute at 30° C. Tau phosphorylated with GSK3β (pTau-GSK3β) was probed with antibodies directed against Tau phosphorylated at serine 202, 396, 404, 409, threonine 181, 205, and 231, and total Tau, run on direct ELISAs and Western-blots (WBs), to optimize and verify kinase activity and specificity (not shown). Additionally, blots were probed for the presence of GSK3β using an anti-GSK3α/β antibody (BioSource Invitrogen). For all WBs, pTau-GSK3β was diluted by adding an equal volume of sample buffer A (125 mM Tris-HCl pH 6.8, 4% [w/v] sodium dodecyl sulfate [SDS], 20% glycerol, 0.01% bromophenol blue, 5% β-mercaptoethanol), and the samples were heated to 95° C. for 10 min. 30 µg of sample was loaded onto a 4-12% Bis-Tris gel (Invitrogen) and run in MOPS SDS buffer (Invitrogen). Proteins were transferred to a 0.45 µm PVDF membrane in transfer buffer (25 mM Tris pH 8.6, 190 mM glycine, 20% methanol). To verify protein transfer, membranes were stained with Ponceau S for 5 min. Membranes were then washed and then blocked for 1 hour in blocking buffer (5% BSA in TBS [50 mM Tris-HCl, pH 7.6, 150 mM NaCl]). Membranes were blotted over-night at 4° C. with the primary antibodies in blocking buffer and 0.1% TWEEN®. Blotting with the ACI-35-2G5-Ab3 was done at 0.5 µm/mL antibody dilution.

10.2 Results

Figure 7:
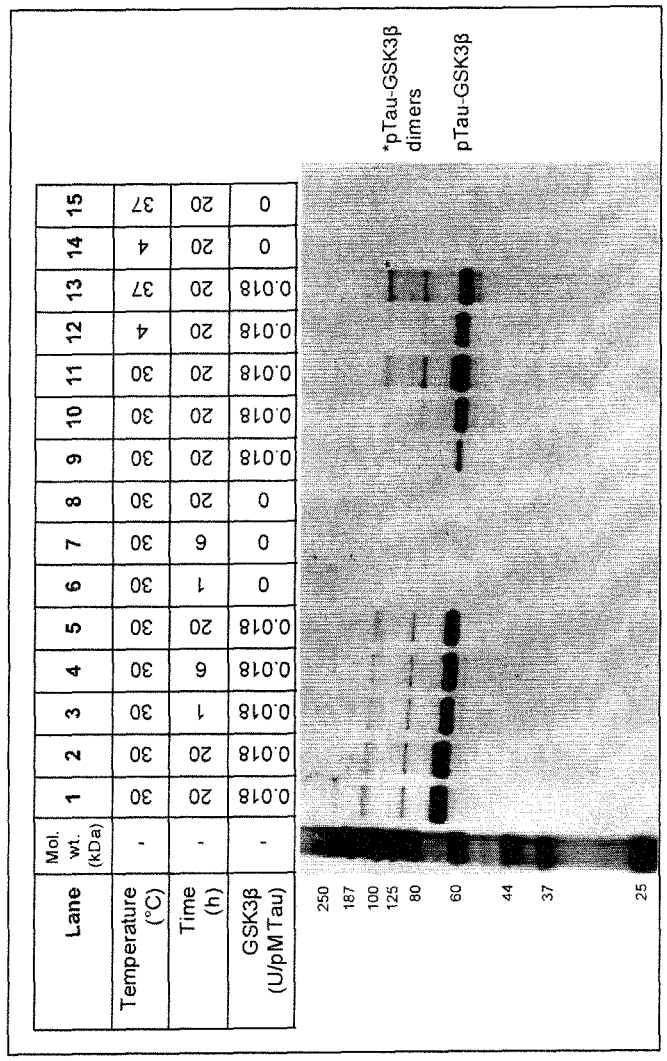
FIG. 7 shows an SDS-PAGE for Tau-pS396 generated using different GSK3β conditions, and the membrane blotted using the ACI-35-2G5-Ab3 antibody.

Tau treated with GSK3β resulted in high presence of phosphorylation at Tau serine 396 (Tau-pS396), as verified using antibodies specific to different Tau phospho-serine and -threonine residues (not shown). FIG. 7 shows an SDS-PAGE for Tau-pS396 generated using different GSK3β conditions, and the membrane blotted using the ACI-35-2G5-Ab3 antibody. The ACI-35-2G5-Ab3 antibody, specific for Tau-pS396, demonstrated a good signal for Tau-pS396, with bands also observed suggesting that it binds to Tau-pS396 dimers (FIG. 7, lanes 11 and 13). No bands were observed in the absence of GSK3β treatment (lanes 6-8 and 14-15).

Example 11

Detection of Phosphorylation of Tau (pSer396) in Human Cerebrospinal Fluid (CSF) Samples

11.1 Methods

11.1.1 Human Samples—Post-Mortem Brain Samples

Temporal post-mortem cortex of one Alzheimer's disease (AD) donor AD19 was obtained from the Brain Endowment Bank of the University of Miami. We kindly acknowledge the University of Miami Brain Endowment Bank for providing samples for this study. The demographic information about the donor is shown in Table 12 below, where the Braak disease stage (Braak and Braak (1991) Neuropathological staging of Alzheimer-related changes. Acta Neuropathol 82:239-259) is also indicated.

TABLE 12

Description of the brain sample AD19 used in this study

| Sample ID | Gender | Age at death | Age at diagnosis | Disease duration | disease stage |
|---|---|---|---|---|---|
| AD 19 | F | 81 | 77 | 4 | Braak V |

11.1.2. Preparation of Homogenate Fraction S1 from Post-Mortem Brain

Temporal post-mortem cortex of the AD19 donor was homogenized according to the following protocol. Brain fragment was weighted and homogenized in 9 volumes of 25 mM Tris-HCl pH 7.4, 150 mM NaCl, 1 mM EDTA, 1 mM EGTA containing phosphatase inhibitors (30 mM NaF, 0.2 mM $Na_3VO_4$, 1 nM okadaic acid, 1 mM PMSF, 5 mM $Na_4P_2O_7$) and protease inhibitors (Complete Mini, Roche 04 693 124 001). Homogenization was done on ice using a glass potter. This constitutes the Total Homogenate fraction (TH). Half volume of TH fraction was aliquoted and stored at −80° C. The remainder of the TH fraction was further processed by adding TRITON™ X-100 to a final concentration of 0.4%. The sample was mixed well and vortexed several times before being centrifuged at 5,000 rpm for 5 min at 4° C. The supernatant constitutes the S1 fraction. The sample was aliquoted and stored at −80° C. Protein concentration was measured using Bradford reagent (Sigma B6916-500).

11.1.3 Human CSF Samples

Cerebrospinal fluid (CSF) samples from clinically confirmed mild-to-moderate Alzheimer's disease (AD) patients and healthy volunteer control donors (Ctrls) were provided by the Charité School of Medicine Berlin. We kindly acknowledge the Charité School of Medicine Berlin for providing samples for this study. The samples were aliquoted, stored at −80° C. and used without further processing. Demographic and clinical information on CSF sample donors is shown in Table 13 below.

TABLE 13

Demographic and clinical information on CSF sample donors

| diagnosis | n | mean age (StDev) | age range | % females | MMSE score (StDev) | MMSE range |
|---|---|---|---|---|---|---|
| AD | 17 | 72.5 (8) | 57-85 | 35 | 21.2 (4) | 13-27 |
| Ctrl | 16 | 65 (7) | 53-77 | 69 | 29 (1) | 27-30 |

11.1.4 Immuno-Enrichment of CSF Tau 11.1.4.1 Antibody Coupling

For immuno-enrichment of CSF Tau, a commercial human Tau antibody (clone HT7, Thermo Scientific MN 1000) was used. In order to couple HT7 to Protein G DYNABEADS® (Life Technologies 10004D), for each sample 1.5 mg (50 µL) Protein G DYNABEADS® were resuspended by vortexing and transferred to a 1.7 mL Maximum Recovery tube (Axygen MCT-175-L-C). The tubes were placed on a magnetic support (DynaMag, Life Technologies 123.21D) in order to concentrate the beads on the side of the tube and to remove the buffer. Binding of 1 µg HT7 in 200 µL of PBS to the Protein G DYNABEADS® was performed using a Hula Mixer (Life Technologies) at 10/20 rpm, 25°/10 tilt, 5°/2 vibro for 10 min, after which tubes were placed on the magnet, the buffer was removed and tubes were washed once by gentle pipetting with 200 µL PBS/0.02% TWEEN® 20 and two times with 200 µL conjugation buffer (20 mM Na Phosphate, 150 mM NaCl, prepared freshly). The washing buffers were always removed using the magnet. For crosslinking HT7 to the Protein G DYNABEADS®, the HT7-beads were resuspended in 250 µL of 5 mM BS3 solution (Sigma-Aldrich S5799) dissolved in conjugation buffer and incubated with rotation (same settings as above) for 30 min at room temperature (RT), the reaction was terminated by adding 12.5 µL of quenching buffer (1M Tris-HCl pH 7.5) for 15 min followed by three washes with 200 µL PBS/0.02% TWEEN® 20.

11.1.4.2 CSF Tau Immuno-Enrichment

CSF was used undiluted and 1 mL of CSF for each donor was transferred to the tube containing the HT7 cross-linked beads and incubated for 1 hr 4° C. under continuous rotation (10 rpm). After removing the unbound material on the magnet, the beads were washed with 200 µL PBS/0.02% TWEEN® 20 and Tau was eluted in 20 µL 1% sodium dodecyl sulphate (SDS) in PBS at 70° C. for 10 min. In order to avoid sedimentation of beads, tubes were mixed shortly (300 rpm in the heated horizontal mixer, for 5 seconds, every minute). After this incubation, the eluted samples were collected by placing the tubes on the magnet.

As a positive control, Tau was also enriched from human brain homogenates. For this serial dilutions of human brain S1 fraction from AD19 donor were prepared in PBS (0.5 µg/mL, 0.17 µg/mL, 0.056 µg/mL, 0.019 µg/mL, 0.006 µg/mL, 0.002 µg/mL, 0.0007 µg/mL). Each sample (1 mL) was then treated as described above and eluted in 25 µL 1% SDS.

11.1.5.1 ALPHALISA™

11.1.3.1 ALPHALISA' Assay Description

ALPHALISA™ is a homogenous assay that utilizes the bead-based Alpha technology. ALPHALISA™ was selected as a technology platform based on sensitivity and minimal number of steps. Briefly, the assay is based on bead proximity. Upon excitation at 680 nm, the photosensitizer containing Donor beads converts ambient oxygen into singlet oxygen species, these diffuse (up to 200 nm, within 4 µsec of a half-life) and produce a chemiluminescent reaction in the Acceptor beads, leading to light emission.

Figure 8:
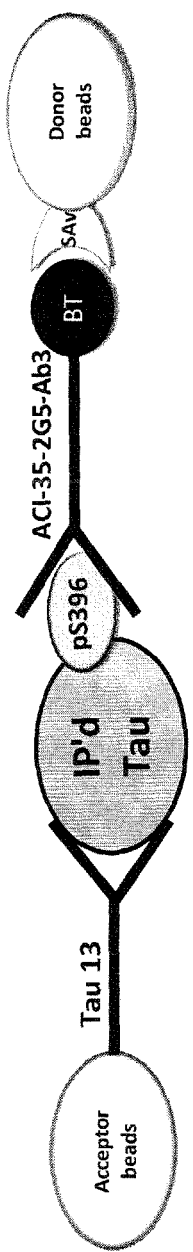
FIG. 8 shows specific ALPHALISA™ assay setup using ACI-35-2G5-Ab3-BT and Tau-13 antibodies.

The assay setting used in our experiments was the following (see also FIG. 8):

Pan-Tau antibody Tau-13 (Abcam ab24636), coupled to Alpha Acceptor beads binds human Tau present in the sample and forms the "Tau protein-Tau-13 antibody-Acceptor beads" complex Detection antibody ACI-35-2G5-Ab3-BT binds to the pS396 of human Tau and allows binding the Streptavidin-coated (SAv) Alpha Donor beads to the complex.

After bringing all reagents into the reaction, the chemiluminescent signal is read using EnSpire Alpha 2390 Reader.

11.1.5.2 Biotinylation of ACI-35-2G5-Ab3 Antibody

In order to be used in the ALPHALISA™ assay, the antibody ACI-35-2G5-Ab3 was biotinylated using EZ_LINK™ Micro Sulfo-NHS-LC-Biotinylation Kit (Thermo Scientific 21935), according to manufacturer's instructions. Twenty five-fold molar excess of Biotin over the antibody was used in the labeling reaction. After the biotinylation, the excess of free biotin was removed by washing the antibody four time in PBS using 50,000 MWCO Spin-X UF 500 Concentrator (Corning 431480). The biotinylated ACI-35-2G5-Ab3 antibody is indicated as ACI-35-2G5-Ab3-BT.

11.1.5.3 Coupling of the Tau-13 Antibody to ALPHALISA™ Acceptor Beads.

In order to be used in the ALPHALISA™ assay, the antibody Tau-13 was conjugated to the activated Alpha Acceptor beads (Perkin Elmer 6772001). The following conjugation protocol was used: 0.1 mg of Tau-13 antibody solution (purified on Protein A column) was mixed with 1 mg of ALPHALISA™ Acceptor Beads pellet and complemented with 0.13 M phosphate buffer (pH 8.0) to a final reaction volume of 200 µL. Next, 1.25 µL of 10% TWEEN® 20 and 10 µL of a 25 mg/mL solution of NaBH3CN were added and the tube was incubated for 48 h at 37° C. with a mild rotation (7 rpm). After the conjugation reaction, the active sites on beads were blocked by adding 10 µL of a Carboxy-methoxylamine solution and further incubated at 37° C. for 1 h. Finally, the beads were washed two times with 200 µL of 0.1 M Tris-HCl pH 8.0 and stored at 4° C. in 200 µL storage buffer (PBS with 0.05% Proclin-300) that resulted in a final ALPHALISA™ Acceptor beads concentration of 5 mg/ml.

11.1.5.4 Limit of Detection Determination Using Brain pS386-Tau

Immuno-enriched Tau brain samples, S1 brain fraction samples and buffer blanks were used for this experiment. Each sample was analyzed in 50 µL final volume using a 384-well white OPTIPLATE™ (PerkinElmer 6007291). Dilutions of all reagents were done with Alpha Assay buffer (PerkinElmer AL000C).

5 µL sample (⅒ of the final volume, therefore the final protein concentration in the assay corresponds to the ⅒ of the sample concentration).

10 µL 0.5% SDS for S1 brain fraction samples or 10 µL plain buffer for the immuno-enriched Tau brain samples was added 15 µL of ACI-35-2G5-Ab3-BT antibody (final concentration: 5 nM) mixed with Tau13-Acceptor beads conjugate (final bead concentration: 2.5 µg/mL)

Incubation at room temperature for 1 hr

20 µL of Streptavidin Donor beads (final bead concentration: 25 µg/mL)

Incubation at room temperature for 30 min (protected from light)
Readout using EnSpire Alpha instrument and analysis using EnSpire Workstation version 3.00

11.1.5.5 Determination of Immuno-Enriched pS396-Tau in CSF

Each sample was analyzed in 50 µL final volume using a 384-well white OPTIPLATE™ (PerkinElmer 6007291). Dilutions of all reagents were done with Alpha Assay buffer (PerkinElmer AL000C).

5 µL of immunoprecipitated eluate from each donor
20 µL of ACI-35-2G5-Ab3-BT antibody (final concentration: 5 nM) mixed with Tau13-Acceptor beads conjugate (final bead concentration: 2.5 µg/mL)
Incubation at RT for 1 h
25 µL of Streptavidin Donor beads (final bead concentration: 25 µg/mL)
Incubation at RT for 30 min (protected from light)
Readout using EnSpire Alpha instrument and analysis using EnSpire Workstation version 3.00

11.1.6 Statistical Analysis

Statistical analysis of data was performed using the GraphPad Prism software.

11.2 Results

Figure 9:
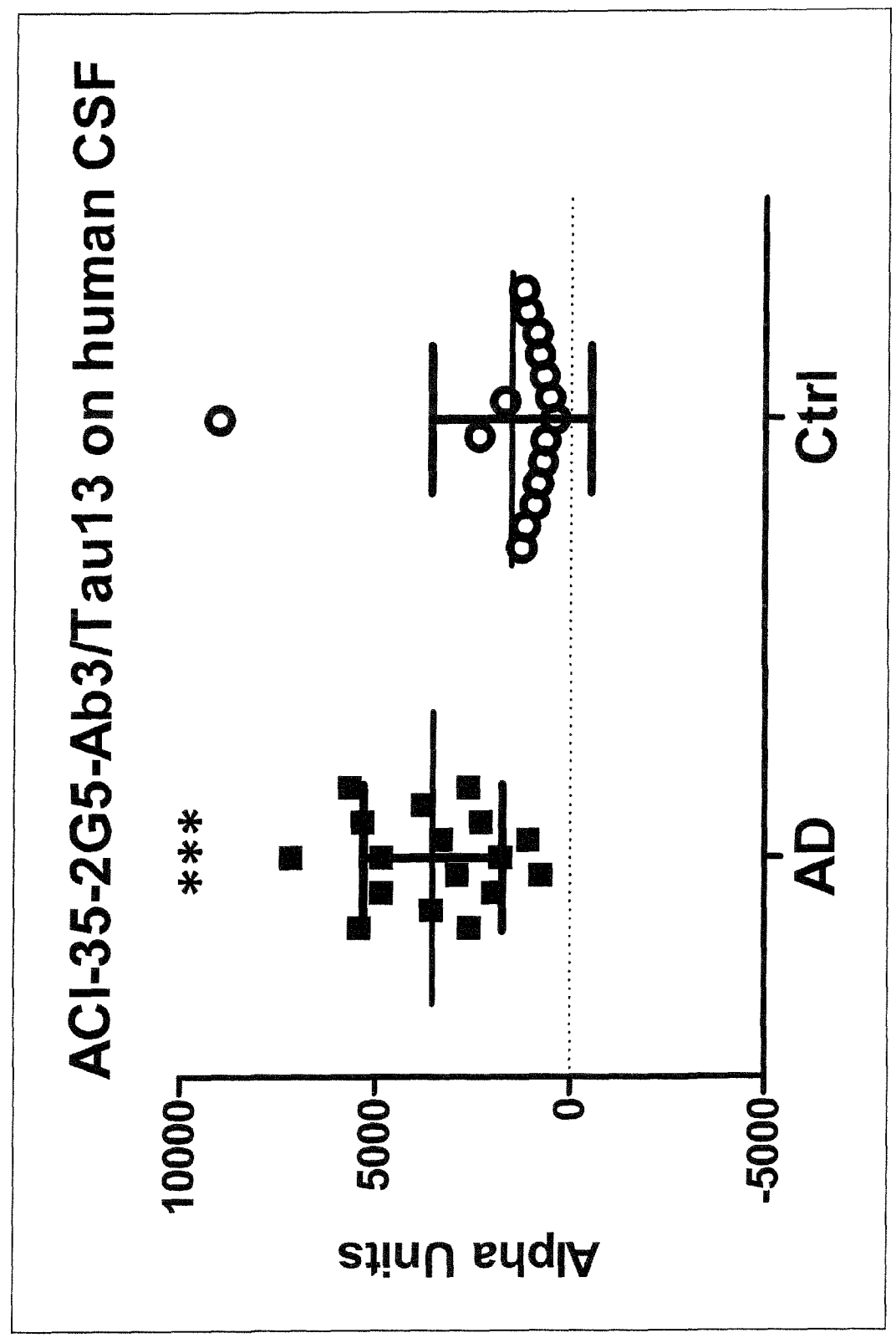
FIG. 9 shows detection of Tau-pS396 in human S1 brain fraction from one AD donor; comparison of signal obtained from samples enriched by IP and non-IP samples.

Preliminary experiments indicated that the amount of pS396 present in human CSF was too low for detection. For this reason, an immuno-enrichment protocol coupled to high-sensitivity immuno-detection was developed. The immuno-enrichment protocol was first validated using human AD post-mortem brain material. Side-by-side comparison of untreated brain homogenate samples with Tau immuno-enriched samples revealed that at corresponding concentrations, the limit of detection of the Tau13/ACI-35-2G5-Ab3 ALPHALISA™ assay was reached at 0.5 µg/mL for the untreated samples and at between 0.002-0.006 µg/mL for the immuno-enriched samples, indicating a 100-fold enrichment (FIG. 9).

Figure 10:
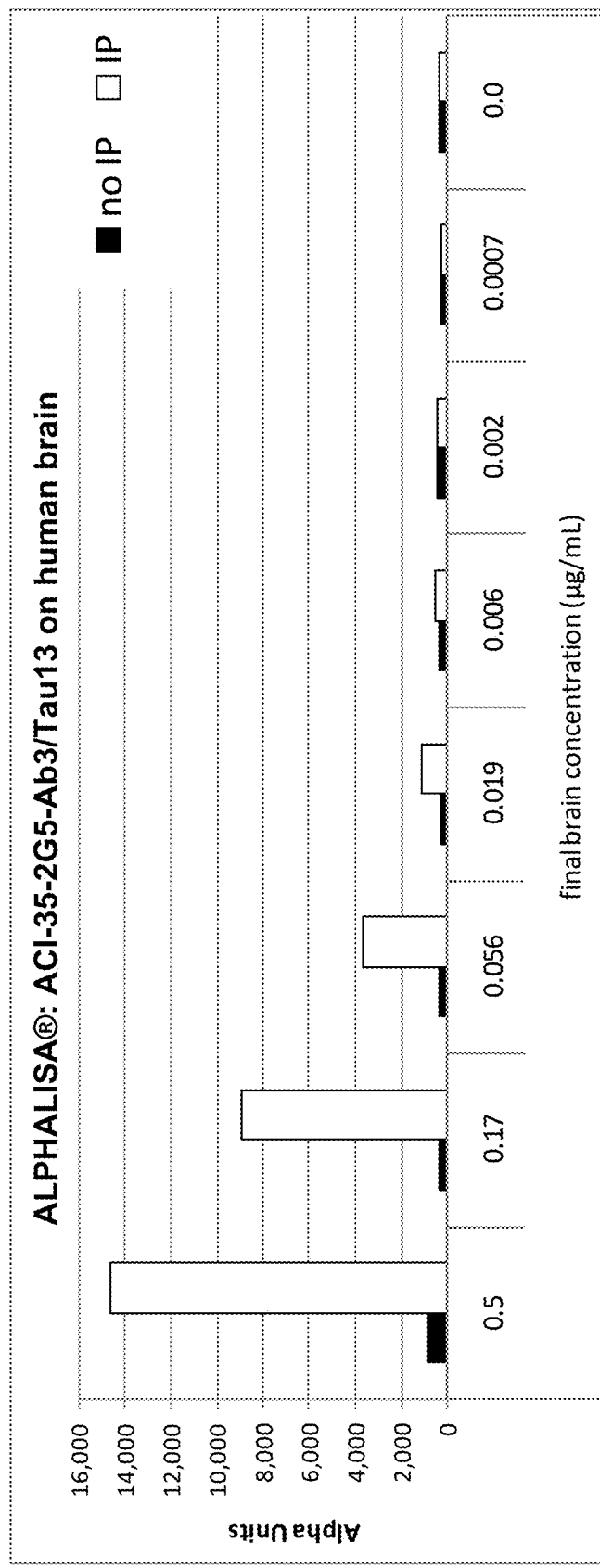
FIG. 10 shows results of detection of Tau-pS396 in human AD and control (Ctrl) CSF by ACI-35-2G5-Ab3 antibody using IP followed by ALPHALISA™. *** p=0.0003 by Mann-Whitney test.

Next, the immuno-enrichment protocol was applied on the live-donor CSF samples (n=17 for mild-to-moderate AD patients and n=16 for age-matched healthy volunteers). The data obtained (FIG. 10) demonstrate that: a) following the immuno-enrichment protocol the Tau13/ACI-35-2G5-Ab3 ALPHALISA™ detected pS396-Tau in all human CSF samples; and b) more importantly, a significant increased in the amount of pS396-Tau in AD CSF was observed when compared to the control (p=0.0003, Mann-Whitney test).

In conclusion, an immuno-enrichment/immuno-detection protocol was developed, allowing for the detection of pS396-Tau in human CSF. Increase of pS396-Tau in CSF of mild-to-moderate AD suggests that this method could be successfully used in clinical biomarker studies to assess disease progression, patient stratification and therapy efficacy. ACI-35-2G5-Ab3 antibody detected pS396-Tau in all human CSF samples, and more importantly, the antibody was able to discriminate AD CSF when compared to the control.

TABLE 1

Tau sequence, vaccine and antibody description

| Description | Vaccine | Sequence*, length (n), sequence ID number | Hybridoma | Antibodies |
|---|---|---|---|---|
| T3: Tau 393-408 [pS396, pS404] | ACI-35 | VYKS(p)PVVSGDTS(p)PRHL (n = 16) (SEQ ID NO: 62) | A4-4A6-48 | ACI-35-4A6-Ab2 |
| | | | A6-2G5-30 | ACI-35-2G5-Ab2 |
| | | | A6-2G5-41 | ACI-35-2G5-Ab3 |
| | | | A4-2A1-18 | ACI-35-2A1-Ab1 |
| | | | A4-2A1-40 | ACI-35-2A1-Ab2 |
| | | | A6-1D2-12 | ACI-35-1D2-Ab1 |
| | | | A4-4A6-18 | ACI-35-4A6-Ab1 |
| | | | A6-2G5-08 | ACI-35-2G5-Ab1 |

*Based on the longest isoform of human Tau (Tau441). p indicates phosphorylated residue.

TABLE 2

Screening of hybridomas for binding to target

| | | ELISA | | | | | |
|---|---|---|---|---|---|---|---|
| Hybridoma | Antibodies | Tau p-peptide | Tau peptide | Full-length pTau | Full-length Tau | TAUPIR | Western Blot |
| A4-2A1-18 | ACI-35-2A1-Ab1 | + | − | + | − | +++ | + |
| A4-2A1-40 | ACI-35-2A1-Ab2 | + | − | + | − | +++ | + |
| A4-4A6-18 | ACI-35-4A6-Ab1 | + | − | − | + | − | + |
| A6-1D2-12 | ACI-35-1D2-Ab1 | + | − | + | − | ++ | −/+ |
| A6-2G5-08 | ACI-35-2G5-Ab1 | + | − | − | − | − | −/+ |
| A6-2G5-30 | ACI-35-2G5-Ab2 | + | − | + | − | ++ | + |

TABLE 2-continued

Screening of hybridomas for binding to target

| Hybridoma | Antibodies | ELISA Tau p-peptide | Tau peptide | Full-length pTau | Full-length Tau | TAUPIR | Western Blot |
|---|---|---|---|---|---|---|---|
| A6-2G5-41 | ACI-35-2G5-Ab3 | + | − | + | − | ++ | + |

The intensity of binding can be compared only within the same column, within the same assay (ELISA, or TAUPIR, or WB).
− Not good binding or absent; + Good binding; ++ Very good binding; +++ Great binding (better than very good binding)

TABLE 3

Binding affinity of anti-tau antibodies

| Hybridoma | Antibodies | Association rate constant ($k_d$) (1/Ms) | Dissociation rate constant ($k_a$) (1/s) | Dissociation constant ($K_D$) (nM) |
|---|---|---|---|---|
| A4-4A6-18 | ACI-35-4A6-Ab1 | $2.00 \times 10^5$ | $3.10 \times 10^{-3}$ | 16 [a] |
|  |  | $1.10 \times 10^5$ | $1.70 \times 10^{-3}$ | 15 [b] |
| A6-1D2-12 | ACI-35-1D2-Ab1 | $1.60 \times 10^3$ | $9.30 \times 10^{-6}$ | ≤6 [a] |
|  |  | $2.20 \times 10^4$ | $1.80 \times 10^{-3}$ | 82 [b] |
| A6-2G5-08 | ACI-35-2G5-Ab1 | $4.80 \times 10^5$ | $5.30 \times 10^{-3}$ | 10 [a] |
|  |  | $3.20 \times 10^4$ | $2.20 \times 10^{-3}$ | 70 [b] |
| A6-2G5-30 | ACI-35-2G5-Ab2 | $2.40 \times 10^4$ | $2.30 \times 10^{-4}$ | 10 [b] |
| A6-2G5-41 | ACI-35-2G5-Ab3 | $1.70 \times 10^4$ | $3.80 \times 10^{-5}$ | 2 [b] |
| A4-2A1-18 | ACI-35-2A1-Ab1 | $2.70 \times 10^4$ | $1.00 \times 10^{-3}$ | 38 [b] |
| A4-2A1-40 | ACI-35-2A1-Ab2 | $3.00 \times 10^4$ | $9.00 \times 10^{-4}$ | 30 [b] |

[a] Analyses performed with a Phospho-peptide purity of 64% by HPLC.
[b] Analyses performed with a Phospho-peptide purity of 87% by HPLC.

TABLE 4

Description of the AD subjects used for this study

| AD subject ID | Gender | Age at death | Age at diagnosis | Disease duration | AD Braak stage |
|---|---|---|---|---|---|
| AD 18 | F | 82 | 66 | 16 | Braak V |
| AD 19 | F | 81 | 77 | 4 | Braak V |
| AD 20 | M | 88 | 82 | 6 | Braak V |
| AD 21 | F | 82 | 77 | 5 | Braak VI |
| AD 22 | M | 62 | 49 | 13 | Braak V |
| AD 23 | F | 76 | 65 | 11 | Braak VI |
| AD 24 | F | 86 | 84 | 2 | Braak V |
| AD 25 | M | 81 | 78 | 3 | Braak V |
| AD 26 | F | 88 | 83 | 5 | Braak V |
| AD 27 | F | 85 | 82 | 3 | Braak V |

TABLE 5

Tau amino acids and phospho-residues required for antibody binding.

| Hybridoma | Antibody | Epitope* |
|---|---|---|
| A4-2A1-18 | ACI-35-2A1-Ab1 | Tau aa 393-401, with requirement for pS396 |
| A4-2A1-40 | ACI-35-2A1-Ab2 | Tau aa 393-401, with requirement for pS396 |
| A4-4A6-18 | ACI-35-4A6-Ab1 | Tau aa 396-401, with requirement for pS396 |
| A6-1D2-12 | ACI-35-1D2-Ab1 | Tau aa 394-400, with requirement for pS396 |
| A6-2G5-08 | ACI-35-2G5-Ab1 | Tau aa 402-406, with requirement for pS404 |
| A6-2G5-30 | ACI-35-2G5-Ab2 | Tau aa 393-400, with requirement for pS396 |
| A6-2G5-41 | ACI-35-2G5-Ab3 | Tau aa 393-400, with requirement for pS396 |

*Based on the longest isoform of human Tau (Tau441)

TABLE 6

Amino Acid Sequence of the heavy chain and light chain variable regions (VH and VK) and the CDRs

| Antibody | Hybridoma | VH | VK | VH CDR1 | VH CDR2 | VH CDR3 | VK CDR1 | VK CDR2 | VK CDR3 |
|---|---|---|---|---|---|---|---|---|---|
| ACI-35-4A6-Ab1 | A4-4A6-18 | QVQLQQPGAELLKPGASVKLSCKASGYTFTSYWMHWVKQRPGRGLEWIGRIDPNSDRTKYNEKFKRKATLTVDKSSSTAYMQLSSLTSEDSAVYYCARDDYAWFAYWGQGTLVTVSA (SEQ ID NO: 68) | DVLMTQTPLSLPVSLGDQASISCRSSQSIVHSNGNTYLEWYLQKPGQSPKLLIYKLSNRFSGVPDRFSGSGSGTDFTLKISRVEAEDLGVYYCFQGSHVPPTFGGGTKLEIK (SEQ ID NO: 69) | GYTFTSYWMH (SEQ ID NO: 70) | RIDPNSDRTKYNEKFKR (SEQ ID NO: 71) | DDYAWFAY (SEQ ID NO: 72) | RSSQSIVHSNGNTYLE (SEQ ID NO: 73) | KLSNRFS (SEQ ID NO: 74) | FQGSHVPPT (SEQ ID NO: 75) |
| ACI-35-1D2-Ab1 | A6-1D2-12 | QVTLKESGPGILQSSQTLSLTCSFSGFSLSTSGMGVSWIRQPSGKGLEWLAHIYWDDDKRYNASLKSRLTISKDTSRNQVFLKITCVDTADTATYYCARLL | NILMTQSPSSLAVSAGEKVTMSCKSSQSVLYSSNQKNYLAWYQQKPGQSPKLLIYWASTRESGVPDRFTGSGSGTDFTLTISSVQAEDLAVYYCLQYLS | GFSLSTSGMGVS (SEQ ID NO: 78) | HIYWDDDKRYNASLKS (SEQ ID NO: 79) | LLRPYALDY (SEQ ID NO: 80) | KSSQSVLYSSNQKNYLA (SEQ ID NO: 81) | WASTRES (SEQ ID NO: 82) | LQYLSSLT (SEQ ID NO: 83) |

TABLE 6-continued

Amino Acid Sequence of the heavy chain and light chain variable regions (VH and VK) and the CDRs

| Anti-body | Hybridoma | VH | VK | VH CDR1 | VH CDR2 | VH CDR3 | VK CDR1 | VK CDR2 | VK CDR3 |
|---|---|---|---|---|---|---|---|---|---|
| | | RPYALDYWGQGTSVTV SS (SEQ ID NO: 76) | SLTFGAGTKLELK (SEQ ID NO: 77) | | | | | | |
| ACI-35-2A1-Ab1 | A4-2A1-18 | EVQLQQSGPELVKPGA SVKISCKASGYTFTDYY MNWVKQSHGKSLEWIG DINPNNGGTSYNQKFK GKATLTVDKSSSTAYM ELRSLTSEDSAVYYCVR EGRFAYWGHGTLVTVS A (SEQ ID NO: 88) | DIVMTQAAPSVPVTPGE SVSISCRSSKSLLHSNG NTYLYWFLQRPGQSPQ LLIHRMSNLASGVPDRF SGSGSGTAFTLRISRVE AEDVGVYYCMQHLKSP YTFGGGTKLEIK (SEQ ID NO: 116) | GYTFTD YYMN (SEQ ID NO: 89) | DINPNN GGTSYN QKFKG (SEQ ID NO: 90) | EGRFA Y (SEQ ID NO: 91) | RSSKSLL HSNGNT YLY (SEQ ID NO: 93) | RMSNLA S (SEQ ID NO: 94) | MQHLKS PYT (SEQ ID NO: 95) |
| ACI-35-2A1-Ab2 | A4-2A1-40 | EVQLQQSGPELVKPGA SVKISCKASGYTFTDYY MNWVKQSHGKSLEWIG DINPNNGGTSYNQKFK GKATLTVDKSSSTAYM ELRSLTSEDSAVYYCVR EGRFAYWGHGTLVTVS A (SEQ ID NO: 88) | DIX*MTQAAPSVPVTPG ESVSISCRSSKSLLHSN GNTYLYWFLQRPGQSP QLLIYRMSNLASGVPDR FSGSGSGTAFTLRISRV EAEDVGVYYCMQHLKS PYTFGGGTKLEIK (SEQ ID NO: 92) *X = M or V | GYTFTD YYMN (SEQ ID NO: 89) | DINPNN GGTSYN QKFKG (SEQ ID NO: 90) | EGRFA Y (SEQ ID NO: 91) | RSSKSLL HSNGNT YLY (SEQ ID NO: 93) | RMSNLA S (SEQ ID NO: 94) | MQHLKS PYT (SEQ ID NO: 95) |
| ACI-35-A46-Ab2 | A4-4A6-48 | EVQLQQSGPELVKPGA SVKISCKASGYTFTDYY MNWVKQSHGKSLEWIG DINPNNGGTSYNQKFK GKATLTVDKSSSTAYM ELRSLTSEDSAVYYCVR EGRFAYWGHGTLVTVS A (SEQ ID NO: 88) | DIVMTQAAPSVPVTPGE SVSISCRSSKSLLHSNG NTYLYWFLQRPGQSPQ LLIYRMSNLASGVPDRF SGSGSGTAFTLRISRVE AEDVGVYYCMQHLKSP YTFGGGTKLEIK (SEQ ID NO: 118) | GYTFTD YYMN (SEQ ID NO: 89) | DINPNN GGTSYN QKFKG (SEQ ID NO: 90) | EGRFA Y (SEQ ID NO: 91) | RSSKSLL HSNGNT YLY (SEQ ID NO: 93) | RMSNLA S (SEQ ID NO: 94) | MQHLKS PYT (SEQ ID NO: 95) |
| ACI-35-2G5-Ab1 | A6-2G5-08 | QVQLKQSGAELVRPGA SVKLSCKASGYTFTDYY INWVKQRPGQGLEWIA RIYPGRGNIYYNEKFKG KATLTAEKSSSTAYMQL SSLTSEDSAVYFCARF WDVTYWGQGTLVTVSA (SEQ ID NO: 96) | DVLMTQTPLSLPVSLGD QASISCRSSQSIVHSNG NTYLEWFLQKPGQSPK LLIYKVSNRFSGVPDRF SGSGSGTDFTLKISRVE AEDLGVYYCFQGSHVP YTFGGGTKLEIK (SEQ ID NO: 97) | GYTFTD YYIN (SEQ ID NO: 98) | RIYPGR GNIYYN EKFKG (SEQ ID NO: 99) | FWDVT Y (SEQ ID NO: 100) | RSSQSIV HSNGNT YLE (SEQ ID NO: 101) | KVSNRF S (SEQ ID NO: 102) | FQGSHV PYT (SEQ ID NO: 103) |
| ACI-35-2G5-Ab2 | A6-2G5-30 | EVQLQQSGPELVKPGA SVKISCKASGFTFTDYY MNWVKQSHGKSLEWIG DINPNNGGTSYHQKFK GKATLTVDKSSSTAYM ELRSLTSEDSAVYYCVR EGRFAYWGHGTLVTVS A (SEQ ID NO: 104) | DIVMTQSQKFMSTSVG DRVSVTCKASQNVGTN VAWYQQKPGQSPKALI YSASYRYSGVPDRFTG SGSGTDFTLTISNVQSE DLAEYFCQQYNSYPYT FGGGTKLEIK (SEQ ID NO: 105) | GFTFTD YYMN (SEQ ID NO: 89) | DINPNN GGTSYH QKFKG (SEQ ID NO: 115) | EGRFA Y (SEQ ID NO: 91) | KASQNV GTNVA (SEQ ID NO: 106) | SASYRY S (SEQ ID NO: 107) | QQYNSY PYT (SEQ ID NO: 108) |
| ACI-35-2G5-Ab3 | A6-2G5-41 | EVQLQQSGPELVKPGA SVKISCKASGFTFTDYY MNWVKQSHGKSLEWIG DINPNNGGTSYHQKFK GKATLTVDKSSSTAYM ELRSLTSEDSAVYYCVR EGRFAYWGQGTLVTVS A (SEQ ID NO: 104) | DIVMTQSQKFMSTSVG DRVSVTCKASQNVGTN VAWYQQKPGQSPKALI YSASYRYSGVPDRFTG SGSGTDFTLTISNVQSE DLAEYFCQQYNSYPYT FGGGTKLEIK (SEQ ID NO: 105) | GFTFTD YYMN (SEQ ID NO: 89) | DINPNN GGTSYH QKFKG (SEQ ID NO: 115) | EGRFA Y (SEQ ID NO: 91) | KASQNV GTNVA (SEQ ID NO: 106) | SASYRY S (SEQ ID NO: 107) | QQYNSY PYT (SEQ ID NO: 108) |

TABLE 7

Nucleotide Sequence of the heavy chain and light chain variable regions (VH and VK)

| Antibody | Hybridoma | VH | VK |
|---|---|---|---|
| ACI-35 4A6-Ab1 | A4-4A6-18 | CAGGTCCAACTGCAGCAGCCTGGGGCTGAGCTTCT GAAGCCTGGGGCTTCAGTGAAACTGTCCTGCAAGG CTTCTGGCTACACCTTCACCGACTACTGGATGCACT GGGTGAAGCAGAGGCCTGGACGAGGCCTTGAGTG GATTGGAAGGATTGATCCTAATAGTGATCGTACTAA GTACAATGAGAAGTTCAAGCGCAAGGCCACACTGA CTGTAGACAAATCCTCCAGCACAGCCTACATGCAGC TCAGCAGCCTGACATCTGAGGACTCTGCGGTCTATT | GATGTTTTGATGACCCAAACTCCACTCTCCCTGCCTGTC AGTCTTGGAGATCAAGCCTCCATCTCTTGCAGATCTAGT CAGAGCATTGTACATAGTAATGGAAACACCTATTTAGAAT GGTACCTGCAGAAACCAGGCCAGTCTCCAAAGCTCCTG ATCTACAAATTTCCAACCGATTTTCTGGGGTCCCAGAC AGGTTCAGTGGCAGTGGATCAGGGACAGATTTCACACT CAAGATCAGCAGAGTGGAGGCTGAGGATCTGGGAGTTT ATTACTGCTTTCAAGGTTCACATGTTCCTCCGACGTTCG |

TABLE 7-continued

Nucleotide Sequence of the heavy chain and light chain variable regions (VH and VK)

| Antibody | Hybridoma | VH | VK |
|---|---|---|---|
| | | ATTGTGCAAGGGATGATTACGCCTGGTTTGCTTACT GGGGCCAAGGGACTCTGGTCACTGTCTCTGCA (SEQ ID NO: 84) | GTGGAGGCACCAAGCTGGAAATCAAA (SEQ ID NO: 85) |
| ACI-35-1D2-Ab1 | A6-1D2-12 | CAGGTTACTCTGAAAGAGTCTGGCCCTGGGATATTG CAGTCCTCCCAGACCCTCAGTCTGACTTGTTCTTTC TCTGGGTTTTCACTGAGCACTTCTGGTATGGGTGTG AGCTGGATTCGTCAGCCTTCAGGAAAGGGTCTGGA GTGGCTGGCACACATTTACTGGGATGATGACAAGC GCTATAACGCATCCCTGAAGAGCCGGCTCACAATCT CCAAGGATACCTCCAGAAACCAGGTATTCCTCAAGA TCACCTGTGTGGACACTGCAGATACTGCCACATACT ACTGTGCTCGGTTACTGCGTCCTTATGCTTTGGACT ACTGGGGTCAAGGAACCTCAGTCACCGTCTCCTCA (SEQ ID NO: 86) | AACATTTTGATGACACAGTCGCCATCATCTCTGGCTGTG TCTGCAGGAGAAAAGGTCACTATGAGCTGTAAGTCCAGT CAAAGTGTTTTATACAGTTCAAATCAGAAGAACTACTTGG CCTGGTACCAGCAGAAACCAGGGCAGTCTCCTAAACTG CTGATCTACTGGGCATCCACTAGGGAATCTGGTGTCCCT GATCGCTTCACAGGCAGTGGATCTGGGACAGATTTTACT CTTACCATCAGCAGTGTACAAGCTGAAGACCTGGCAGTT TATTACTGTCTTCAATACCTCTCCTCGCTCACGTTCGGTG CTGGGACCAAGCTGGAGCTGAAA (SEQ ID NO: 87) |
| ACI-35-2A1-Ab1 | A4-2A1-18 | GAGGTCCAGCTGCAACAATCTGGACCTGAGCTGGT GAAGCCTGGGGCTTCAGTGAAGATATCCTGTAAGG CTTCTGGATACACGTTCACTGACTACTACATGAACT GGGTGAAGCAGAGCCATGGAAAGAGCCTTGAGTGG ATTGGAGATATTAATCCTAACAATGGTGGTACTAGC TACAACCAGAAGTTCAAGGGCAAGGCCACATTGACT GTAGACAAGTCCTCCAGCACAGCCTACATGGAGCT CCGCAGTCTGACATCTGAGGACTCTGCAGTCTATTA TTGTGTAAGAGAGGGGCGGTTTGCTTACTGGGGTC ATGGGACTCTGGTCACTGTCTCTGCA (SEQ ID NO: 109) | GATATTGTGATGACTCAGGCTGCACCCTCTGTACCTGTC ACTCCTGGAGAGTCAGTATCCATCTCCTGCAGGTCTAGT AAGAGTCTCCTGCATAGTAATGGCAACACTTACTTGTATT GGTTCCTGCAGAGGCCAGGCCAGTCTCCTCAGCTCCTG ATACATCGGATGTCCAACCTTGCCTCAGGAGTCCCAGAC AGGTTCAGTGGCAGTGGGTCAGGAACTGCTTTCACACT GAGAATCAGTAGAGTGGAGGCTGAGGATGTGGGTGTT ATTACTGTATGCAACATCTAAATCTCCGTACACGTTCGG AGGGGGGACCAAGCTGGAAATAAAA (SEQ ID NO: 117) |
| ACI-35-2A1-Ab2 | A4-2A1-40 | GAGGTCCAGCTGCAACAATCTGGACCTGAGCTGGT GAAGCCTGGGGCTTCAGTGAAGATATCCTGTAAGG CTTCTGGATACACGTTCACTGACTACTACATGAACT GGGTGAAGCAGAGCCATGGAAAGAGCCTTGAGTGG ATTGGAGATATTAATCCTAACAATGGTGGTACTAGC TACAACCAGAAGTTCAAGGGCAAGGCCACATTGACT GTAGACAAGTCCTCCAGCACAGCCTACATGGAGCT CCGCAGTCTGACATCTGAGGACTCTGCAGTCTATTA TTGTGTAAGAGAGGGGCGGTTTGCTTACTGGGGTC ATGGGACTCTGGTCACTGTCTCTGCA (SEQ ID NO: 109) | GATATTR*TGATGACTCAGGCTGCACCCTCTGTACCTGT CACTCCTGGAGAGTCAGTATCCATCTCCTGCAGGTCTAG TAAGAGTCTCCTGCATAGTAATGGCAACACTTACTTGTAT TGGTTCCTGCAGAGGCCAGGCCAGTCTCCTCAGCTCCT GATATATCGGATGTCCAACCTTGCCTCAGGAGTCCCAGA CAGGTTCAGTGGCAGTGGGTCAGGAACTGCTTTCACAC TGAGAATCAGTAGAGTGGAGGCTGAGGATGTGGGTGTT TATTACTGTATGCAACATCTAAATCTCCGTACACGTTCG GAGGGGGGACCAAGCTGGAAATAAAA (SEQ ID NO: 110) R* = A or G |
| ACI-35-4A6-Ab2 | A4-4A6-48 | GAGGTCCAGCTGCAACAATCTGGACCTGAGCTGGT GAAGCCTGGGGCTTCAGTGAAGATATCCTGTAAGG CTTCTGGATACACGTTCACTGACTACTACATGAACT GGGTGAAGCAGAGCCATGGAAAGAGCCTTGAGTGG ATTGGAGATATTAATCCTAACAATGGTGGTACTAGC TACAACCAGAAGTTCAAGGGCAAGGCCACATTGACT GTAGACAAGTCCTCCAGCACAGCCTACATGGAGCT CCGCAGTCTGACATCTGAGGACTCTGCAGTCTATTA TTGTGTAAGAGAGGGGCGGTTTGCTTACTGGGGTC ATGGGACTCTGGTCACTGTCTCTGCA (SEQ ID NO: 109) | GATATTGTGATGACTCAGGCTGCACCCTCTGTACCTGTC ACTCCTGGAGAGTCAGTATCCATCTCCTGCAGGTCTAGT AAGAGTCTCCTGCATAGTAATGGCAACACTTACTTGTATT GGTTCCTGCAGAGGCCAGGCCAGTCTCCTCAGCTCCTG ATATATCGGATGTCCAACCTTGCCTCAGGAGTCCCAGAC AGGTTCAGTGGCAGTGGGTCAGGAACTGCTTTCACAC TGAGAATCAGTAGAGTGGAGGCTGAGGATGTGGGTGTT ATTACTGTATGCAACATCTAAATCTCCGTACACGTTCGG AGGGGGGACCAAGCTGGAAATAAAA (SEQ ID NO: 119) |
| ACI-35-2G5-Ab1 | A6-2G5-08 | CAGGTCCAGCTGAAGCAGTCTGGGGCTGAGCTGGT GAGGCCTGGGGCTTCAGTGAAGATGTCCTGCAAGG CTTCTGGCTACACTTTCACTGACTACTATATAAACTG GGTGAAGCAGAGGCCTGGACAGGGACTTGAGTGGA TTGCAAGGATTTATCCTGGAAGAGGTAATATTTACTA CAATGAGAAGTTCAAGGGCAAGGCCACACTGACTG CAGAAAAATCCTCCAGCACTGCCTACATGCAGCTCA GCAGCCTGACATCTGAGGACTCTGCTGTCTATTTCT GTGCAAGATTCTGGGACGTGACTTACTGGGGCCAA GGGACTCTGGTCACTGTCTCTGCA (SEQ ID NO: 111) | GATGTTTTGATGACCCAAACTCCACTCTCCCTGCCTGTC AGTCTTGGAGATCAAGCCTCCATCTCTTGCAGATCTAGT CAGAGCATTGTACATAGTAATGGAAACACCTATTTAGAAT GGTTCCTGCAGAAACCAGGCCAGTCTCCAAAGCTCCTG ATCTACAAAGTTTCCAACCGATTTTCTGGGGTCCCAGAC AGGTTCAGTGGCAGTGGATCAGGGACAGATTTCACACT CAAGATCAGCAGAGTGGAGGCTGAGGATCTGGGAGTTT ATTACTGCTTTCAAGGTTCACATGTTCCGTACACGTTCG GAGGGGGGACCAAGCTGGAAATAAAA (SEQ ID NO: 112) |
| ACI-35-2G5-Ab2 | A6-2G5-30 | GAGGTCCAGCTGCAACAATCTGGACCTGAGCTGGT GAAGCCTGGGGCTTCAGTGAAGATATCCTGTAAGG CTTCTGGATACACGTTCACTGACTACTACATGAACT GGGTGAAGCAGAGCCATGGAAAGAGCCTTGAGTGG ATTGGAGATATTAATCCTAACAATGGTGGTACTAGC TACCACCAGAAGTTCAAGGGCAAGGCCACATTGACT GTAGACAAGTCCTCCAGCACAGCCTACATGGAGCT CCGCAGCCTGACATCTGAGGACTCTGCAGTCTATTA CTGTGTAAGAGAGGAAGATTTGCTTACTGGGGCCA AGGGACTCTGGTCACTGTCTCTGCA (SEQ ID NO: 113) | GACATTGTGATGACCCAGTCTCAAAAATTCATGTCCACA TCAGTAGGAGACAGGGTCAGCGTCACCTGCAAGGCCAG TCAGAATGTGGGTACTAATGTAGCCTGGTATCAACAGAA ACCAGGGCAATCTCCTAAAGCACTGATTTACTCGGCATC CTACCGGTACAGTGGAGTCCCTGATCGCTTCACAGGCA GTGGATCTGGGACAGATTTCACTCTCACCATCAGCAATG TGCAGTCTGAAGACTTGGCAGATTATTTCTGTCAGCAAT ATAACAGCTATCCGTACACGTTCGGAGGGGGGACCAAG CTGGAAATAAAA (SEQ ID NO: 114) |

TABLE 7-continued

Nucleotide Sequence of the heavy chain and light chain variable regions (VH and VK)

| Antibody | Hybridoma | VH | VK |
|---|---|---|---|
| ACI-35-2G5-Ab3 | A6-2G5-41 | GAGGTCCAGCTGCAACAATCTGGACCTGAGCTGGT GAAGCCTGGGGCTTCAGTGAAGATATCCTGTAAGG CTTCTGGATTCACGTTCACTGACTACTACATGAACT GGGTGAAGCAGAGCCATGGAAAGAGCCTTGAGTGG ATTGGAGATATTAATCCTAACAATGGTGGTACTAGC TACCACCAGAAGTTCAAGGGCAAGGCCACATTGACT GTAGACAAGTCCTCCAGCACAGCCTACATGGAGCT CCGCAGCCTGACATCTGAGGACTCTGCAGTCTATTA CTGTGTAAGAGGGAAGATTTGCTTACTGGGGCC AAGGGACTCTGGTCACTGTCTCTGCA (SEQ ID NO: 113) | GACATTGTGATGACCCAGTCTCAAAAATTCATGTCCACA TCAGTAGGAGACAGGGTCAGCGTCACCTGCAAGGCCAG TCAGAATGTGGGTACTAATGTAGCCTGGTATCAACAGAA ACCAGGGCAATCTCCTAAAGCACTGATTTACTCGGCATC CTACCGGTACAGTGGAGTCCCTGATCGCTTCACAGGCA GTGGATCTGGGACAGATTTCACTCTCACCATCAGCAATG TGCAGTCTGAAGACTTGGCAGAGTATTTCTGTCAGCAAT ATAACAGCTATCCGTACACGTTCGGAGGGGGGACCAAG CTGGAAATAAAA (SEQ ID NO: 114) |

TABLE 8

Primers used for CDR sequencing of antibody variable regions

| Subclone | Ab isotype | | Primer sequences | SEQ ID NO |
|---|---|---|---|---|
| A4-4A6-48 | IgG2b | VH primers | 5' ACTAGTCGACATGGGATGGAGCTTATCATGTTCTT | 193 |
| | | | ACTAGTCGACATGGGATGGAGCTTATCATGCTCTT | 194 |
| | | | GGGAATTCATGGAATGCACCTGGGTTTTCCTCTT | 137 |
| | | | GGGAATTCATGGAATGGACCTGGGTTTTCCTCTT | 195 |
| | | | GGGAATTCATGGAATGGACCTGGGTCTTTCTCTT | 196 |
| | | | GGGAATTCATGGAAATGGAGCTGGGTTATTCTCTT | 197 |
| | | | GGGAATTCATGGAATGCAGCTGGGTTATTCTCTT | 151 |
| | | | GGGAATTCATGGAATGGAGCTGGGTCTTTCTCTT | 121 |
| | | | 3' CCCAAGCTTCCAGGGGCCAATGGATAGACGATGG | 198 |
| | | | CCCAAGCTTCCAGGGACCAAGGGATAGACGGATGG | 199 |
| | | | CCCAAGCTTCCAGGGACCAAGGGATAGACGATGG | 200 |
| | | | CCCAAGCTTCCAGGGGCCAATGGATAACGGTGG | 141 |
| | | | CCCAAGCTTCCAGGGACCAGTGGATAAACGATGG | 166 |
| | | | CCCAAGCTTCCAGGGACCAATGGATAAACGGATGG | 131 |
| | | | CCCAAGCTTCCAGGGACCAAGGGATAAACGGATGG | 144 |
| | | VK primers | 5' ACTAGTCGACATGATGTACCCGGCTCAGTTTCTGGG | 201 |
| | | | ACTAGTCGACATGAGGACTTCGATTCAGTTCTTGGG | 202 |
| | | | ACTAGTCTACATGAAGTTGCCTGTTAGGCTGTTGGTGCT | 203 |
| | | | ACTAGTCGACATGAAGTTGTCTGTTAGGCTGTTGGTGCT | 204 |
| | | | ACTAGTCGACATGAAGTTGCCTGTTAGGCTGTTGGTGCT | 50 |
| | | | 3' CCCAAGCTTACTGGATGGTGGGAAGATGGA | 51 |
| A4-4A6-18 | IgG2b | VH primers | 5' ATGGGATGGAGCTRTATCATSYTCTT | 205 |
| | | | ATGAAGWTGTGGBTRAACTGGRT | 206 |
| | | | ATGGRATGGASCKKIRTCTTTMTCT | 207 |
| | | | 3' CCAGGGRCCARKGGATARACIGRTGG | 208 |
| | | VK primers | 5' ATGGAGACAGACACACTCCTGCTAT | 209 |
| | | | ATGGAGWCAGACACACTSCTGYTATGGGT | 210 |
| | | | ATGAAGTTGCCTGTTAGGCTGTTGGTGCT | 211 |
| | | | ATGGATTTWCARGTGCAGATTWTCAGCTT | 212 |
| | | | ATGGTYCTYATVTCCTTGCTGTTCTGG | 213 |
| | | | ATGGTYCTYATVTTRCTGCTGCTATGG | 214 |
| | | | 3' ACTGGATGGTGGGAAGATGGA | 215 |
| A6-1D2-12 | IgG2a | VH primers | 5' ATGAAATGCAGCTGGRTYATSTTCTT | 216 |
| | | | ATGGRCAGRCTTACWTYYTCATTCCT | 217 |
| | | | ATGATGGTGTTAAGTCTTCTGTACCT | 218 |
| | | | 3' CCAGGGRCCARKGGATARACIGRTGG | 208 |
| | | VK primers | 5' ATGRAGWCACAKWCYCAGGTCTTT | 219 |
| | | | ATGGAGACAGACACACTCCTGCTAT | 209 |
| | | | ATGGAGWCAGACACACTSCTGYTATGGGT | 210 |
| | | | ATGAGGRCCCCTGCTCAGWTTYTTGGIWTCTT | 220 |
| | | | ATGGGCWTCAAGATGRAGTCACAKWYYCWGG | 221 |
| | | | ATGAAGTTGCCTGTTAGGCTGTTGGTGCT | 211 |
| | | | ATGGATTTWCARGTGCAGATTWTCAGCTT | 212 |

TABLE 8-continued

Primers used for CDR sequencing of antibody variable regions

| Subclone | Ab isotype | | Primer sequences | SEQ ID NO |
|---|---|---|---|---|
| | | | ATGGTYCTYATVTCCTTGCTGTTCTGG | 213 |
| | | | ATGGTYCTYATVTTRCTGCTGCTATGG | 214 |
| | | 3' | ACTGGATGGTGGGAAGATGGA | 215 |
| A4-2A1-18 | IgG2b | VH primers 5' | GGGAATTCATGGAATGGAGCTGGGTCATTCTCTT | 136 |
| | | | GGGAATTCATGGAATGCAGCTGGGTTTTTCTCTT | 120 |
| | | | GGGAATTCATGGAATGGAGCTGGGTTTTTCTCTT | 123 |
| | | | GGGAATTCATGGAATGCACCTGGGTTTTCCTCTT | 137 |
| | | | GGGAATTCATGGAATGGAGCTGGGTCTTCCTCTT | 138 |
| | | | GGGAATTCATGGAATGGAGCTGGGTCATCCTCTT | 139 |
| | | | GGGAATTCATGGAATGGAGCTGGGTTATTCTCTT | 124 |
| | | | ACTAGTCGACATGGGATGAGCTTATCATCCTCTT | 140 |
| | | 3' | CCCAAGCTTCCAGGGGCCAATGGATAACGGTGG | 141 |
| | | | CCCAAGCTTCCAGGGACCAGTGGGATAAACGGGTGG | 142 |
| | | | CCCAAGCTTCCAGGGGCCAATGGATAAACGGGTGG | 134 |
| | | | CCCAAGCTTCCAGGGACCAAGGGATAGACGGGTGG | 143 |
| | | | CCCAAGCTTCCAGGGACCAAGGGATAAACGGATGG | 144 |
| | | | CCCAAGCTTCCAGGGACCAGGGGATAAACGGATGG | 145 |
| | | | CCCAAGCTTCCAGGGACCAATGGATAAACGGATGG | 131 |
| | | | CCCAAGCTTCCAGGGGCCAGGGATAAACGGGTGG | 146 |
| | | | CCCAAGCTTCCAGGGGCCAATGGATAAACCGGTGG | 147 |
| | | | CCCAAGCTTCCAGGGACCAGTGGATAAACGGTGG | 148 |
| | | VK primers 5' | ACTAGTCGACATGGTGTCCACAGCTCAGTTCCTTG | 149 |
| | | 3' | CCCAAGCTTACTGGATGGTGGGAAGATGGA | 51 |
| A4-2A1-40 | IgG2b | VH primers 5' | GGGAATTCATGGAATGGAGCTGGGTCATCCTCTT | 139 |
| | | | GGGAATTCATGGAATGCAGCTGGGTTTTCCTCTT | 154 |
| | | | GGGAATTCATGGAATGCAGCTGGGTCTTTCTCTT | 155 |
| | | | GGGAATTCATGGAATGGAGCTGGGTTTTCCTCTT | 127 |
| | | | GGGAATTCATGGAATGGAGCTGGGTCTTTCTCTT | 121 |
| | | | ACTAGTCGACATGGATGGAGCTTATCATCCTCTT | 175 |
| | | 3' | CCCAAGCTTCCAGGGACCAAGGGATAAACGGTGG | 176 |
| | | | CCCAAGCTTCCAGGGGCCAATGGATAAACCGGTGG | 147 |
| | | | CCCAAGCTTCCAGGGACCAATGGATAAACGATGG | 129 |
| | | | CCCAAGCTTCCAGGGGCCAGTGGATAAACGGGTGG | 177 |
| | | | CCCAAGCTTCCAGGGACCAATGGATAACGGGTGG | 128 |
| | | VK primers 5' | ACTAGTCGACATGAGGTACTCGGCTCAGTTCCTGGG | 178 |
| | | | ACTAGTCGACATGAGGTCCCCGGCTCAGTTCCTGGG | 179 |
| | | | ACTAGTCGACATGAGGACGTCGATTCAGTTCTTGGG | 180 |
| | | 3' | CCCAAGCTTACTGGATGGTGGGAAGATGGA | 51 |
| A6-2G5-08 | IgG2a | VH primers 5' | GGGAATTCATGGAATGCAGCTGGGTTTTTCTCTT | 120 |
| | | | GGGAATTCATGGAATGGAGCTGGGTCTTTCTCTT | 121 |
| | | | GGGAATTCATGGAATGCAGCTGGGTCATTCTCTT | 122 |
| | | | GGGAATTCATGGAATGGAGCTGGGTTTTTCTCTT | 123 |
| | | | GGGAATTCATGGAATGGAGCTGGGTTATTCTCTT | 124 |
| | | | GGGAATTCATGAAATGGAGCTGGGTCTTTTCTT | 125 |
| | | | GGGAATTCATGGAATGCAGCTGGGTCTTCCTCTT | 126 |
| | | | GGGAATTCATGGAATGGAGCTGGGTTTTCCTCTTC | 127 |
| | | 3' | CCCAAGCTTCCAGGGACCAATGGATAACGGGTGG | 128 |
| | | | CCCAAGCTTCCAGGGACCAATGGATAAACGATGG | 129 |
| | | | CCCAAGCTTCCAGGGACCAATGGATAAACGGTGG | 130 |
| | | | CCCAAGCTTCCAGGGACCAATGGATAAACGGATGG | 131 |
| | | | CCCAAGCTTCCAGGGACCAGTGGATAGACGGGTGG | 132 |
| | | | CCCAAGCTTCCAGGGACCAAGGGATAGATGATGG | 133 |
| | | | CCCAAGCTTCCAGGGGCCAATGGATAAACGGGTGG | 134 |
| | | | CCCAAGCTTCCAGGGGCCAATGGATAAACGATGG | 135 |
| | | VK primers 5' | ACTAGTCGACATGAAGTTGCCTGTTAGGCTGTTGGTGCT | 50 |
| | | 3' | CCCAAGCTTACTGGATGGTGGGAAGATGGA | 51 |
| A6-2G5-30 | IgG2b | VH primers 5' | GGGAATTCATGAAATGGAGCTGGGTCTTCCTCTT | 150 |
| | | | GGGAATTCATGGAATGCAGCTGGGTTATTCTCTT | 151 |
| | | | GGGAATTTATGGAATGGAGCTGGGTCTTCCTCTT | 152 |
| | | | GGGAATTCATGGAATGGAGCTGGGTTTTCCTCTT | 127 |
| | | | GGGAATTCATGGAATGCAGCTGGGTCATCCTCTT | 153 |

… TABLE 8-continued

Primers used for CDR sequencing of antibody variable regions

| Subclone | Ab isotype | | | Primer sequences | SEQ ID NO |
|---|---|---|---|---|---|
| | | | | GGGAATTCATGGAATGGAGCTGGGTTATTCTCTT | 124 |
| | | | | GGGAATTCATGGAATGCAGCTGGGTTTTCCTCTT | 154 |
| | | | | GGGAATTCATGGAATGCAGCTGGGTCTTTCTCTT | 155 |
| | | | | ACTAGTCGACATGGGATGGAGCTATATCATCCTCTT | 156 |
| | | | | ACTAGTCGACATGGGATGGAGCTTATCATCTTCTT | 157 |
| | | | | ACTAGTCGACATGTAGATGTGGTTAAACTGGGT | 158 |
| | | 3' | | CCCAAGCTTCCAGGGGCCAGGGGATAAACGGATGG | 159 |
| | | | | CCCAAGCTTCCAGGGGCCAAGGGATAGACGGATGG | 160 |
| | | | | CCCAAGCTTCCAGGGACCAGGGGATAGACGGGTGG | 161 |
| | | | | CCCAAGCTTCCAGGGACCAGGGGATAGACGGATGG | 162 |
| | | | | CCCAAGCTTCCAGGGGCCAGTGGATAAACGGATGG | 163 |
| | | | | CCCAAGCTTCCAGGGGCCAATGGATAACGATGG | 164 |
| | | | | CCCAAGCTTCCAGGGGCCAGTGGATAAACGATGG | 165 |
| | | | | CCCAAGCTTCCAGGGACCAATGGATAAACGGTGG | 130 |
| | | | | CCCAAGCTTCCAGGGACCAGTGGATAAACGATGG | 166 |
| | | | | CCCAAGCTTCCAGGGACCAATGGATAACGATGG | 167 |
| | | | | CCCAAGCTTCCAGGGACCATGGATAAACGGGTGG | 168 |
| | | VK primers | 5' | ACTAGTCGACATGGGCATCAAGATGAAGTCACATACTCTGG | 169 |
| | | | | ACTAGTCGACATGGGCATCAAGATGAGTCACATACTCTGG | 170 |
| | | | | ACTAGTCGACTGGGCATCAGATGAGTCACATACTCTGG | 171 |
| | | | | ACTAGTCGACATGGGCATCAAGATGAAGTCACAGACCCAGG | 172 |
| | | | | ACTAGTCGACATGGGCTTCAAGATGAAGTCACATTCTCTGG | 173 |
| | | | | ACTAGTCGACATGGGCTTCAAGATGAAGTCACATATTCAGG | 174 |
| | | | | CCCAAGCTTACTGGATGGTGGGAAGATGGA | 51 |
| | | 3' | | CCCAAGCTTACTGGATGGTGGGAAGATGGA | 51 |
| A6-2G5-41 | IgG2b | VH primers | 5' | GGGAATTCATGGAATGGACCTGGGTCATCCTCTT | 181 |
| | | | | GGGAATTCATGGAATGCAGCTGGGTTTTTCTCTT | 120 |
| | | | | GGGAATTCATGGAATGCAGCTGGGTTATCCTCTT | 182 |
| | | | | GGGAATTCATGGAATGGAGCTGGGTTATTCTCTT | 124 |
| | | | | GGGAATTCATGGAATGCAGCTGGGTCTTCCTCTT | 126 |
| | | | | GGGAATTCATGAATGGATCTGGGTTATTCTCTT | 183 |
| | | 3' | | CCCAAGCTTCCAGGGACCAGGGGATAAACGGGTGG | 184 |
| | | | | CCCAAGCTTCCAGGGACCAAGGGACGGGTGG | 185 |
| | | | | CCCAAGCTTCCAGGGACCAATGGATAAACAGATGG | 186 |
| | | | | CCCAAGCTTCCAGGGACCAAGGGATAAACGGATGG | 144 |
| | | | | CCCAAGCTTCCAGGGACCAGGGGATAAACGGATGG | 145 |
| | | | | CCCAAGCTTCCAGGGACCAAGGGATAAACGGGTGG | 187 |
| | | VK primers | 5' | GGGAATTCATGGAGACACATTCCCAGGTCTTT | 188 |
| | | | | GGGAATTCATGGAGTCACAGTCTCAGGTCTTT | 189 |
| | | | | ACTAGTCGACATGGGCTTCAAGATGGAGTCACATTTTCAGG | 190 |
| | | | | ACTAGTCGACATGGGCATCAAGATGAAGTCACATATTCAGG | 191 |
| | | | | ACTAGTCGACATGGGCTTCAAGATGAAGTCACATTCTCAGG | 192 |
| | | | | CCCAAGCTTACTGGATGGTGGGAAGATGGA | 51 |
| | | 3' | | CCCAAGCTTACTGGATGGTGGGAAGATGGA | 51 |

Degenerate Codons: R = A or G  S = C or G  D = A or G or T  B = C or G or T  Y = C or T  M = A or C  H = A or C or T  K = G or T  W = A or T  V = A or G or C

TABLE 9

Longest isoform of human Tau (441 aa), also called Tau40

| Longest isoform of human Tau (441 aa), also called Tau40 (SEQ ID NO: 67) Microtubule-associated protein tau isoform 2 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQARMVSK SKDGTGSDDK KAKGADGKTK IATPRGAAPP GQKGQANATR IPAKTPPAPK TPPSSGEPPK SGDRSGYSSP GSPGTPGSRS RTPSLPTPPT REPKKVAVVR TPPKSPSSAK SRLQTAPVPM PDLKNVKSKI GSTENLKHQP |
|---|---|
| [Homo sapiens] NCBI Reference Sequence: NP_005901.2 | GGGKVQIINK KLDLSNVQSK CGSKDNIKHV PGGGSVQIVY KPVDLSKVTS KCGSLGNIHH KPGGGQVEVK SEKLDFKDRV QSKIGSLDNI THVPGGGNKK IETHKLTFRE NAKAKTDHGA EIVYKSPVVS GDTSPRHLSN VSSTGSIDMV DSPQLATLAD EVSASLAKQG L (SEQ ID NO: 67) |

DEPOSITS

TABLE 10

The following hybridoma cell lines were deposited in the name of AC Immune SA, PSE-EPFL Building B, 1015 Lausanne/Switzerland and Katholieke Universiteit Leuven, Waaistraat 6 - Box 5105, 3000 Leuven/Belgium with the "Deutsche Sammlung von Mikroorganismen und Zellkulturen GmbH (DSMZ) in Braunschweig, Inhoffenstrasse 7 B, 38124 Braunschweig, under the provisions of the Budapest Treaty:

| Hybridoma name | Deposit number | Date of deposit |
|---|---|---|
| A4-4A6-48 | DSM ACC3136 | Aug. 30, 2011 |
| A6-2G5-30 | DSM ACC3137 | Aug. 30, 2011 |
| A6-2G5-41 | DSM ACC3138 | Aug. 30, 2011 |
| A4-2A1-18 | DSM ACC3139 | Aug. 30, 2011 |
| A4-2A1-40 | DSM ACC3140 | Aug. 30, 2011 |
| A6-1D2-12 | DSM ACC3141 | Sep. 6th, 2011 |

TABLE 11A

Peptide library used for epitope mapping
Peptide library for T3

| | Peptide no. | 393 | 394 | 395 | 396 | 397 | 398 | 399 | 400 | 401 | 402 | 403 | 404 | 405 | 406 | 407 | 408 |
|---|---|---|---|---|---|---|---|---|---|---|---|---|---|---|---|---|---|
| | | V | Y | K | S(p) | P | V | V | S | G | D | T | S(p) | P | R | H | L |
| Phospho peptides | T3.9 | V | Y | K | S(p) | P | V | V | S | | | | | | | | |
| | T3.10 | | Y | K | S(p) | P | V | V | S | G | | | | | | | |
| | T3.11 | | | K | S(p) | P | V | V | S | G | D | | | | | | |
| | T3.12 | | | | S(p) | P | V | V | S | G | D | T | | | | | |
| | T3.13 | | | | | P | V | V | S | G | D | T | S(p) | | | | |
| | T3.14 | | | | | | V | V | S | G | D | T | S(p) | P | | | |
| | T3.15 | | | | | | | V | S | G | D | T | S(p) | P | R | | |
| | T3.16 | | | | | | | | S | G | D | T | S(p) | P | R | H | |
| | T3.17 | | | | | | | | | G | D | T | S(p) | P | R | H | L |

| | Peptide no. | V | Y | K | S | P | V | V | S | G | D | T | S | P | R | H | L |
|---|---|---|---|---|---|---|---|---|---|---|---|---|---|---|---|---|---|
| Non-phospho peptides | T3.18 | V | Y | K | S | P | V | V | S | | | | | | | | |
| | T3.19 | | Y | K | S | P | V | V | S | G | | | | | | | |
| | T3.20 | | | K | S | P | V | V | S | G | D | | | | | | |
| | T3.21 | | | | S | P | V | V | S | G | D | T | | | | | |
| | T3.22 | | | | | P | V | V | S | G | D | T | S | | | | |
| | T3.23 | | | | | | V | V | S | G | D | T | S | P | | | |
| | T3.24 | | | | | | | V | S | G | D | T | S | P | R | | |
| | T3.25 | | | | | | | | S | G | D | T | S | P | R | H | |
| | T3.26 | | | | | | | | | G | D | T | S | P | R | H | L |

TABLE 11B

Alanine (Ala) substitution peptide library used for epitope mapping of pS396-specific antibodies

| Peptide No. | 393 | 394 | 395 | 396 | 397 | 398 | 399 | 400 |
|---|---|---|---|---|---|---|---|---|
| T3-Ala.A1 | V | Y | K | S | P | V | V | S |
| T3-Ala.A2 | V | Y | K | S(p) | P | V | V | S |
| T3-Ala.A3 | A | Y | K | S(p) | P | V | V | S |
| T3-Ala.A4 | V | A | K | S(p) | P | V | V | S |
| T3-Ala.A5 | V | Y | A | S(p) | P | V | V | S |
| T3-Ala.A6 | V | Y | K | A | P | V | V | S |
| T3-Ala.A7 | V | Y | K | S(p) | A | V | V | S |
| T3-Ala.A8 | V | Y | K | S(p) | P | A | V | S |
| T3-Ala.A9 | V | Y | K | S(p) | P | V | A | S |
| T3-Ala.A10 | V | Y | K | S(p) | P | V | V | A |

TABLE 11C

Alanine (Ala) substitution peptide library used for epitope mapping of pS404-specific antibodies

| Peptide No. | 400 | 401 | 402 | 403 | 404 | 405 | 406 | 407 |
|---|---|---|---|---|---|---|---|---|
| T3-Ala.B1 | S | G | D | T | S | P | R | H |
| T3-Ala.B2 | S | G | D | T | S(p) | P | R | H |
| T3-Ala.B3 | A | G | D | T | S(p) | P | R | H |
| T3-Ala.B4 | S | A | D | T | S(p) | P | R | H |
| T3-Ala.B5 | S | G | A | T | S(p) | P | R | H |
| T3-Ala.B6 | S | G | D | A | S(p) | P | R | H |
| T3-Ala.B7 | S | G | D | T | A | P | R | H |
| T3-Ala.B8 | S | G | D | T | S(p) | A | R | H |
| T3-Ala.B9 | S | G | D | T | S(p) | P | A | H |
| T3-Ala.B10 | S | G | D | T | S(p) | P | R | A |

REFERENCE LIST

Alonso A. D., et al. (1997), Proc. Natl. Acad. Sci. U.S.A., 94, 298-303

Alving et al., (1992) Infect. Immun. 60:2438-2444

Asuni et al., (2007) J. Neurosc. 27 (34), 9115-29

Braak and Braak (1991) Neuropathological staging of Alzheimer-related changes. Acta Neuropathol 82:239-259)

Braak H., et al. (1993), Eur. Neurol., 33, 403-408

Gill et al., Nature Med. 9: 589-595 (2003)

Greenberg S. G., et al. (1992), J. Biol. Chem., 267, 564-569.

Harlow and Lane, Antibodies: A Laboratory Manual (Cold Spring Harbor Laboratory, New York 1988 555-612

Hodgson et al., (1991) Bio/Technoloy, 9:421

Hoffmann R., et al (1997), Biochemistry, 36, 8114-8124.

Kabat E A, Wu T T, Perry H M, Gottesman K S, Foeller C.

*Sequences of proteins of Immunological Interest*, US Department of Health and Human Services, 1991
Kennedy, J. H., et al., 1976 (Clin. Chim. Acta 70:1-31)
Khaw, B. A. et al. (1982) J. Nucl. Med. 23:1011-1019
Lewis et al., (2000) Nature Genetics, 25:402-405
Masliah et al., (2005) Neuron, 46(6), 857-68
Masliah et al., (2011) PLoS ONE, Volume 6(4), e19338, pp-1-17
Muhs et al., (2007) Proc Natl Acad Sci USA, 104(23), 9810-5
Muyllaert et al, (2006) Rev Neurol, 162(10), 903-907
Muyllaert et al, (2008) Genes Brain Behav., Suppl. 1, 57-66
Neuwelt, E. A., Implication of the Blood-Brain Barrier and its Manipulation, Vols 1 & 2, Plenum Press, N.Y. (1989))
Nicolau et. al. (2002) Proc Natl. Acad. Sci USA 99, 2332-2337
Nicoll et al., (2003) Nature Med, 9, 448-452
Oddo et al., (2004) Neuron, 43, 321-332
Queen et al., (1989) Proc. Natl Acad Sci USA, 86:10029-10032
Papanastassiou et al., Gene Therapy 9: 398-406 (2002)
Reig S., et al. (1995), Acta Neuropathol., 90, 441-447
Ribe et al., (2005) Neurobiol Dis, 20(3), 814-22
Roberson et al, (2007) Science, 316 (5825), 750-4
Rosenmann et al., (2006) Arch Neurol, 63(10), 1459-67
Rousseaux et al. Methods Enzymology, (1986), Academic Press 121:663-69
Schurs, A. H. W. M., et al. 1977 {Clin. Chim Acta 57:1-40
Terwel et al., (2006) J Biol Chem, 280, 3963-3973
Terwel et al, (2008) Am J pathol., 172(3), 786-98
Urushitiani et al., (2007) Proc. Natl Acad Sci USA, 104(79, 2495-500
Vandebroek et al., *"Phosphotylation and Aggregation of Protein Tau in Humanized Yeast Cells and in Transgenic Mouse Brain"*; 7th International Conference on Alzheimer's and Parkinson's Disease, Sorrento, Italy, Mar. 9-13, 2005, pp 15-19
Wagner et al (2002) Journal of Liposome Research Vol 12(3), pp 259-270
WO 2004/058258
WO 96/13590
WO 96/29605
U.S. Patent Publication No. 2002/0038086
U.S. Patent Publication No. 2003/0083299
U.S. Patent Publication No. 2002/0025313
U.S. Patent Publication No 2004/0204354
U.S. Patent Publication No 2004/0131692
U.S. Patent Publication No 2002/0065259
U.S. Patent Publication No 2003/0162695
U.S. Patent Publication No 2005/0124533
U.S. Patent Publication No 2005/0089473
U.S. Patent Publication No 2003/0073713
U.S. Patent Publication No 2003/0129186
U.S. Pat. No. 5,112,596,
U.S. Pat. No. 5,268,164,
U.S. Pat. No. 5,506,206,
U.S. Pat. No. 5,686,416
U.S. Pat. No. 5,004,697

The invention claimed is:

1. An isolated antibody, or an antigen binding fragment thereof, which recognizes and specifically binds to a phospho-epitope on the mammalian Tau protein or on a fragment thereof, wherein the mammalian Tau protein or fragment thereof comprises a phospho-epitope having, or within, the amino acid sequence VYKSPVVS (Tau aa 393-400 of SEQ ID NO: 67) comprising a phosphorylated Ser at position 396 (pS396), wherein said antibody comprises a light chain variable region comprising a CDR1 comprising the amino acid sequence of SEQ ID NO: 106, a CDR2 comprising the amino acid sequence of SEQ ID NO: 107, and a CDR3 comprising the amino acid sequence of SEQ ID NO: 108; and a heavy chain variable region comprising a CDR1 comprising the amino acid sequence of SEQ ID NO: 89, a CDR2 comprising the amino acid sequence of SEQ ID NO: 115, and a CDR3 comprising the amino acid sequence of SEQ ID NO: 91.

2. The isolated antibody of claim 1 or an antigen binding fragment thereof, wherein said antibody or antigen binding fragment reduces soluble and/or insoluble Tau levels in the brain of a mammal.

3. The isolated antibody of claim 2 or an antigen binding fragment thereof, wherein said antibody or antigen binding fragment reduces soluble and/or insoluble Tau levels in brain cortex and/or hippocampus.

4. The isolated antibody or an antigen binding fragment thereof of claim 2, wherein the antibody or antigen binding fragment reduces phosphorylated tau protein levels.

5. The isolated antibody or an antigen binding fragment thereof of claim 1, wherein said antibody or antigen binding fragment reduces the levels of paired helical filaments containing hyperphosphorylated tau protein.

6. The isolated antibody or an antigen binding fragment thereof of claim 1, wherein said antibody or antigen binding fragment reduces the levels of total soluble tau protein, soluble phosphorylated tau protein and pTau paired helical filaments.

7. The isolated antibody or an antigen binding fragment thereof of claim 2, wherein said mammal is a human.

8. The isolated antibody or an antigen binding fragment thereof of claim 1, wherein said antibody or antigen binding fragment has a dissociation constant of less than 10 nM.

9. The isolated antibody or an antigen binding fragment thereof of claim 1, wherein said antibody or antigen binding fragment has an association rate constant of $10^4$ $M^{-1}$ $s^{-1}$ or greater.

10. The isolated antibody or an antigen binding fragment thereof of claim 1, wherein said antibody or antigen binding fragment has a high binding affinity with a dissociation constant of at least 4 nM and an association rate constant of $10^5 M^{-1}$ $s^{-1}$ or greater.

11. The isolated antibody or an antigen binding fragment thereof of claim 1, which is a monoclonal antibody, a chimeric antibody, or a humanized antibody.

12. The isolated antibody or an antigen binding fragment thereof of claim 11, which is of the IgG2b, IgG2a or the IgG3 isotype.

13. The isolated antibody or an antigen binding fragment thereof of claim 1, wherein said antibody or fragment thereof binds to a pathological protein Tau conformer, but does not bind to the corresponding unphosphorylated epitope and/or to non-related epitopes.

14. A pharmaceutical composition comprising the isolated antibody or an antigen binding fragment thereof of claim 1, or a combination thereof, in a therapeutically effective amount together with a pharmaceutically acceptable carrier.

15. A test kit for detection of phosphoTau (pTau) multimers comprising the isolated antibody or an antigen binding fragment thereof of claim 1.

16. An isolated antibody, or an antigen binding fragment thereof, which recognizes and specifically binds to a phospho-epitope on the mammalian Tau protein or on a fragment thereof-, wherein the mammalian Tau protein or fragment thereof comprises a phospho-epitope having, or within, the amino acid sequence VYKSPVVS (Tau aa 393-400 of SEQ ID NO: 67) comprising a phosphorylated Ser at position 396 (pS396), wherein said antibody comprises:

a light chain variable region which is at least 90% identical to SEQ ID NO: 105 and has a CDR1 comprising the amino acid sequence of SEQ ID NO: 106, a CDR2 comprising the amino acid sequence of SEQ ID NO: 107, and a CDR3 comprising the amino acid sequence of SEQ ID NO: 108; and a heavy chain variable region which is at least 90% identical to SEQ ID NO: 104 and has a CDR1 comprising the amino acid sequence of SEQ ID NO: 89, a CDR2 comprising the amino acid sequence of SEQ ID NO: 115, and a CDR3 comprising the amino acid sequence of SEQ ID NO: 91.

17. The isolated antibody or an antigen binding fragment thereof of claim 16, comprising a heavy chain variable region comprising the amino acid sequence shown in SEQ ID NO: 104 and/or a light chain variable region comprising the amino acid sequence shown in SEQ ID NO: 105.

* * * * *

UNITED STATES PATENT AND TRADEMARK OFFICE
CERTIFICATE OF CORRECTION

PATENT NO.       : 9,540,434 B2
APPLICATION NO.  : 14/348918
DATED            : January 10, 2017
INVENTOR(S)      : Andrea Pfeifer et al.

Page 1 of 1

It is certified that error appears in the above-identified patent and that said Letters Patent is hereby corrected as shown below:

In the Specification

In Column 7, Line 15, "SEQ ID NO: 89" should read --SEQ ID NO: 12--.

In Column 7, Line 37, "SEQ ID NO: 89" should read --SEQ ID NO: 12--.

In Column 12, Line 40, "SEQ ID NOs: 89-91" should read --SEQ ID NOs: 12, 90, and 91--.

In Column 15, Line 47, "SEQ ID NOs: 70-72, 78-80, 89-91," should read --SEQ ID NOs: 70-72, 78-80, (12, 90, 91),--.

In Column 25, Lines 63 through 67, "SEQ ID NO: 89 depicts the amino acid sequence of the CDR1 of the heavy chain variable region (VH) of monoclonal antibody ACI-35-2A1-Ab1, ACI-35-2A1-Ab2, ACI-35-4A6-Ab2, ACI-35-2G5-AB2 and ACI-35-2G5-AB3, respectively." should read --SEQ ID NO: 89 depicts the amino acid sequence of the CDR1 of the heavy chain variable region (VH) of monoclonal antibody ACI-35-2G5-AB2 and ACI-35-2G5-AB3, respectively.--

In Table 6, Rows 3, 4, and 5, at Columns 61 to 62, the VH CDR1 for ACI-35-2A1 -Ab1 (Row 3), ACI-35-2A1-Ab2 (Row 4), and ACI-35-4A6-Ab2 (Row 5), "GYTFTDYYMN (SEQ ID NO: 89)" should read --GYTFTDYYMN (SEQ ID NO: 12)--.

Signed and Sealed this
Seventh Day of November, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 221

<210> SEQ ID NO 1
<211> LENGTH: 115
<212> TYPE: PRT
<213> ORGANISM: Mus musculus
<220> FEATURE:
<221> NAME/KEY: SOURCE
<222> LOCATION: 1..115
<223> OTHER INFORMATION: /mol_type="protein"
      /organism="Mus musculus"

<400> SEQUENCE: 1

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Arg Gly Thr Thr Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Ser Tyr Tyr Ala Val Gly Tyr Trp Gly Gln Gly Thr Thr Leu Thr
            100                 105                 110

Val Ser Ser
        115

<210> SEQ ID NO 2
<211> LENGTH: 115
```

```
<212> TYPE: PRT
<213> ORGANISM: Mus musculus
<220> FEATURE:
<221> NAME/KEY: SOURCE
<222> LOCATION: 1..115
<223> OTHER INFORMATION: /mol_type="protein"
      /organism="Mus musculus"

<400> SEQUENCE: 2
```

Glu Val Gln Leu Gln Gln Ser Gly Pro Glu Leu Val Lys Pro Gly Thr
1               5                   10                  15

Ser Val Lys Ile Ser Cys Lys Ala Ser Gly Tyr Thr Phe Thr Asp Tyr
                20                  25                  30

Tyr Met Asn Trp Val Lys Gln Ser His Gly Lys Ser Leu Glu Trp Ile
            35                  40                  45

Gly Asp Ile Asn Pro Asn Arg Gly Gly Thr Thr Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Ser Tyr Tyr Ala Val Gly Tyr Trp Gly Gln Gly Thr Thr Leu Thr
            100                 105                 110

Val Ser Ser
    115

```
<210> SEQ ID NO 3
<211> LENGTH: 115
<212> TYPE: PRT
<213> ORGANISM: Mus musculus
<220> FEATURE:
<221> NAME/KEY: SOURCE
<222> LOCATION: 1..115
<223> OTHER INFORMATION: /mol_type="protein"
      /organism="Mus musculus"

<400> SEQUENCE: 3
```

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Tyr Met Asn Trp Val Lys Gln Ser His Gly Lys Ser Leu Glu Trp Ile
            35                  40                  45

Gly Asp Ile Asn Pro Asn Arg Gly Gly Thr Thr Tyr Asn Gln Lys Phe
    50                  55                  60

Lys Gly Lys Ala Thr Leu Thr Val Asp Thr Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Ser Tyr Tyr Ala Val Gly Tyr Trp Gly Gln Gly Thr Thr Leu Thr
            100                 105                 110

Val Ser Ser
    115

```
<210> SEQ ID NO 4
<211> LENGTH: 120
<212> TYPE: PRT
<213> ORGANISM: Mus musculus
<220> FEATURE:
<221> NAME/KEY: SOURCE
<222> LOCATION: 1..120
```

<223> OTHER INFORMATION: /mol_type="protein"
       /organism="Mus musculus"

<400> SEQUENCE: 4

Glu Val Gln Leu Val Glu Ser Gly Gly Gly Leu Val Lys Pro Gly Gly
1               5                   10                  15

Ser Leu Lys Leu Ser Cys Ala Pro Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Gly Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Gly Gln Leu Arg Leu Arg Leu Phe Ala Tyr Trp Gly Gln
            100                 105                 110

Gly Thr Leu Val Thr Val Ser Ala
        115                 120

<210> SEQ ID NO 5
<211> LENGTH: 119
<212> TYPE: PRT
<213> ORGANISM: Mus musculus
<220> FEATURE:
<221> NAME/KEY: SOURCE
<222> LOCATION: 1..119
<223> OTHER INFORMATION: /mol_type="protein"
       /organism="Mus musculus"

<400> SEQUENCE: 5

Glu Val Lys Leu Met Glu Ser Gly Gly Gly Leu Val His Pro Gly Ala
1               5                   10                  15

Ser Leu Arg Leu Tyr Cys Ala Ala Ser Gly Phe Thr Phe Thr Asp Tyr
            20                  25                  30

Tyr Met Ser Trp Val Arg Gln Pro Pro Gly Lys Ala Pro Glu Trp Leu
        35                  40                  45

Ala Leu Ile Arg Asn Lys Ala Asn Gly Tyr Thr Thr Glu Tyr Thr Ala
    50                  55                  60

Ser Val Lys Gly Arg Phe Thr Ile Ser Arg Asp Asn Ser Gln Asn Ile
65                  70                  75                  80

Leu Tyr Leu Gln Met Asn Thr Leu Arg Ala Glu Asp Ser Ala Thr Tyr
                85                  90                  95

Tyr Cys Val Lys Ala Leu Gly Arg Tyr Phe Asp Val Trp Gly Thr Gly
            100                 105                 110

Thr Thr Val Thr Val Ser Ser
        115

<210> SEQ ID NO 6
<211> LENGTH: 113
<212> TYPE: PRT
<213> ORGANISM: Mus musculus
<220> FEATURE:
<221> NAME/KEY: SOURCE
<222> LOCATION: 1..113
<223> OTHER INFORMATION: /mol_type="protein"
       /organism="Mus musculus"

<400> SEQUENCE: 6

-continued

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Val Phe Asn Ser
            20                  25                  30

Gly Asn Gln Lys Asn Ser Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Ser Leu Thr
65                  70                  75                  80

Ile Ser Ser Val Gln Ala Glu Asp Leu Ala Asp Tyr Phe Cys Gln Glu
                85                  90                  95

His Tyr Thr Thr Pro Pro Thr Phe Gly Thr Gly Thr Lys Leu Glu Leu
                100                 105                 110

Lys

<210> SEQ ID NO 7
<211> LENGTH: 112
<212> TYPE: PRT
<213> ORGANISM: Mus musculus
<220> FEATURE:
<221> NAME/KEY: SOURCE
<222> LOCATION: 1..112
<223> OTHER INFORMATION: /mol_type="protein"
      /organism="Mus musculus"

<400> SEQUENCE: 7

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Arg Leu Val His Ser
            20                  25                  30

His Gly Lys Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Ala His Phe Pro Tyr Thr Phe Gly Gly Gly Thr Lys Leu Glu Ile Lys
                100                 105                 110

<210> SEQ ID NO 8
<211> LENGTH: 112
<212> TYPE: PRT
<213> ORGANISM: Mus musculus
<220> FEATURE:
<221> NAME/KEY: SOURCE
<222> LOCATION: 1..112
<223> OTHER INFORMATION: /mol_type="protein"
      /organism="Mus musculus"

<400> SEQUENCE: 8

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

His Gly Lys Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Ala His Phe Pro Tyr Thr Phe Gly Gly Gly Thr Lys Leu Glu Ile Lys
                100                 105                 110

<210> SEQ ID NO 9
<211> LENGTH: 112
<212> TYPE: PRT
<213> ORGANISM: Mus musculus
<220> FEATURE:
<221> NAME/KEY: SOURCE
<222> LOCATION: 1..112
<223> OTHER INFORMATION: /mol_type="protein"
      /organism="Mus musculus"

<400> SEQUENCE: 9

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu His Ser
                20                  25                  30

His Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Ala His Phe Pro Tyr Thr Phe Gly Gly Gly Thr Lys Leu Glu Ile Lys
                100                 105                 110

<210> SEQ ID NO 10
<211> LENGTH: 107
<212> TYPE: PRT
<213> ORGANISM: Mus musculus
<220> FEATURE:
<221> NAME/KEY: SOURCE
<222> LOCATION: 1..107
<223> OTHER INFORMATION: /mol_type="protein"
      /organism="Mus musculus"

<400> SEQUENCE: 10

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
                20                  25                  30

Val Ala Trp Tyr Gln Gln Lys Pro Gly Gln Ser Pro Lys Leu Leu Ile
            35                  40                  45

Tyr Ser Ala Ser Tyr Arg Tyr Thr Gly Val Pro Asp Arg Phe Thr Gly
        50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Leu
                85                  90                  95

Thr Phe Gly Ala Gly Thr Lys Leu Glu Leu Lys
                100                 105

<210> SEQ ID NO 11
<211> LENGTH: 113
<212> TYPE: PRT
<213> ORGANISM: Mus musculus
<220> FEATURE:
<221> NAME/KEY: SOURCE
<222> LOCATION: 1..113
<223> OTHER INFORMATION: /mol_type="protein"
      /organism="Mus musculus"

<400> SEQUENCE: 11

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Phe Thr Phe Gly Ser Gly Thr Lys Leu Glu Ile
                100                 105                 110

Lys

<210> SEQ ID NO 12
<211> LENGTH: 10
<212> TYPE: PRT
<213> ORGANISM: Mus musculus
<220> FEATURE:
<221> NAME/KEY: SOURCE
<222> LOCATION: 1..10
<223> OTHER INFORMATION: /mol_type="protein"
      /organism="Mus musculus"

<400> SEQUENCE: 12

Gly Tyr Thr Phe Thr Asp Tyr Tyr Met Asn
1               5                   10

<210> SEQ ID NO 13
<211> LENGTH: 17
<212> TYPE: PRT
<213> ORGANISM: Mus musculus
<220> FEATURE:
<221> NAME/KEY: SOURCE
<222> LOCATION: 1..17
<223> OTHER INFORMATION: /mol_type="protein"
      /organism="Mus musculus"

<400> SEQUENCE: 13

Asp Ile Asn Pro Asn Arg Gly Gly Thr Thr Tyr Asn Gln Lys Phe Lys
1               5                   10                  15

Gly

<210> SEQ ID NO 14
<211> LENGTH: 6
<212> TYPE: PRT
<213> ORGANISM: Mus musculus
<220> FEATURE:
<221> NAME/KEY: SOURCE
<222> LOCATION: 1..6

<223> OTHER INFORMATION: /mol_type="protein"
     /organism="Mus musculus"

<400> SEQUENCE: 14

Tyr Tyr Ala Val Gly Tyr
1               5

<210> SEQ ID NO 15
<211> LENGTH: 10
<212> TYPE: PRT
<213> ORGANISM: Mus musculus
<220> FEATURE:
<221> NAME/KEY: SOURCE
<222> LOCATION: 1..10
<223> OTHER INFORMATION: /mol_type="protein"
     /organism="Mus musculus"

<400> SEQUENCE: 15

Gly Phe Thr Phe Ser Asp Tyr Gly Met His
1               5                   10

<210> SEQ ID NO 16
<211> LENGTH: 17
<212> TYPE: PRT
<213> ORGANISM: Mus musculus
<220> FEATURE:
<221> NAME/KEY: SOURCE
<222> LOCATION: 1..17
<223> OTHER INFORMATION: /mol_type="protein"
     /organism="Mus musculus"

<400> SEQUENCE: 16

Tyr Ile Ser Ser Gly Ser Ser Thr Ile Tyr Tyr Gly Asp Thr Val Lys
1               5                   10                  15

Gly

<210> SEQ ID NO 17
<211> LENGTH: 11
<212> TYPE: PRT
<213> ORGANISM: Mus musculus
<220> FEATURE:
<221> NAME/KEY: SOURCE
<222> LOCATION: 1..11
<223> OTHER INFORMATION: /mol_type="protein"
     /organism="Mus musculus"

<400> SEQUENCE: 17

Arg Gly Gln Leu Arg Leu Arg Leu Phe Ala Tyr
1               5                   10

<210> SEQ ID NO 18
<211> LENGTH: 10
<212> TYPE: PRT
<213> ORGANISM: Mus musculus
<220> FEATURE:
<221> NAME/KEY: SOURCE
<222> LOCATION: 1..10
<223> OTHER INFORMATION: /mol_type="protein"
     /organism="Mus musculus"

<400> SEQUENCE: 18

Gly Phe Thr Phe Thr Asp Tyr Tyr Met Ser
1               5                   10

<210> SEQ ID NO 19
<211> LENGTH: 19
<212> TYPE: PRT
<213> ORGANISM: Mus musculus

```
<220> FEATURE:
<221> NAME/KEY: SOURCE
<222> LOCATION: 1..19
<223> OTHER INFORMATION: /mol_type="protein"
      /organism="Mus musculus"

<400> SEQUENCE: 19

Leu Ile Arg Asn Lys Ala Asn Gly Tyr Thr Thr Glu Tyr Thr Ala Ser
1               5                   10                  15
Val Lys Gly

<210> SEQ ID NO 20
<211> LENGTH: 8
<212> TYPE: PRT
<213> ORGANISM: Mus musculus
<220> FEATURE:
<221> NAME/KEY: SOURCE
<222> LOCATION: 1..8
<223> OTHER INFORMATION: /mol_type="protein"
      /organism="Mus musculus"

<400> SEQUENCE: 20

Ala Leu Gly Arg Tyr Phe Asp Val
1               5

<210> SEQ ID NO 21
<211> LENGTH: 17
<212> TYPE: PRT
<213> ORGANISM: Mus musculus
<220> FEATURE:
<221> NAME/KEY: SOURCE
<222> LOCATION: 1..17
<223> OTHER INFORMATION: /mol_type="protein"
      /organism="Mus musculus"

<400> SEQUENCE: 21

Lys Ser Ser Gln Ser Val Phe Asn Ser Gly Asn Gln Lys Asn Ser Leu
1               5                   10                  15
Ala

<210> SEQ ID NO 22
<211> LENGTH: 7
<212> TYPE: PRT
<213> ORGANISM: Mus musculus
<220> FEATURE:
<221> NAME/KEY: SOURCE
<222> LOCATION: 1..7
<223> OTHER INFORMATION: /mol_type="protein"
      /organism="Mus musculus"

<400> SEQUENCE: 22

Phe Ala Ser Thr Arg Glu Ser
1               5

<210> SEQ ID NO 23
<211> LENGTH: 9
<212> TYPE: PRT
<213> ORGANISM: Mus musculus
<220> FEATURE:
<221> NAME/KEY: SOURCE
<222> LOCATION: 1..9
<223> OTHER INFORMATION: /mol_type="protein"
      /organism="Mus musculus"

<400> SEQUENCE: 23

Gln Glu His Tyr Thr Thr Pro Pro Thr
1               5
```

```
<210> SEQ ID NO 24
<211> LENGTH: 16
<212> TYPE: PRT
<213> ORGANISM: Mus musculus
<220> FEATURE:
<221> NAME/KEY: SOURCE
<222> LOCATION: 1..16
<223> OTHER INFORMATION: /mol_type="protein"
      /organism="Mus musculus"

<400> SEQUENCE: 24

Arg Ser Ser Gln Arg Leu Val His Ser His Gly Lys Thr Tyr Leu His
1               5                   10                  15

<210> SEQ ID NO 25
<211> LENGTH: 7
<212> TYPE: PRT
<213> ORGANISM: Mus musculus
<220> FEATURE:
<221> NAME/KEY: SOURCE
<222> LOCATION: 1..7
<223> OTHER INFORMATION: /mol_type="protein"
      /organism="Mus musculus"

<400> SEQUENCE: 25

Lys Val Ser Asn Arg Phe Ser
1               5

<210> SEQ ID NO 26
<211> LENGTH: 9
<212> TYPE: PRT
<213> ORGANISM: Mus musculus
<220> FEATURE:
<221> NAME/KEY: SOURCE
<222> LOCATION: 1..9
<223> OTHER INFORMATION: /mol_type="protein"
      /organism="Mus musculus"

<400> SEQUENCE: 26

Ser Gln Thr Ala His Phe Pro Tyr Thr
1               5

<210> SEQ ID NO 27
<211> LENGTH: 16
<212> TYPE: PRT
<213> ORGANISM: Mus musculus
<220> FEATURE:
<221> NAME/KEY: SOURCE
<222> LOCATION: 1..16
<223> OTHER INFORMATION: /mol_type="protein"
      /organism="Mus musculus"

<400> SEQUENCE: 27

Arg Ser Ser Gln Ser Leu Val His Ser His Gly Lys Thr Tyr Leu His
1               5                   10                  15

<210> SEQ ID NO 28
<211> LENGTH: 16
<212> TYPE: PRT
<213> ORGANISM: Mus musculus
<220> FEATURE:
<221> NAME/KEY: SOURCE
<222> LOCATION: 1..16
<223> OTHER INFORMATION: /mol_type="protein"
      /organism="Mus musculus"

<400> SEQUENCE: 28

Arg Ser Ser Gln Ser Leu Leu His Ser His Gly Asn Thr Tyr Leu His
1               5                   10                  15
```

<210> SEQ ID NO 29
<211> LENGTH: 11
<212> TYPE: PRT
<213> ORGANISM: Mus musculus
<220> FEATURE:
<221> NAME/KEY: SOURCE
<222> LOCATION: 1..11
<223> OTHER INFORMATION: /mol_type="protein"
      /organism="Mus musculus"

<400> SEQUENCE: 29

Lys Ala Ser Gln Asp Val Ser Thr Ala Val Ala
1               5                   10

<210> SEQ ID NO 30
<211> LENGTH: 7
<212> TYPE: PRT
<213> ORGANISM: Mus musculus
<220> FEATURE:
<221> NAME/KEY: SOURCE
<222> LOCATION: 1..7
<223> OTHER INFORMATION: /mol_type="protein"
      /organism="Mus musculus"

<400> SEQUENCE: 30

Ser Ala Ser Tyr Arg Tyr Thr
1               5

<210> SEQ ID NO 31
<211> LENGTH: 9
<212> TYPE: PRT
<213> ORGANISM: Mus musculus
<220> FEATURE:
<221> NAME/KEY: SOURCE
<222> LOCATION: 1..9
<223> OTHER INFORMATION: /mol_type="protein"
      /organism="Mus musculus"

<400> SEQUENCE: 31

Gln Gln His Tyr Thr Thr Pro Leu Thr
1               5

<210> SEQ ID NO 32
<211> LENGTH: 17
<212> TYPE: PRT
<213> ORGANISM: Mus musculus
<220> FEATURE:
<221> NAME/KEY: SOURCE
<222> LOCATION: 1..17
<223> OTHER INFORMATION: /mol_type="protein"
      /organism="Mus musculus"

<400> SEQUENCE: 32

Lys Ser Ser Gln Ser Leu Leu Tyr Ser Ser Asn Gln Lys Asn Tyr Leu
1               5                   10                  15

Ala

<210> SEQ ID NO 33
<211> LENGTH: 7
<212> TYPE: PRT
<213> ORGANISM: Mus musculus
<220> FEATURE:
<221> NAME/KEY: SOURCE
<222> LOCATION: 1..7
<223> OTHER INFORMATION: /mol_type="protein"
      /organism="Mus musculus"

<400> SEQUENCE: 33

Trp Ala Ser Thr Arg Glu Ser
1               5

<210> SEQ ID NO 34
<211> LENGTH: 9
<212> TYPE: PRT
<213> ORGANISM: Mus musculus
<220> FEATURE:
<221> NAME/KEY: SOURCE
<222> LOCATION: 1..9
<223> OTHER INFORMATION: /mol_type="protein"
      /organism="Mus musculus"

<400> SEQUENCE: 34

Gln Gln Tyr Tyr Ser Tyr Pro Phe Thr
1               5

<210> SEQ ID NO 35
<211> LENGTH: 345
<212> TYPE: DNA
<213> ORGANISM: Mus musculus
<220> FEATURE:
<221> NAME/KEY: source
<222> LOCATION: 1..345
<223> OTHER INFORMATION: /mol_type="DNA"
      /organism="Mus musculus"

<400> SEQUENCE: 35
gaggtccagc tgcaacaatc tggacctgaa ctggtgaagc ctggggcttc agtgaagata    60
tcctgtaagg cttctggata tacgttcact gactactaca tgaactgggt gaagcagagc   120
catggaaaga gccttgagtg gattggagat attaatccta accgtggtgg aactacttac   180
aaccagaagt tcaagggcaa ggccacgttg actgtagaca gtcctccag cacagcctac    240 atggaactcc gcagcctgac atctgaggac tctgcagtct attactgtgc aagttactac   300
gccgtgggct actggggcca aggcaccact ctcacagtct cctca                   345

<210> SEQ ID NO 36
<211> LENGTH: 345
<212> TYPE: DNA
<213> ORGANISM: Mus musculus
<220> FEATURE:
<221> NAME/KEY: source
<222> LOCATION: 1..345
<223> OTHER INFORMATION: /mol_type="DNA"
      /organism="Mus musculus"

<400> SEQUENCE: 36
gaggtccagc tgcaacaatc tggacctgaa ctggtgaagc ctgggacttc agtgaagata    60
tcctgtaagg cttctggata tacgttcact gactactaca tgaactgggt gaagcagagc   120
catggaaaga gccttgagtg gattggagat attaatccta accgtggtgg aactacttac   180
aaccagaagt ttaagggcaa ggccacgttg actgtagaca gtcctccag cacagcctac    240 atggaactcc gcagcctgac atctgaggac tctgcagtct attactgtgc aagttactac   300
gccgtgggct actggggcca aggcaccact ctcacagtct cctca                   345

<210> SEQ ID NO 37
<211> LENGTH: 345
<212> TYPE: DNA
<213> ORGANISM: Mus musculus
<220> FEATURE:
<221> NAME/KEY: source
<222> LOCATION: 1..345
<223> OTHER INFORMATION: /mol_type="DNA"

-continued

/organism="Mus musculus"

<400> SEQUENCE: 37

| gaggtccagc | tgcaacaatc | tggacctgaa | ctggtgaagc | ctggggcttc | agtgaagata | 60 |
| tcctgtaagg | cttctggata | cacgttcact | gactactaca | tgaactgggt | gaagcagagc | 120 |
| catggaaaga | gccttgagtg | gattggagat | attaatccta | accgtggtgg | aactacttac | 180 |
| aaccagaagt | tcaagggcaa | ggccacgttg | actgtagaca | cgtcctccag | cacagcctac | 240 |
| atggagctcc | gcagcctgac | atctgaggac | tctgcagtct | attactgtgc | aagttactac | 300 |
| gccgtgggct | actggggcca | aggcaccact | ctcacagtct | cctca | | 345 |

<210> SEQ ID NO 38
<211> LENGTH: 360
<212> TYPE: DNA
<213> ORGANISM: Mus musculus
<220> FEATURE:
<221> NAME/KEY: source
<222> LOCATION: 1..360
<223> OTHER INFORMATION: /mol_type="DNA"
      /organism="Mus musculus"

<400> SEQUENCE: 38

| gaggtgcagc | tggtggagtc | tgggggaggc | ttagtgaagc | ctggagggtc | cctgaaactc | 60 |
| tcctgtgcac | cctctggatt | cactttcagt | gactatggaa | tgcactgggt | tcgtcaggct | 120 |
| ccagagaagg | gactggagtg | ggttgcatac | attagtagtg | gcagtagtac | catctactat | 180 |
| ggagacacag | tgaagggccg | attcaccatc | tccagagaca | atgccaagaa | caccctgttc | 240 |
| ctgcaaatga | ccagtctgag | gtctgaggac | acggccatgt | attactgtgc | aagaagggga | 300 |
| cagctcaggc | tacgcctgtt | tgcttactgg | ggccaaggga | ctctggtcac | tgtctctgca | 360 |

<210> SEQ ID NO 39
<211> LENGTH: 357
<212> TYPE: DNA
<213> ORGANISM: Mus musculus
<220> FEATURE:
<221> NAME/KEY: source
<222> LOCATION: 1..357
<223> OTHER INFORMATION: /mol_type="DNA"
      /organism="Mus musculus"

<400> SEQUENCE: 39

| gaggtgaagc | tgatggaatc | tggaggaggc | ttggtacacc | ctggggcttc | tctgagactc | 60 |
| tactgtgcag | cttctggatt | caccttact | gattactaca | tgagctgggt | ccgccagcct | 120 |
| ccagggaagg | cacctgagtg | gttggctttg | attagaaaca | aagctaatgg | ttacacaaca | 180 |
| gagtatactg | catctgttaa | gggtcggttc | accatctcca | gagataattc | caaaacatc | 240 |
| ctctatcttc | aaatgaacac | cctgagggct | gaggacagtg | ccacttatta | ctgtgtaaaa | 300 |
| gctctgggac | gttacttcga | tgtctggggc | acagggacca | cggtcaccgt | ctcctca | 357 |

<210> SEQ ID NO 40
<211> LENGTH: 339
<212> TYPE: DNA
<213> ORGANISM: Mus musculus
<220> FEATURE:
<221> NAME/KEY: source
<222> LOCATION: 1..339
<223> OTHER INFORMATION: /mol_type="DNA"
      /organism="Mus musculus"

<400> SEQUENCE: 40

```
gacattgtga tgacacagtc tccatcctcc ctggctatgt cagtaggaca gaaggtcact    60
atgagctgca agtccagtca gagtgttttt aatagtggca atcaaaagaa ctctttggcc   120
tggtaccagc agaaaccagg acagtctcct aaacttctgg tatactttgc atccactagg   180
gaatctgggg tccctgatcg cttcataggc agtggatctg ggacagattt cagtcttacc   240
atcagcagtg tgcaggctga ggacctggca gattacttct gtcaggaaca ttataccact   300
cctcccacgt tcggtactgg gaccaagctg gagctgaaa                          339
```

<210> SEQ ID NO 41
<211> LENGTH: 336
<212> TYPE: DNA
<213> ORGANISM: Mus musculus
<220> FEATURE:
<221> NAME/KEY: source
<222> LOCATION: 1..336
<223> OTHER INFORMATION: /mol_type="DNA"
      /organism="Mus musculus"

<400> SEQUENCE: 41

```
gatgttgtga tgacccaaac tccactctcc ctgcctgtca gtcttggaga tcaagcctcc    60
atctcttgca gatctagtca gaggcttgta cacagtcatg gaaaaaccta tttacattgg   120
tacctgcaga agccaggcca gtctccaaag ctcctgatct acaaagtttc caaccggttt   180
tctggggtcc cagacaggtt cagtggcagt ggatcaggga cagatttcac actcaagatc   240
agcagagtgg aggctgagga tctgggagtt tatttctgtt ctcaaactgc acattttccg   300
tacacgttcg gaggggggac caagctggaa ataaaa                             336
```

<210> SEQ ID NO 42
<211> LENGTH: 336
<212> TYPE: DNA
<213> ORGANISM: Mus musculus
<220> FEATURE:
<221> NAME/KEY: source
<222> LOCATION: 1..336
<223> OTHER INFORMATION: /mol_type="DNA"
      /organism="Mus musculus"

<400> SEQUENCE: 42

```
gatgttgtga tgacccaaac tccactctcc ctgcctgtca gtcttggaga tcaagcctcc    60
atctcttgca gatctagtca gagccttgta cacagtcatg gaaaaaccta tttacattgg   120
tacctgcaga agccaggcca gtctccaaag ctcctgatct acaaagtttc caaccggttt   180
tctggggtcc cagacaggtt cagtggcagt ggatcaggga cagatttcac actcaagatc   240
agcagagtgg aggctgagga tctgggagtt tatttctgtt ctcaaactgc acattttccg   300
tacacgttcg gaggggggac caagctggaa ataaaa                             336
```

<210> SEQ ID NO 43
<211> LENGTH: 336
<212> TYPE: DNA
<213> ORGANISM: Mus musculus
<220> FEATURE:
<221> NAME/KEY: source
<222> LOCATION: 1..336
<223> OTHER INFORMATION: /mol_type="DNA"
      /organism="Mus musculus"

<400> SEQUENCE: 43

```
gatgttgtga tgacccaaac tccactctcc ctgcctgtca gtcttggaga tcaagcctcc    60
atctcttgca gatctagtca gagccttcta cacagtcatg gaaacaccta tttacattgg   120
```

```
tacctgcaga agccaggcca gtctccaaag ctcctgatct acaaagtttc caaccggttt      180
tctggggtcc cagacaggtt cagtggcagt ggatcaggga cagatttcac actcaagatc      240
agcagagtgg aggctgagga tctgggagtt tatttctgct ctcaaactgc acattttccg      300
tacacgttcg gaggggggac caagctggaa ataaaa                                336
```

```
<210> SEQ ID NO 44
<211> LENGTH: 321
<212> TYPE: DNA
<213> ORGANISM: Mus musculus
<220> FEATURE:
<221> NAME/KEY: source
<222> LOCATION: 1..321
<223> OTHER INFORMATION: /mol_type="DNA"
      /organism="Mus musculus"

<400> SEQUENCE: 44
```

```
gacattgtga tgacccagtc tcacaaattc atgtccacat cagtaggaga cagggtcagc      60
atcacctgca aggccagtca ggatgtgagt actgctgtag cctggtatca acagaaacca     120
ggacaatctc ctaaactact gatttactcg gcatcctacc ggtacactgg agtccctgat     180
cgcttcactg gcagtggatc tgggacggat ttcactttca ccatcagcag tgtgcaggct     240
gaagacctgg cagtttatta ctgtcagcaa cattatacta ctccgctcac gttcggtgct     300
gggaccaagc tggagctgaa a                                               321
```

```
<210> SEQ ID NO 45
<211> LENGTH: 339
<212> TYPE: DNA
<213> ORGANISM: Mus musculus
<220> FEATURE:
<221> NAME/KEY: source
<222> LOCATION: 1..339
<223> OTHER INFORMATION: /mol_type="DNA"
      /organism="Mus musculus"

<400> SEQUENCE: 45
```

```
gacattgtga tgtcacagtc tccatcctcc ctagctgtgt cagttggaga aaggttact      60 atgagctgca agtccagtca gagcctttta tatagtagca atcaaaagaa ctacttggcc     120
tggtaccagc agaaaccagg gcagtctcct aaactgctga tttactgggc atccactagg     180
gaatctgggg tccctgatcg cttcacaggc agtggatctg gacagattt cactctcacc      240 atcagcagtg tgaaggctga agacctggca gtttattact gtcagcaata ttatagctat     300
ccattcacgt tcggctcggg gacaaagttg gaaataaaa                            339
```

```
<210> SEQ ID NO 46
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 46
```

```
gggaattcat graatgsasc tgggtywtyc tctt                                  34
```

```
<210> SEQ ID NO 47
<211> LENGTH: 35
<212> TYPE: DNA
<213> ORGANISM: Artificial Sequence
```

```
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"
<220> FEATURE:
<221> NAME/KEY: variation
<222> LOCATION: 30..30
<223> OTHER INFORMATION: /replace="n=i"

<400> SEQUENCE: 47
cccaagcttc cagggrccar kggataracn grtgg                                 35

<210> SEQ ID NO 48
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="DNA"
      /note="Description of artificial sequence: primer"
      /organism="Artificial Sequence"

<400> SEQUENCE: 48
gggaattcat gragwcacak wcycaggtct tt                                    32

<210> SEQ ID NO 49
<211> LENGTH: 41
<212> TYPE: DNA
<213> ORGANISM: Artificial Sequence
<220> FEATURE:
<221> NAME/KEY: source
<222> LOCATION: 1..41
<223> OTHER INFORMATION: /mol_type="DNA"
      /note="Description of artificial sequence: primer"
      /organism="Artificial Sequence"

<400> SEQUENCE: 49
actagtcgac atgggcwtca agatgragtc acakwyycwg g                          41

<210> SEQ ID NO 50
<211> LENGTH: 39
<212> TYPE: DNA
<213> ORGANISM: Artificial Sequence
<220> FEATURE:
<221> NAME/KEY: source
<222> LOCATION: 1..39
<223> OTHER INFORMATION: /mol_type="DNA"
      /note="Description of artificial sequence: primer"
      /organism="Artificial Sequence"

<400> SEQUENCE: 50
actagtcgac atgaagttgc ctgttaggct gttggtgct                             39

<210> SEQ ID NO 51
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="DNA"
      /note="Description of artificial sequence: primer"
      /organism="Artificial Sequence"

<400> SEQUENCE: 51
cccaagctta ctggatggtg ggaagatgga                                       30
```

<210> SEQ ID NO 52
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="DNA"
      /note="Description of artificial sequence: primer"
      /organism="Artificial Sequence"

<400> SEQUENCE: 52
actagtcgac atgggatgga gctrtatcat sytctt                            36

<210> SEQ ID NO 53
<211> LENGTH: 33
<212> TYPE: DNA
<213> ORGANISM: artificial seuqence
<220> FEATURE:
<221> NAME/KEY: source
<222> LOCATION: 1..33
<223> OTHER INFORMATION: /mol_type="DNA"
      /note="Description of artificial sequence: primer"
      /organism="artificial seuqence"

<400> SEQUENCE: 53
gggaattcat grasttskgg ytmarctkgr ttt                               33

<210> SEQ ID NO 54
<211> LENGTH: 39
<212> TYPE: DNA
<213> ORGANISM: Artificial Sequence
<220> FEATURE:
<221> NAME/KEY: source
<222> LOCATION: 1..39
<223> OTHER INFORMATION: /mol_type="DNA"
      /note="Description of artificial sequence: primer"
      /organism="Artificial Sequence"

<400> SEQUENCE: 54
actagtcgac atggactcca ggctcaattt agttttcct                         39

<210> SEQ ID NO 55
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="DNA"
      /note="Description of artificial sequence: primer"
      /organism="Artificial Sequence"

<400> SEQUENCE: 55
actagtcgac atgaagwtgt ggbtraactg grt                               33

<210> SEQ ID NO 56
<211> LENGTH: 39
<212> TYPE: DNA
<213> ORGANISM: Artificial Sequence
<220> FEATURE:
<221> NAME/KEY: source
<222> LOCATION: 1..39
<223> OTHER INFORMATION: /mol_type="DNA"
      /note="Description of artificial sequence: primer"
      /organism="Artificial Sequence"
<220> FEATURE:
<221> NAME/KEY: misc_feature
<222> LOCATION: 27..27
<223> OTHER INFORMATION: /note="n=i"

<400> SEQUENCE: 56
actagtcgac atggagwcag acacacnsct gytatgggt                    39

<210> SEQ ID NO 57
<211> LENGTH: 37
<212> TYPE: DNA
<213> ORGANISM: Artificial Sequence
<220> FEATURE:
<221> NAME/KEY: source
<222> LOCATION: 1..37
<223> OTHER INFORMATION: /mol_type="DNA"
      /note="Description of artificial sequence: primer"
      /organism="Artificial Sequence"

<400> SEQUENCE: 57
actagtcgac atggtyctya tvttrctgct gctatgg                      37

<210> SEQ ID NO 58
<211> LENGTH: 30
<212> TYPE: PRT
<213> ORGANISM: artificial sequences
<220> FEATURE:
<221> NAME/KEY: SOURCE
<222> LOCATION: 1..30
<223> OTHER INFORMATION: /mol_type="protein"
      /note="Description of artifiial sequence: ACI-37"
      /organism="artificial sequences"
<220> FEATURE:
<221> NAME/KEY: VARIANT
<222> LOCATION: 18..18
<223> OTHER INFORMATION: phosphorylated serine
<220> FEATURE:
<221> NAME/KEY: VARIANT
<222> LOCATION: 26..26
<223> OTHER INFORMATION: phosphorylated serine

<400> SEQUENCE: 58

Arg Glu Asn Ala Lys Ala Lys Thr Asp His Gly Ala Glu Ile Val Tyr
1               5                   10                  15

Lys Ser Pro Val Val Ser Gly Asp Thr Ser Pro Arg His Leu
            20                  25                  30

<210> SEQ ID NO 59
<211> LENGTH: 16
<212> TYPE: PRT
<213> ORGANISM: artificial sequences
<220> FEATURE:
<221> NAME/KEY: SOURCE
<222> LOCATION: 1..16
<223> OTHER INFORMATION: /mol_type="protein"
      /note="Description of artificial sequence: ACI-33"
      /organism="artificial sequences"
<220> FEATURE:
<221> NAME/KEY: VARIANT
<222> LOCATION: 14..14
<223> OTHER INFORMATION: phosphorylated serine

<400> SEQUENCE: 59

Arg Gln Glu Phe Glu Val Met Glu Asp His Ala Gly Thr Tyr Gly Leu
1               5                   10                  15

<210> SEQ ID NO 60
<211> LENGTH: 16
<212> TYPE: PRT
<213> ORGANISM: artificial sequences
<220> FEATURE:
<221> NAME/KEY: SOURCE
<222> LOCATION: 1..16
<223> OTHER INFORMATION: /mol_type="protein"

```
        /note="Description of artificial sequence: ACI-39"
        /organism="artificial sequences"
<220> FEATURE:
<221> NAME/KEY: VARIANT
<222> LOCATION: 7..7
<223> OTHER INFORMATION: phosphorylated threonine
<220> FEATURE:
<221> NAME/KEY: VARIANT
<222> LOCATION: 9..9
<223> OTHER INFORMATION: phosphorylated serine

<400> SEQUENCE: 60

Pro Gly Ser Arg Ser Arg Thr Pro Ser Leu Pro Thr Pro Pro Thr Arg
1               5                   10                  15

<210> SEQ ID NO 61
<211> LENGTH: 16
<212> TYPE: PRT
<213> ORGANISM: artificial sequences
<220> FEATURE:
<221> NAME/KEY: SOURCE
<222> LOCATION: 1..16
<223> OTHER INFORMATION: /mol_type="protein"
        /note="Description of artificial sequence: ACI-39"
        /organism="Artificial Sequence"
<220> FEATURE:
<221> NAME/KEY: VARIANT
<222> LOCATION: 7..7
<223> OTHER INFORMATION: phosphorylated serine
<220> FEATURE:
<221> NAME/KEY: VARIANT
<222> LOCATION: 10..10
<223> OTHER INFORMATION: phosphorylated threonine

<400> SEQUENCE: 61

Gly Tyr Ser Ser Pro Gly Ser Pro Gly Thr Pro Gly Ser Arg Ser Arg
1               5                   10                  15

<210> SEQ ID NO 62
<211> LENGTH: 16
<212> TYPE: PRT
<213> ORGANISM: artificial sequences
<220> FEATURE:
<221> NAME/KEY: SOURCE
<222> LOCATION: 1..16
<223> OTHER INFORMATION: /mol_type="protein"
        /note="Description of artificial sequence: ACI-35"
        /organism="artificial sequences"
<220> FEATURE:
<221> NAME/KEY: VARIANT
<222> LOCATION: 4..4
<223> OTHER INFORMATION: phosphorylated serine
<220> FEATURE:
<221> NAME/KEY: VARIANT
<222> LOCATION: 12..12
<223> OTHER INFORMATION: phosphorylated serine

<400> SEQUENCE: 62

Val Tyr Lys Ser Pro Val Val Ser Gly Asp Thr Ser Pro Arg His Leu
1               5                   10                  15

<210> SEQ ID NO 63
<211> LENGTH: 18
<212> TYPE: PRT
<213> ORGANISM: artificial sequences
<220> FEATURE:
<221> NAME/KEY: SOURCE
<222> LOCATION: 1..18
<223> OTHER INFORMATION: /mol_type="protein"
        /note="Description of artificial sequence: ACI-36"
        /organism="artificial sequences"
<220> FEATURE:
<221> NAME/KEY: VARIANT
```

```
<222> LOCATION: 4..4
<223> OTHER INFORMATION: phosphorylated serine
<220> FEATURE:
<221> NAME/KEY: VARIANT
<222> LOCATION: 9..9
<223> OTHER INFORMATION: phosphorylated serine

<400> SEQUENCE: 63

Gly Asp Thr Ser Pro Arg His Leu Ser Asn Val Ser Ser Thr Gly Ser
1               5                   10                  15

Ile Asp

<210> SEQ ID NO 64
<211> LENGTH: 17
<212> TYPE: PRT
<213> ORGANISM: artificial sequences
<220> FEATURE:
<221> NAME/KEY: SOURCE
<222> LOCATION: 1..17
<223> OTHER INFORMATION: /mol_type="protein"
      /note="Description of artificial sequence: ACI-34"
      /organism="artificial sequences"
<220> FEATURE:
<221> NAME/KEY: VARIANT
<222> LOCATION: 3..3
<223> OTHER INFORMATION: phosphorylated serine
<220> FEATURE:
<221> NAME/KEY: VARIANT
<222> LOCATION: 6..6
<223> OTHER INFORMATION: phosphorylated threonine
<220> FEATURE:
<221> NAME/KEY: VARIANT
<222> LOCATION: 13..13
<223> OTHER INFORMATION: phosphorylated threonine
<220> FEATURE:
<221> NAME/KEY: VARIANT
<222> LOCATION: 15..15
<223> OTHER INFORMATION: phosphorylated serine

<400> SEQUENCE: 64

Pro Gly Ser Pro Gly Thr Pro Gly Ser Arg Ser Arg Thr Pro Ser Leu
1               5                   10                  15

Pro

<210> SEQ ID NO 65
<211> LENGTH: 12
<212> TYPE: PRT
<213> ORGANISM: artificial sequences
<220> FEATURE:
<221> NAME/KEY: SOURCE
<222> LOCATION: 1..12
<223> OTHER INFORMATION: /mol_type="protein"
      /note="Description of artificial sequence: ACI-42"
      /organism="artificial sequences"
<220> FEATURE:
<221> NAME/KEY: VARIANT
<222> LOCATION: 3..3
<223> OTHER INFORMATION: phosphorylated serine

<400> SEQUENCE: 65

His Leu Ser Asn Val Ser Ser Thr Gly Ser Ile Asp
1               5                   10

<210> SEQ ID NO 66
<211> LENGTH: 10
<212> TYPE: PRT
<213> ORGANISM: artificial sequences
<220> FEATURE:
<221> NAME/KEY: SOURCE
<222> LOCATION: 1..10
<223> OTHER INFORMATION: /mol_type="protein"
```

/note="Description of artificial sequence: ACI-43"
/organism="artificial sequences"
<220> FEATURE:
<221> NAME/KEY: VARIANT
<222> LOCATION: 6..6
<223> OTHER INFORMATION: phosphorylated serine

<400> SEQUENCE: 66

Val Ser Gly Asp Thr Ser Pro Arg His Leu
1               5                   10

<210> SEQ ID NO 67
<211> LENGTH: 441
<212> TYPE: PRT
<213> ORGANISM: Homo sapiens
<220> FEATURE:
<221> NAME/KEY: SOURCE
<222> LOCATION: 1..441
<223> OTHER INFORMATION: /mol_type="protein"
/organism="Homo sapiens"

<400> SEQUENCE: 67

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

-continued

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
                340                 345                 350

Lys Ile Gly Ser Leu Asp Asn Ile Thr His Val Pro Gly Gly Gly Asn
                355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
                435                 440

<210> SEQ ID NO 68
<211> LENGTH: 117
<212> TYPE: PRT
<213> ORGANISM: Mus musculus
<220> FEATURE:
<221> NAME/KEY: SOURCE
<222> LOCATION: 1..117
<223> OTHER INFORMATION: /mol_type="protein"
      /organism="Mus musculus"

<400> SEQUENCE: 68

Gln Val Gln Leu Gln Gln Pro Gly Ala Glu Leu Leu Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Arg Gly Leu Glu Trp Ile
            35                  40                  45

Gly Arg Ile Asp Pro Asn Ser Asp Arg Thr Lys Tyr Asn Glu Lys Phe
        50                  55                  60

Lys Arg Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Asp Tyr Ala Trp Phe Ala Tyr Trp Gly Gln Gly Thr Leu
                100                 105                 110

Val Thr Val Ser Ala
        115

<210> SEQ ID NO 69
<211> LENGTH: 112
<212> TYPE: PRT
<213> ORGANISM: Mus musculus
<220> FEATURE:
<221> NAME/KEY: SOURCE
<222> LOCATION: 1..112
<223> OTHER INFORMATION: /mol_type="protein"
      /organism="Mus musculus"

<400> SEQUENCE: 69

-continued

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Leu Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110
```

<210> SEQ ID NO 70
<211> LENGTH: 10
<212> TYPE: PRT
<213> ORGANISM: Mus musculus
<220> FEATURE:
<221> NAME/KEY: SOURCE
<222> LOCATION: 1..10
<223> OTHER INFORMATION: /mol_type="protein"
      /organism="Mus musculus"

<400> SEQUENCE: 70

```
Gly Tyr Thr Phe Thr Ser Tyr Trp Met His
1               5                   10
```

<210> SEQ ID NO 71
<211> LENGTH: 17
<212> TYPE: PRT
<213> ORGANISM: Mus musculus
<220> FEATURE:
<221> NAME/KEY: SOURCE
<222> LOCATION: 1..17
<223> OTHER INFORMATION: /mol_type="protein"
      /organism="Mus musculus"

<400> SEQUENCE: 71

```
Arg Ile Asp Pro Asn Ser Asp Arg Thr Lys Tyr Asn Glu Lys Phe Lys
1               5                   10                  15

Arg
```

<210> SEQ ID NO 72
<211> LENGTH: 8
<212> TYPE: PRT
<213> ORGANISM: Mus musculus
<220> FEATURE:
<221> NAME/KEY: SOURCE
<222> LOCATION: 1..8
<223> OTHER INFORMATION: /mol_type="protein"
      /organism="Mus musculus"

<400> SEQUENCE: 72

```
Asp Asp Tyr Ala Trp Phe Ala Tyr
1               5
```

<210> SEQ ID NO 73
<211> LENGTH: 16
<212> TYPE: PRT
<213> ORGANISM: Mus musculus
<220> FEATURE:
<221> NAME/KEY: SOURCE

```
<222> LOCATION: 1..16
<223> OTHER INFORMATION: /mol_type="protein"
      /organism="Mus musculus"

<400> SEQUENCE: 73

Arg Ser Ser Gln Ser Ile Val His Ser Asn Gly Asn Thr Tyr Leu Glu
1               5                   10                  15

<210> SEQ ID NO 74
<211> LENGTH: 7
<212> TYPE: PRT
<213> ORGANISM: Mus musculus
<220> FEATURE:
<221> NAME/KEY: SOURCE
<222> LOCATION: 1..7
<223> OTHER INFORMATION: /mol_type="protein"
      /organism="Mus musculus"

<400> SEQUENCE: 74

Lys Leu Ser Asn Arg Phe Ser
1               5

<210> SEQ ID NO 75
<211> LENGTH: 9
<212> TYPE: PRT
<213> ORGANISM: Mus musculus
<220> FEATURE:
<221> NAME/KEY: SOURCE
<222> LOCATION: 1..9
<223> OTHER INFORMATION: /mol_type="protein"
      /organism="Mus musculus"

<400> SEQUENCE: 75

Phe Gln Gly Ser His Val Pro Pro Thr
1               5

<210> SEQ ID NO 76
<211> LENGTH: 119
<212> TYPE: PRT
<213> ORGANISM: Mus musculus
<220> FEATURE:
<221> NAME/KEY: SOURCE
<222> LOCATION: 1..119
<223> OTHER INFORMATION: /mol_type="protein"
      /organism="Mus musculus"

<400> SEQUENCE: 76

Gln Val Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Ser Thr Ser
                20                  25                  30

Gly Met Gly Val Ser Trp Ile Arg Gln Pro Ser Gly Lys Gly Leu Glu
            35                  40                  45

Trp Leu Ala His Ile Tyr Trp Asp Asp Lys Arg Tyr Asn Ala Ser
        50                  55                  60

Leu Lys Ser Arg Leu Thr Ile Ser Lys Asp Thr Ser Arg Asn Gln Val
65                  70                  75                  80

Phe Leu Lys Ile Thr Cys Val Asp Thr Ala Asp Thr Ala Thr Tyr Tyr
                85                  90                  95

Cys Ala Arg Leu Leu Arg Pro Tyr Ala Leu Asp Tyr Trp Gly Gln Gly
                100                 105                 110

Thr Ser Val Thr Val Ser Ser
            115
```

```
<210> SEQ ID NO 77
<211> LENGTH: 112
<212> TYPE: PRT
<213> ORGANISM: Mus musculus
<220> FEATURE:
<221> NAME/KEY: SOURCE
<222> LOCATION: 1..112
<223> OTHER INFORMATION: /mol_type="protein"
      /organism="Mus musculus"

<400> SEQUENCE: 77
```

Asn Ile Leu Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Leu Gln
                85                  90                  95

Tyr Leu Ser Ser Leu Thr Phe Gly Ala Gly Thr Lys Leu Glu Leu Lys
            100                 105                 110

```
<210> SEQ ID NO 78
<211> LENGTH: 12
<212> TYPE: PRT
<213> ORGANISM: Mus musculus
<220> FEATURE:
<221> NAME/KEY: SOURCE
<222> LOCATION: 1..12
<223> OTHER INFORMATION: /mol_type="protein"
      /organism="Mus musculus"

<400> SEQUENCE: 78
```

Gly Phe Ser Leu Ser Thr Ser Gly Met Gly Val Ser
1               5                   10

```
<210> SEQ ID NO 79
<211> LENGTH: 16
<212> TYPE: PRT
<213> ORGANISM: Mus musculus
<220> FEATURE:
<221> NAME/KEY: SOURCE
<222> LOCATION: 1..16
<223> OTHER INFORMATION: /mol_type="protein"
      /organism="Mus musculus"

<400> SEQUENCE: 79
```

His Ile Tyr Trp Asp Asp Asp Lys Arg Tyr Asn Ala Ser Leu Lys Ser
1               5                   10                  15

```
<210> SEQ ID NO 80
<211> LENGTH: 9
<212> TYPE: PRT
<213> ORGANISM: Mus musculus
<220> FEATURE:
<221> NAME/KEY: SOURCE
<222> LOCATION: 1..9
<223> OTHER INFORMATION: /mol_type="protein"
      /organism="Mus musculus"

<400> SEQUENCE: 80
```

Leu Leu Arg Pro Tyr Ala Leu Asp Tyr

<210> SEQ ID NO 81
<211> LENGTH: 17
<212> TYPE: PRT
<213> ORGANISM: Mus musculus
<220> FEATURE:
<221> NAME/KEY: SOURCE
<222> LOCATION: 1..17
<223> OTHER INFORMATION: /mol_type="protein"
      /organism="Mus musculus"

<400> SEQUENCE: 81

Lys Ser Ser Gln Ser Val Leu Tyr Ser Ser Asn Gln Lys Asn Tyr Leu
1               5                   10                  15
Ala

<210> SEQ ID NO 82
<211> LENGTH: 7
<212> TYPE: PRT
<213> ORGANISM: Mus musculus
<220> FEATURE:
<221> NAME/KEY: SOURCE
<222> LOCATION: 1..7
<223> OTHER INFORMATION: /mol_type="protein"
      /organism="Mus musculus"

<400> SEQUENCE: 82

Trp Ala Ser Thr Arg Glu Ser
1               5

<210> SEQ ID NO 83
<211> LENGTH: 8
<212> TYPE: PRT
<213> ORGANISM: Mus musculus
<220> FEATURE:
<221> NAME/KEY: SOURCE
<222> LOCATION: 1..8
<223> OTHER INFORMATION: /mol_type="protein"
      /organism="Mus musculus"

<400> SEQUENCE: 83

Leu Gln Tyr Leu Ser Ser Leu Thr
1               5

<210> SEQ ID NO 84
<211> LENGTH: 351
<212> TYPE: DNA
<213> ORGANISM: Mus musculus
<220> FEATURE:
<221> NAME/KEY: source
<222> LOCATION: 1..351
<223> OTHER INFORMATION: /mol_type="DNA"
      /organism="Mus musculus"

<400> SEQUENCE: 84
caggtccaac tgcagcagcc tggggctgag cttctgaagc ctggggcttc agtgaaactg      60
tcctgcaagg cttctggcta caccttcacc agctactgga tgcactgggt gaagcagagg     120
cctggacgag ccttgagtg gattggaagg attgatccta atagtgatcg tactaagtac      180
aatgagaagt tcaagcgcaa ggccacactg actgtagaca atcctccag cacagcctac      240 atgcagctca gcagcctgac atctgaggac tctgcggtct attattgtgc aagggatgat     300
tacgcctggt ttgcttactg gggccaaggg actctggtca ctgtctctgc a              351

<210> SEQ ID NO 85

```
<211> LENGTH: 336
<212> TYPE: DNA
<213> ORGANISM: Mus musculus
<220> FEATURE:
<221> NAME/KEY: source
<222> LOCATION: 1..336
<223> OTHER INFORMATION: /mol_type="DNA"
      /organism="Mus musculus"

<400> SEQUENCE: 85
gatgttttga tgacccaaac tccactctcc ctgcctgtca gtcttggaga tcaagcctcc      60
atctcttgca gatctagtca gagcattgta catagtaatg gaaacaccta tttagaatgg     120
tacctgcaga aaccaggcca gtctccaaag ctcctgatct acaaactttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttcct     300
ccgacgttcg gtggaggcac caagctggaa atcaaa                               336

<210> SEQ ID NO 86
<211> LENGTH: 357
<212> TYPE: DNA
<213> ORGANISM: Mus musculus
<220> FEATURE:
<221> NAME/KEY: source
<222> LOCATION: 1..357
<223> OTHER INFORMATION: /mol_type="DNA"
      /organism="Mus musculus"

<400> SEQUENCE: 86
caggttactc tgaaagagtc tggccctggg atattgcagt cctcccagac cctcagtctg      60
acttgttctt tctctgggtt ttcactgagc acttctggta tgggtgtgag ctggattcgt     120
cagccttcag gaaagggtct ggagtggctg gcacacattt actgggatga tgacaagcgc     180
tataacgcat ccctgaagag ccggctcaca atctccaagg atacctccag aaaccaggta     240
ttcctcaaga tcacctgtgt ggacactgca gatactgcca catactactg tgctcggtta     300
ctgcgtcctt atgctttgga ctactggggt caaggaacct cagtcaccgt ctcctca       357

<210> SEQ ID NO 87
<211> LENGTH: 336
<212> TYPE: DNA
<213> ORGANISM: Mus musculus
<220> FEATURE:
<221> NAME/KEY: source
<222> LOCATION: 1..336
<223> OTHER INFORMATION: /mol_type="DNA"
      /organism="Mus musculus"

<400> SEQUENCE: 87
aacattttga tgacacagtc gccatcatct ctggctgtgt ctgcaggaga aaaggtcact      60
atgagctgta agtccagtca aagtgtttta tacagttcaa atcagaagaa ctacttggcc     120
tggtaccagc agaaaccagg gcagtctcct aaactgctga tctactgggc atccactagg     180
gaatctggtg tccctgatcg cttcacaggc agtggatctg gacagattt tactcttacc     240 atcagcagtg tacaagctga agacctggca gtttattact gtcttcaata cctctcctcg     300
ctcacgttcg gtgctgggac caagctggag ctgaaa                               336

<210> SEQ ID NO 88
<211> LENGTH: 115
<212> TYPE: PRT
<213> ORGANISM: Mus musculus
<220> FEATURE:
```

```
<221> NAME/KEY: SOURCE
<222> LOCATION: 1..115
<223> OTHER INFORMATION: /mol_type="protein"
      /organism="Mus musculus"

<400> SEQUENCE: 88

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Gly Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Val Arg Glu Gly Arg Phe Ala Tyr Trp Gly His Gly Thr Leu Val Thr
            100                 105                 110

Val Ser Ala
        115

<210> SEQ ID NO 89
<211> LENGTH: 10
<212> TYPE: PRT
<213> ORGANISM: Mus musculus
<220> FEATURE:
<221> NAME/KEY: SOURCE
<222> LOCATION: 1..10
<223> OTHER INFORMATION: /mol_type="protein"
      /organism="Mus musculus"

<400> SEQUENCE: 89

Gly Phe Thr Phe Thr Asp Tyr Tyr Met Asn
1               5                   10

<210> SEQ ID NO 90
<211> LENGTH: 17
<212> TYPE: PRT
<213> ORGANISM: Mus musculus
<220> FEATURE:
<221> NAME/KEY: SOURCE
<222> LOCATION: 1..17
<223> OTHER INFORMATION: /mol_type="protein"
      /organism="Mus musculus"

<400> SEQUENCE: 90

Asp Ile Asn Pro Asn Asn Gly Gly Thr Ser Tyr Asn Gln Lys Phe Lys
1               5                   10                  15

Gly

<210> SEQ ID NO 91
<211> LENGTH: 6
<212> TYPE: PRT
<213> ORGANISM: Mus musculus
<220> FEATURE:
<221> NAME/KEY: SOURCE
<222> LOCATION: 1..6
<223> OTHER INFORMATION: /mol_type="protein"
      /organism="Mus musculus"

<400> SEQUENCE: 91

Glu Gly Arg Phe Ala Tyr
```

-continued

<210> SEQ ID NO 92
<211> LENGTH: 112
<212> TYPE: PRT
<213> ORGANISM: Mus musculus
<220> FEATURE:
<221> NAME/KEY: SITE
<222> LOCATION: 3..3
<223> OTHER INFORMATION: Xaa is Met or Val
<220> FEATURE:
<221> NAME/KEY: SOURCE
<222> LOCATION: 1..112
<223> OTHER INFORMATION: /mol_type="protein"
      /organism="Mus musculus"

<400> SEQUENCE: 92

Asp Ile Xaa Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Lys Ser Pro Tyr Thr Phe Gly Gly Gly Thr Lys Leu Glu Ile Lys
                100                 105                 110

<210> SEQ ID NO 93
<211> LENGTH: 16
<212> TYPE: PRT
<213> ORGANISM: Mus musculus
<220> FEATURE:
<221> NAME/KEY: SOURCE
<222> LOCATION: 1..16
<223> OTHER INFORMATION: /mol_type="protein"
      /organism="Mus musculus"

<400> SEQUENCE: 93

Arg Ser Ser Lys Ser Leu Leu His Ser Asn Gly Asn Thr Tyr Leu Tyr
1               5                   10                  15

<210> SEQ ID NO 94
<211> LENGTH: 7
<212> TYPE: PRT
<213> ORGANISM: Mus musculus
<220> FEATURE:
<221> NAME/KEY: SOURCE
<222> LOCATION: 1..7
<223> OTHER INFORMATION: /mol_type="protein"
      /organism="Mus musculus"

<400> SEQUENCE: 94

Arg Met Ser Asn Leu Ala Ser
1               5

<210> SEQ ID NO 95
<211> LENGTH: 9
<212> TYPE: PRT
<213> ORGANISM: Mus musculus
<220> FEATURE:
<221> NAME/KEY: SOURCE

```
<222> LOCATION: 1..9
<223> OTHER INFORMATION: /mol_type="protein"
      /organism="Mus musculus"

<400> SEQUENCE: 95

Met Gln His Leu Lys Ser Pro Tyr Thr
1               5

<210> SEQ ID NO 96
<211> LENGTH: 115
<212> TYPE: PRT
<213> ORGANISM: Mus musculus
<220> FEATURE:
<221> NAME/KEY: SOURCE
<222> LOCATION: 1..115
<223> OTHER INFORMATION: /mol_type="protein"
      /organism="Mus musculus"

<400> SEQUENCE: 96

Gln Val Gln Leu Lys Gln Ser Gly Ala Glu Leu Val Arg Pro Gly Ala
1               5                   10                  15

Ser Val Lys Leu Ser Cys Lys Ala Ser Gly Tyr Thr Phe Thr Asp Tyr
                20                  25                  30

Tyr Ile Asn Trp Val Lys Gln Arg Pro Gly Gln Gly Leu Glu Trp Ile
            35                  40                  45

Ala Arg Ile Tyr Pro Gly Arg Gly Asn Ile Tyr Tyr Asn Glu Lys Phe
        50                  55                  60

Lys Gly Lys Ala Thr Leu Thr Ala Glu Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Phe Trp Asp Val Thr Tyr Trp Gly Gln Gly Thr Leu Val Thr
            100                 105                 110

Val Ser Ala
        115

<210> SEQ ID NO 97
<211> LENGTH: 112
<212> TYPE: PRT
<213> ORGANISM: Mus musculus
<220> FEATURE:
<221> NAME/KEY: SOURCE
<222> LOCATION: 1..112
<223> OTHER INFORMATION: /mol_type="protein"
      /organism="Mus musculus"

<400> SEQUENCE: 97

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Glu Trp Phe Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110
```

<210> SEQ ID NO 98
<211> LENGTH: 10
<212> TYPE: PRT
<213> ORGANISM: Mus musculus
<220> FEATURE:
<221> NAME/KEY: SOURCE
<222> LOCATION: 1..10
<223> OTHER INFORMATION: /mol_type="protein"
      /organism="Mus musculus"

<400> SEQUENCE: 98

Gly Tyr Thr Phe Thr Asp Tyr Tyr Ile Asn
1               5                   10

<210> SEQ ID NO 99
<211> LENGTH: 17
<212> TYPE: PRT
<213> ORGANISM: Mus musculus
<220> FEATURE:
<221> NAME/KEY: SOURCE
<222> LOCATION: 1..17
<223> OTHER INFORMATION: /mol_type="protein"
      /organism="Mus musculus"

<400> SEQUENCE: 99

Arg Ile Tyr Pro Gly Arg Gly Asn Ile Tyr Tyr Asn Glu Lys Phe Lys
1               5                   10                  15

Gly

<210> SEQ ID NO 100
<211> LENGTH: 6
<212> TYPE: PRT
<213> ORGANISM: Mus musculus
<220> FEATURE:
<221> NAME/KEY: SOURCE
<222> LOCATION: 1..6
<223> OTHER INFORMATION: /mol_type="protein"
      /organism="Mus musculus"

<400> SEQUENCE: 100

Phe Trp Asp Val Thr Tyr
1               5

<210> SEQ ID NO 101
<211> LENGTH: 16
<212> TYPE: PRT
<213> ORGANISM: Mus musculus
<220> FEATURE:
<221> NAME/KEY: SOURCE
<222> LOCATION: 1..16
<223> OTHER INFORMATION: /mol_type="protein"
      /organism="Mus musculus"

<400> SEQUENCE: 101

Arg Ser Ser Gln Ser Ile Val His Ser Asn Gly Asn Thr Tyr Leu Glu
1               5                   10                  15

<210> SEQ ID NO 102
<211> LENGTH: 7
<212> TYPE: PRT
<213> ORGANISM: Mus musculus
<220> FEATURE:
<221> NAME/KEY: SOURCE
<222> LOCATION: 1..7
<223> OTHER INFORMATION: /mol_type="protein"
      /organism="Mus musculus"

<400> SEQUENCE: 102

```
Lys Val Ser Asn Arg Phe Ser
1               5
```

<210> SEQ ID NO 103
<211> LENGTH: 9
<212> TYPE: PRT
<213> ORGANISM: Mus musculus
<220> FEATURE:
<221> NAME/KEY: SOURCE
<222> LOCATION: 1..9
<223> OTHER INFORMATION: /mol_type="protein"
      /organism="Mus musculus"

<400> SEQUENCE: 103

```
Phe Gln Gly Ser His Val Pro Tyr Thr
1               5
```

<210> SEQ ID NO 104
<211> LENGTH: 115
<212> TYPE: PRT
<213> ORGANISM: Mus musculus
<220> FEATURE:
<221> NAME/KEY: SOURCE
<222> LOCATION: 1..115
<223> OTHER INFORMATION: /mol_type="protein"
      /organism="Mus musculus"

<400> SEQUENCE: 104

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Phe Thr Phe Thr Asp Tyr
                20                  25                  30

Tyr Met Asn Trp Val Lys Gln Ser His Gly Lys Ser Leu Glu Trp Ile
            35                  40                  45

Gly Asp Ile Asn Pro Asn Asn Gly Gly Thr Ser Tyr His Gln Lys Phe
        50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Val Arg Glu Gly Arg Phe Ala Tyr Trp Gly Gln Gly Thr Leu Val Thr
                100                 105                 110

Val Ser Ala
        115
```

<210> SEQ ID NO 105
<211> LENGTH: 107
<212> TYPE: PRT
<213> ORGANISM: Mus musculus
<220> FEATURE:
<221> NAME/KEY: SOURCE
<222> LOCATION: 1..107
<223> OTHER INFORMATION: /mol_type="protein"
      /organism="Mus musculus"

<400> SEQUENCE: 105

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Ala Leu Ile
            35                  40                  45
```

Tyr Ser Ala Ser Tyr Arg Tyr Ser Gly Val Pro Asp Arg Phe Thr Gly
            50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Asn Ser Tyr Pro Tyr
                 85                  90                  95

Thr Phe Gly Gly Gly Thr Lys Leu Glu Ile Lys
            100                 105

<210> SEQ ID NO 106
<211> LENGTH: 11
<212> TYPE: PRT
<213> ORGANISM: Mus musculus
<220> FEATURE:
<221> NAME/KEY: SOURCE
<222> LOCATION: 1..11
<223> OTHER INFORMATION: /mol_type="protein"
      /organism="Mus musculus"

<400> SEQUENCE: 106

Lys Ala Ser Gln Asn Val Gly Thr Asn Val Ala
1               5                   10

<210> SEQ ID NO 107
<211> LENGTH: 7
<212> TYPE: PRT
<213> ORGANISM: Mus musculus
<220> FEATURE:
<221> NAME/KEY: SOURCE
<222> LOCATION: 1..7
<223> OTHER INFORMATION: /mol_type="protein"
      /organism="Mus musculus"

<400> SEQUENCE: 107

Ser Ala Ser Tyr Arg Tyr Ser
1               5

<210> SEQ ID NO 108
<211> LENGTH: 9
<212> TYPE: PRT
<213> ORGANISM: Mus musculus
<220> FEATURE:
<221> NAME/KEY: SOURCE
<222> LOCATION: 1..9
<223> OTHER INFORMATION: /mol_type="protein"
      /organism="Mus musculus"

<400> SEQUENCE: 108

Gln Gln Tyr Asn Ser Tyr Pro Tyr Thr
1               5

<210> SEQ ID NO 109
<211> LENGTH: 345
<212> TYPE: DNA
<213> ORGANISM: Mus musculus
<220> FEATURE:
<221> NAME/KEY: source
<222> LOCATION: 1..345
<223> OTHER INFORMATION: /mol_type="DNA"
      /organism="Mus musculus"

<400> SEQUENCE: 109
gaggtccagc tgcaacaatc tggacctgag ctggtgaagc ctggggcttc agtgaagata      60
tcctgtaagg cttctggata cacgttcact gactactaca tgaactgggt gaagcagagc     120
catggaaaga gccttgagtg gattggagat attaatccta caatggtgg tactagctac      180

```
aaccagaagt tcaagggcaa ggccacattg actgtagaca agtcctccag cacagcctac    240
atggagctcc gcagtctgac atctgaggac tctgcagtct attattgtgt aagagagggg    300
cggtttgctt actggggtca tgggactctg gtcactgtct ctgca                    345
```

<210> SEQ ID NO 110
<211> LENGTH: 336
<212> TYPE: DNA
<213> ORGANISM: Mus musculus
<220> FEATURE:
<221> NAME/KEY: source
<222> LOCATION: 1..336
<223> OTHER INFORMATION: /mol_type="DNA"
      /organism="Mus musculus"

<400> SEQUENCE: 110

```
gatattrtga tgactcaggc tgcaccctct gtacctgtca ctcctggaga gtcagtatcc     60
atctcctgca ggtctagtaa gagtctcctg catagtaatg gcaacactta cttgtattgg    120
ttcctgcaga ggccaggcca gtcctccag ctcctgatat atcggatgtc caaccttgcc     180
tcaggagtcc cagacaggtt cagtggcagt gggtcaggaa ctgctttcac actgagaatc    240
agtagagtgg aggctgagga tgtgggtgtt tattactgta tgcaacatct aaaatctccg    300
tacacgttcg gaggggggac caagctggaa ataaaa                              336
```

<210> SEQ ID NO 111
<211> LENGTH: 345
<212> TYPE: DNA
<213> ORGANISM: Mus musculus
<220> FEATURE:
<221> NAME/KEY: source
<222> LOCATION: 1..345
<223> OTHER INFORMATION: /mol_type="DNA"
      /organism="Mus musculus"

<400> SEQUENCE: 111

```
caggtccagc tgaagcagtc tggggctgag ctggtgaggc ctggggcttc agtgaaactg     60
tcctgcaagg cttctggcta cactttcact gactactata taaactgggt gaagcagagg    120
cctggacagg gacttgagtg gattgcaagg atttatcctg gaagaggtaa tatttactac    180
aatgagaagt tcaagggcaa ggccacactg actgcagaaa aatcctccag cactgcctac    240
atgcagctca gcagcctgac atctgaggac tctgctgtct atttctgtgc aagattctgg    300
gacgtgactt actggggcca aggactctg gtcactgtct ctgca                     345
```

<210> SEQ ID NO 112
<211> LENGTH: 336
<212> TYPE: DNA
<213> ORGANISM: Mus musculus
<220> FEATURE:
<221> NAME/KEY: source
<222> LOCATION: 1..336
<223> OTHER INFORMATION: /mol_type="DNA"
      /organism="Mus musculus"

<400> SEQUENCE: 112

```
gatgttttga tgacccaaac tccactctcc ctgcctgtca gtcttggaga tcaagcctcc     60
atctcttgca gatctagtca gagcattgta catagtaatg gaaacaccta tttagaatgg    120
ttcctgcaga aaccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttccg    300
```

```
tacacgttcg gagggggggac caagctggaa ataaaa                                    336
```

<210> SEQ ID NO 113
<211> LENGTH: 345
<212> TYPE: DNA
<213> ORGANISM: Mus musculus
<220> FEATURE:
<221> NAME/KEY: source
<222> LOCATION: 1..345
<223> OTHER INFORMATION: /mol_type="DNA"
      /organism="Mus musculus"

<400> SEQUENCE: 113

```
gaggtccagc tgcaacaatc tggacctgag ctggtgaagc ctggggcttc agtgaagata           60
tcctgtaagg cttctggatt cacgttcact gactactaca tgaactgggt gaagcagagc          120
catggaaaga gccttgagtg gattggagat attaatccta acaatggtgg tactagctac          180
caccagaagt tcaagggcaa ggccacattg actgtagaca gtcctccag cacagcctac           240 atggagctcc gcagcctgac atctgaggac tctgcagtct attactgtgt aagagaggga          300
agatttgctt actggggcca aggactctg gtcactgtct ctgca                           345
```

<210> SEQ ID NO 114
<211> LENGTH: 321
<212> TYPE: DNA
<213> ORGANISM: Mus musculus
<220> FEATURE:
<221> NAME/KEY: source
<222> LOCATION: 1..321
<223> OTHER INFORMATION: /mol_type="DNA"
      /organism="Mus musculus"

<400> SEQUENCE: 114

```
gacattgtga tgacccagtc tcaaaaattc atgtccacat cagtaggaga cagggtcagc           60
gtcacctgca aggccagtca gaatgtgggt actaatgtag cctggtatca acagaaacca          120
gggcaatctc ctaaagcact gatttactcg gcatcctacc ggtacagtgg agtccctgat          180
cgcttcacag gcagtggatc tgggacagat ttcactctca ccatcagcaa tgtgcagtct          240
gaagacttgg cagagtattt ctgtcagcaa tataacagct atccgtacac gttcggaggg          300
gggaccaagc tggaaataaa a                                                    321
```

<210> SEQ ID NO 115
<211> LENGTH: 17
<212> TYPE: PRT
<213> ORGANISM: Mus musculus
<220> FEATURE:
<221> NAME/KEY: SOURCE
<222> LOCATION: 1..17
<223> OTHER INFORMATION: /mol_type="protein"
      /organism="Mus musculus"

<400> SEQUENCE: 115

```
Asp Ile Asn Pro Asn Asn Gly Gly Thr Ser Tyr His Gln Lys Phe Lys
1               5                   10                  15

Gly
```

<210> SEQ ID NO 116
<211> LENGTH: 112
<212> TYPE: PRT
<213> ORGANISM: Mus musculus
<220> FEATURE:
<221> NAME/KEY: SOURCE
<222> LOCATION: 1..112
<223> OTHER INFORMATION: /mol_type="protein"

-continued

/organism="Mus musculus"

<400> SEQUENCE: 116

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile His Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Lys Ser Pro Tyr Thr Phe Gly Gly Gly Thr Lys Leu Glu Ile Lys
            100                 105                 110

<210> SEQ ID NO 117
<211> LENGTH: 336
<212> TYPE: DNA
<213> ORGANISM: Mus musculus
<220> FEATURE:
<221> NAME/KEY: source
<222> LOCATION: 1..336
<223> OTHER INFORMATION: /mol_type="DNA"
      /organism="Mus musculus"

<400> SEQUENCE: 117
gatattgtga tgactcaggc tgcaccctct gtacctgtca ctcctggaga gtcagtatcc      60
atctcctgca ggtctagtaa gagtctcctg catagtaatg caacacttac cttgtattgg     120
ttcctgcaga ggccaggcca gtctcctcag ctcctgatac atcggatgtc caaccttgcc    180
tcaggagtcc cagacaggtt cagtggcagt gggtcaggaa ctgctttcac actgagaatc    240
agtagagtgg aggctgagga tgtgggtgtt tattactgta tgcaacatct aaaatctccg    300
tacacgttcg gagggggac caagctggaa ataaaa                                336

<210> SEQ ID NO 118
<211> LENGTH: 112
<212> TYPE: PRT
<213> ORGANISM: Mus musculus
<220> FEATURE:
<221> NAME/KEY: SOURCE
<222> LOCATION: 1..112
<223> OTHER INFORMATION: /mol_type="protein"
      /organism="Mus musculus"

<400> SEQUENCE: 118

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His

```
                85                  90                  95
Leu Lys Ser Pro Tyr Thr Phe Gly Gly Gly Thr Lys Leu Glu Ile Lys
            100                 105                 110
```

<210> SEQ ID NO 119
<211> LENGTH: 336
<212> TYPE: DNA
<213> ORGANISM: Mus musculus
<220> FEATURE:
<221> NAME/KEY: source
<222> LOCATION: 1..336
<223> OTHER INFORMATION: /mol_type="DNA"
      /organism="Mus musculus"

<400> SEQUENCE: 119
gatattgtga tgactcaggc tgcaccctct gtacctgtca ctcctggaga gtcagtatcc       60
atctcctgca ggtctagtaa gagtctcctg catagtaatg caacactta cttgtattgg      120 ttcctgcaga ggccaggcca gtctcctcag ctcctgatat atcggatgtc caaccttgcc     180
tcaggagtcc cagacaggtt cagtggcagt gggtcaggaa ctgctttcac actgagaatc     240
agtagagtgg aggctgagga tgtgggtgtt tattactgta tgcaacatct aaaatctccg     300
tacacgttcg gaggggggac caagctggaa ataaaa                                336

<210> SEQ ID NO 120
<211> LENGTH: 34
<212> TYPE: DNA
<213> ORGANISM: artificial sequences
<220> FEATURE:
<221> NAME/KEY: source
<222> LOCATION: 1..34
<223> OTHER INFORMATION: /mol_type="DNA"
      /note="Description of artificial sequence: primer"
      /organism="artificial sequences"

<400> SEQUENCE: 120
gggaattcat ggaatgcagc tgggtttttc tctt                                  34

<210> SEQ ID NO 121
<211> LENGTH: 34
<212> TYPE: DNA
<213> ORGANISM: artificial sequences
<220> FEATURE:
<221> NAME/KEY: source
<222> LOCATION: 1..34
<223> OTHER INFORMATION: /mol_type="DNA"
      /note="Description of artificial sequence: primer"
      /organism="artificial sequences"

<400> SEQUENCE: 121
gggaattcat ggaatggagc tgggtctttc tctt                                  34

<210> SEQ ID NO 122
<211> LENGTH: 34
<212> TYPE: DNA
<213> ORGANISM: artificial sequences
<220> FEATURE:
<221> NAME/KEY: source
<222> LOCATION: 1..34
<223> OTHER INFORMATION: /mol_type="DNA"
      /note="Description of artificial sequence: primer"
      /organism="artificial sequences"

<400> SEQUENCE: 122
gggaattcat ggaatgcagc tgggtcattc tctt                                  34

```
<210> SEQ ID NO 123
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 123
gggaattcat ggaatggagc tgggttttc tctt                          34

<210> SEQ ID NO 124
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 124
gggaattcat ggaatggagc tgggttattc tctt                          34

<210> SEQ ID NO 125
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 125
gggaattcat ggaatggagc tgggttattc tctt                          34

<210> SEQ ID NO 126
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 126
gggaattcat ggaatgcagc tgggtcttcc tctt                          34

<210> SEQ ID NO 127
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 127
gggaattcat ggaatggagc tgggttttcc tcttc                         35
```

```
<210> SEQ ID NO 128
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 128
cccaagcttc cagggaccaa tggataacgg gtgg                              34

<210> SEQ ID NO 129
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 129
cccaagcttc cagggaccaa tggataaacg atgg                              34

<210> SEQ ID NO 130
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 130
cccaagcttc cagggaccaa tggataaacg gtgg                              34

<210> SEQ ID NO 131
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 131
cccaagcttc cagggaccaa tggataaacg gatgg                             35

<210> SEQ ID NO 132
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 132
cccaagcttc cagggaccag tggatagacg ggtgg                             35
```

<210> SEQ ID NO 133
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 133
cccaagcttc cagggaccaa gggatagatg atgg                              34

<210> SEQ ID NO 134
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 134
cccaagcttc caggggccaa tggataaacg ggtgg                             35

<210> SEQ ID NO 135
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 135
cccaagcttc caggggccaa tggataaacg atgg                              34

<210> SEQ ID NO 136
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 136
gggaattcat ggaatggagc tgggtcattc tctt                              34

<210> SEQ ID NO 137
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 137
gggaattcat ggaatgcacc tgggttttcc tctt                              34

<210> SEQ ID NO 138
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 138
gggaattcat ggaatggagc tgggtcttcc tctt                              34

<210> SEQ ID NO 139
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 139
gggaattcat ggaatggagc tgggtcatcc tctt                              34

<210> SEQ ID NO 140
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 140
actagtcgac atgggatgag cttatcatcc tctt                              34

<210> SEQ ID NO 141
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="DNA"
      /note="Description of artificial sequence: primer"
      /organism="Artificial Sequence"

<400> SEQUENCE: 141
cccaagcttc cagggccaa tggataacgg tgg                                33

<210> SEQ ID NO 142
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="DNA"
      /note="Description of artificial sequence: primer"
      /organism="Artificial Sequence"

<400> SEQUENCE: 142

-continued

```
cccaagcttc cagggaccag tgggataaac gggtgg                                36
```

<210> SEQ ID NO 143
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
    /note="Description of artificial sequence: primer"
    /organism="Artificial Sequence"

<400> SEQUENCE: 143

```
cccaagcttc cagggaccaa gggatagacg ggtgg                                 35
```

<210> SEQ ID NO 144
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
    /note="Description of artificial sequence: primer"
    /organism="Artificial Sequence"

<400> SEQUENCE: 144

```
cccaagcttc cagggaccaa gggataaacg gatgg                                 35
```

<210> SEQ ID NO 145
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
    /note="Description of artificial sequence: primer"
    /organism="Artificial Sequence"

<400> SEQUENCE: 145

```
cccaagcttc cagggaccag gggataaacg gatgg                                 35
```

<210> SEQ ID NO 146
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
    /note="Description of artificial sequence: primer"
    /organism="Artificial Sequence"

<400> SEQUENCE: 146

```
cccaagcttc caggggccag ggataaacgg gtgg                                  34
```

<210> SEQ ID NO 147
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
    /note="Description of artificial sequence: primer"
    /organism="Artificial Sequence"

<400> SEQUENCE: 147
cccaagcttc cagggggccaa tggataaacc ggtgg        35

<210> SEQ ID NO 148
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 148
cccaagcttc cagggaccag tggataaacg gtgg        34

<210> SEQ ID NO 149
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 149
actagtcgac atggtgtcca cagctcagtt ccttg        35

<210> SEQ ID NO 150
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 150
gggaattcat gaaatggagc tgggtcttcc tctt        34

<210> SEQ ID NO 151
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 151
gggaattcat ggaatgcagc tgggttattc tctt        34

<210> SEQ ID NO 152
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 152
gggaatttat ggaatggagc tgggtcttcc tctt    34

<210> SEQ ID NO 153
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 153
gggaattcat ggaatgcagc tgggtcatcc tctt    34

<210> SEQ ID NO 154
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 154
gggaattcat ggaatgcagc tgggttttcc tctt    34

<210> SEQ ID NO 155
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 155
gggaattcat ggaatgcagc tgggtctttc tctt    34

<210> SEQ ID NO 156
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="DNA"
      /note="Description of artificial sequence: primer"
      /organism="Artificial Sequence"

<400> SEQUENCE: 156
actagtcgac atgggatgga gctatatcat cctctt    36

<210> SEQ ID NO 157
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"

/organism="Artificial Sequence"

<400> SEQUENCE: 157
actagtcgac atgggatgga gcttatcatc ttctt                35

<210> SEQ ID NO 158
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="DNA"
      /note="Description of artificial sequence: primer"
      /organism="Artificial Sequence"

<400> SEQUENCE: 158
actagtcgac atgtagatgt ggttaaactg ggt                  33

<210> SEQ ID NO 159
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 159
cccaagcttc caggggccag gggataaacg gatgg                35

<210> SEQ ID NO 160
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 160
cccaagcttc caggggccaa gggatagacg gatgg                35

<210> SEQ ID NO 161
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 161
cccaagcttc cagggaccag gggatagacg ggtgg                35

<210> SEQ ID NO 162
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"

```
      /note="Description of artificial sequence: primer"
      /organism="Artificial Sequence"

<400> SEQUENCE: 162
cccaagcttc cagggaccag gggatagacg gatgg                               35

<210> SEQ ID NO 163
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 163
cccaagcttc caggggccag tggataaacg gatgg                               35

<210> SEQ ID NO 164
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="DNA"
      /note="Description of artificial sequence: primer"
      /organism="Artificial Sequence"

<400> SEQUENCE: 164
cccaagcttc caggggccaa tggataacga tgg                                 33

<210> SEQ ID NO 165
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 165
cccaagcttc caggggccag tggataaacg atgg                                34

<210> SEQ ID NO 166
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 166
cccaagcttc cagggaccag tggataaacg atgg                                34

<210> SEQ ID NO 167
<211> LENGTH: 33
<212> TYPE: DNA
<213> ORGANISM: Artificial Sequence
<220> FEATURE:
<221> NAME/KEY: source
<222> LOCATION: 1..33
```

```
<223> OTHER INFORMATION: /mol_type="DNA"
        /note="Description of artificial sequence: primer"
        /organism="Artificial Sequence"

<400> SEQUENCE: 167
cccaagcttc cagggaccaa tggataacga tgg                                    33

<210> SEQ ID NO 168
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
        /note="Description of artificial sequence: primer"
        /organism="Artificial Sequence"

<400> SEQUENCE: 168
cccaagcttc cagggaccat ggataaacgg gtgg                                   34

<210> SEQ ID NO 169
<211> LENGTH: 41
<212> TYPE: DNA
<213> ORGANISM: Artificial Sequence
<220> FEATURE:
<221> NAME/KEY: source
<222> LOCATION: 1..41
<223> OTHER INFORMATION: /mol_type="DNA"
        /note="Description of artificial sequence: primer"
        /organism="Artificial Sequence"

<400> SEQUENCE: 169
actagtcgac atgggcatca agatgaagtc acatactctg g                           41

<210> SEQ ID NO 170
<211> LENGTH: 40
<212> TYPE: DNA
<213> ORGANISM: Artificial Sequence
<220> FEATURE:
<221> NAME/KEY: source
<222> LOCATION: 1..40
<223> OTHER INFORMATION: /mol_type="DNA"
        /note="Description of artificial sequence: primer"
        /organism="Artificial Sequence"

<400> SEQUENCE: 170
actagtcgac atgggcatca agatgagtca catactctgg                             40

<210> SEQ ID NO 171
<211> LENGTH: 38
<212> TYPE: DNA
<213> ORGANISM: Artificial Sequence
<220> FEATURE:
<221> NAME/KEY: source
<222> LOCATION: 1..38
<223> OTHER INFORMATION: /mol_type="DNA"
        /note="Description of artificial sequence: primer"
        /organism="Artificial Sequence"

<400> SEQUENCE: 171
actagtcgac tgggcatcag atgagtcaca tactctgg                               38

<210> SEQ ID NO 172
<211> LENGTH: 41
<212> TYPE: DNA
<213> ORGANISM: Artificial Sequence
<220> FEATURE:
<221> NAME/KEY: source
```

```
<222> LOCATION: 1..41
<223> OTHER INFORMATION: /mol_type="DNA"
      /note="Description of artificial sequence: primer"
      /organism="Artificial Sequence"

<400> SEQUENCE: 172
actagtcgac atgggcatca agatgaagtc acagacccag g                         41

<210> SEQ ID NO 173
<211> LENGTH: 41
<212> TYPE: DNA
<213> ORGANISM: Artificial Sequence
<220> FEATURE:
<221> NAME/KEY: source
<222> LOCATION: 1..41
<223> OTHER INFORMATION: /mol_type="DNA"
      /note="Description of artificial sequence: primer"
      /organism="Artificial Sequence"

<400> SEQUENCE: 173
actagtcgac atgggcttca agatgaagtc acattctctg g                         41

<210> SEQ ID NO 174
<211> LENGTH: 41
<212> TYPE: DNA
<213> ORGANISM: Artificial Sequence
<220> FEATURE:
<221> NAME/KEY: source
<222> LOCATION: 1..41
<223> OTHER INFORMATION: /mol_type="DNA"
      /note="Description of artificial sequence: primer"
      /organism="Artificial Sequence"

<400> SEQUENCE: 174
actagtcgac atgggcttca agatgaagtc acatattcag g                         41

<210> SEQ ID NO 175
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 175
actagtcgac atggatggag cttatcatcc tctt                                 34

<210> SEQ ID NO 176
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 176
cccaagcttc cagggaccaa gggataaacg gtgg                                 34

<210> SEQ ID NO 177
<211> LENGTH: 35
<212> TYPE: DNA
<213> ORGANISM: Artificial Sequence
<220> FEATURE:
```

```
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 177
cccaagcttc caggggccag tggataaacg ggtgg                              35

<210> SEQ ID NO 178
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="DNA"
      /note="Description of artificial sequence: primer"
      /organism="Artificial Sequence"

<400> SEQUENCE: 178
actagtcgac atgaggtact cggctcagtt cctggg                             36

<210> SEQ ID NO 179
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="DNA"
      /note="Description of artificial sequence: primer"
      /organism="Artificial Sequence"

<400> SEQUENCE: 179
actagtcgac atgaggtccc cggctcagtt cctggg                             36

<210> SEQ ID NO 180
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="DNA"
      /note="Description of artificial sequence: primer"
      /organism="Artificial Sequence"

<400> SEQUENCE: 180
actagtcgac atgaggacgt cgattcagtt cttggg                             36

<210> SEQ ID NO 181
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 181
gggaattcat ggaatggacc tgggtcatcc tctt                               34

<210> SEQ ID NO 182
<211> LENGTH: 34
<212> TYPE: DNA
<213> ORGANISM: Artificial Sequence
```

```
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 182
gggaattcat ggaatgcagc tgggttatcc tctt                          34

<210> SEQ ID NO 183
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="DNA"
      /note="Description of artificial sequence: primer"
      /organism="Artificial Sequence"

<400> SEQUENCE: 183
gggaattcat gaatggatct gggttattct ctt                           33

<210> SEQ ID NO 184
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 184
cccaagcttc cagggaccag gggataaacg ggtgg                         35

<210> SEQ ID NO 185
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="DNA"
      /note="Description of artificial sequence: primer"
      /organism="Artificial Sequence"

<400> SEQUENCE: 185
cccaagcttc cagggaccaa gggacgggtg g                             31

<210> SEQ ID NO 186
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 186
cccaagcttc cagggaccaa tggataaaca gatgg                         35

<210> SEQ ID NO 187
<211> LENGTH: 35
<212> TYPE: DNA
```

```
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 187
cccaagcttc cagggaccaa gggataaacg ggtgg                          35

<210> SEQ ID NO 188
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="DNA"
      /note="Description of artificial sequence: primer"
      /organism="Artificial Sequence"

<400> SEQUENCE: 188
gggaattcat ggagacacat tcccaggtct tt                             32

<210> SEQ ID NO 189
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="DNA"
      /note="Description of artificial sequence: primer"
      /organism="Artificial Sequence"

<400> SEQUENCE: 189
gggaattcat ggagtcacag tctcaggtct tt                             32

<210> SEQ ID NO 190
<211> LENGTH: 41
<212> TYPE: DNA
<213> ORGANISM: Artificial Sequence
<220> FEATURE:
<221> NAME/KEY: source
<222> LOCATION: 1..41
<223> OTHER INFORMATION: /mol_type="DNA"
      /note="Description of artificial sequence: primer"
      /organism="Artificial Sequence"

<400> SEQUENCE: 190
actagtcgac atgggcttca agatggagtc acattttcag g                   41

<210> SEQ ID NO 191
<211> LENGTH: 41
<212> TYPE: DNA
<213> ORGANISM: Artificial Sequence
<220> FEATURE:
<221> NAME/KEY: source
<222> LOCATION: 1..41
<223> OTHER INFORMATION: /mol_type="DNA"
      /note="Description of artificial sequence: primer"
      /organism="Artificial Sequence"

<400> SEQUENCE: 191
actagtcgac atgggcatca agatgaagtc acatattcag g                   41

<210> SEQ ID NO 192
<211> LENGTH: 41
```

```
-continued

<212> TYPE: DNA
<213> ORGANISM: Artificial Sequence
<220> FEATURE:
<221> NAME/KEY: source
<222> LOCATION: 1..41
<223> OTHER INFORMATION: /mol_type="DNA"
      /note="Description of artificial sequence: primer"
      /organism="Artificial Sequence"

<400> SEQUENCE: 192
actagtcgac atgggcttca agatgaagtc acattctcag g                          41

<210> SEQ ID NO 193
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 193
actagtcgac atgggatgga gcttatcatg ttctt                                 35

<210> SEQ ID NO 194
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 194
actagtcgac atgggatgga gcttatcatg ctctt                                 35

<210> SEQ ID NO 195
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 195
gggaattcat ggaatggacc tgggtttttcc tctt                                 34

<210> SEQ ID NO 196
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 196
gggaattcat ggaatggacc tgggtctttc tctt                                  34

<210> SEQ ID NO 197
```

```
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 197
gggaattcat gaaatggagc tgggttattc tctt                               34

<210> SEQ ID NO 198
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 198
cccaagcttc cagggccaa tggatagacg atgg                                34

<210> SEQ ID NO 199
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 199
cccaagcttc cagggaccaa gggatagacg gatgg                              35

<210> SEQ ID NO 200
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 200
cccaagcttc cagggaccaa gggatagacg atgg                               34

<210> SEQ ID NO 201
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="DNA"
      /note="Description of artificial sequence: primer"
      /organism="Artificial Sequence"

<400> SEQUENCE: 201
actagtcgac atgatgtacc cggctcagtt tctggg                             36
```

-continued

```
<210> SEQ ID NO 202
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="DNA"
      /note="Description of artificial sequence: primer"
      /organism="Artificial Sequence"

<400> SEQUENCE: 202
actagtcgac atgaggactt cgattcagtt cttggg                                 36

<210> SEQ ID NO 203
<211> LENGTH: 39
<212> TYPE: DNA
<213> ORGANISM: Artificial Sequence
<220> FEATURE:
<221> NAME/KEY: source
<222> LOCATION: 1..39
<223> OTHER INFORMATION: /mol_type="DNA"
      /note="Description of artificial sequence: primer"
      /organism="Artificial Sequence"

<400> SEQUENCE: 203
actagtctac atgaagttgc ctgttaggct gttggtgct                              39

<210> SEQ ID NO 204
<211> LENGTH: 39
<212> TYPE: DNA
<213> ORGANISM: Artificial Sequence
<220> FEATURE:
<221> NAME/KEY: source
<222> LOCATION: 1..39
<223> OTHER INFORMATION: /mol_type="DNA"
      /note="Description of artificial sequence: primer"
      /organism="Artificial Sequence"

<400> SEQUENCE: 204
actagtcgac atgaagttgt ctgttaggct gttggtgct                              39

<210> SEQ ID NO 205
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="DNA"
      /note="Description of artificial sequence: primer"
      /organism="Artificial Sequence"

<400> SEQUENCE: 205
atgggatgga gctrtatcat sytctt                                            26

<210> SEQ ID NO 206
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="DNA"
      /note="Description of artificial sequence: primer"
      /organism="Artificial Sequence"

<400> SEQUENCE: 206
atgaagwtgt ggbtraactg grt                                               23
```

```
<210> SEQ ID NO 207
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="DNA"
      /note="Description of artificial sequence: primer"
      /organism="Artificial Sequence"
<220> FEATURE:
<221> NAME/KEY: variation
<222> LOCATION: 15
<223> OTHER INFORMATION: /replace="n=i"

<400> SEQUENCE: 207
atggratgga sckknrtctt tmtct                                          25

<210> SEQ ID NO 208
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="DNA"
      /note="Description of artificial sequence: primer"
      /organism="Artificial Sequence"
<220> FEATURE:
<221> NAME/KEY: variation
<222> LOCATION: 21
<223> OTHER INFORMATION: /replace="n=i"

<400> SEQUENCE: 208
ccagggrcca rkggatarac ngrtgg                                         26

<210> SEQ ID NO 209
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="DNA"
      /note="Description of artificial sequence: primer"
      /organism="Artificial Sequence"

<400> SEQUENCE: 209
atggagacag acacactcct gctat                                          25

<210> SEQ ID NO 210
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="DNA"
      /note="Description of artificial sequence: primer"
      /organism="Artificial Sequence"

<400> SEQUENCE: 210
atggagwcag acacactsct gytatgggt                                      29

<210> SEQ ID NO 211
<211> LENGTH: 29
<212> TYPE: DNA
<213> ORGANISM: Artificial Sequence
<220> FEATURE:
<221> NAME/KEY: source
```

-continued

```
<222> LOCATION: 1..29
<223> OTHER INFORMATION: /mol_type="DNA"
      /note="Description of artificial sequence: primer"
      /organism="Artificial Sequence"

<400> SEQUENCE: 211
atgaagttgc ctgttaggct gttggtgct                              29

<210> SEQ ID NO 212
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="DNA"
      /note="Description of artificial sequence: primer"
      /organism="Artificial Sequence"

<400> SEQUENCE: 212
atggatttwc argtgcagat twtcagctt                              29

<210> SEQ ID NO 213
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="DNA"
      /note="Description of artificial sequence: primer"
      /organism="Artificial Sequence"

<400> SEQUENCE: 213
atggtyctya tvtccttgct gttctgg                                27

<210> SEQ ID NO 214
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="DNA"
      /note="Description of artificial sequence: primer"
      /organism="Artificial Sequence"

<400> SEQUENCE: 214
atggtyctya tvttrctgct gctatgg                                27

<210> SEQ ID NO 215
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="DNA"
      /note="Description of artificial sequence: primer"
      /organism="Artificial Sequence"

<400> SEQUENCE: 215
actggatggt gggaagatgg a                                      21

<210> SEQ ID NO 216
<211> LENGTH: 26
<212> TYPE: DNA
<213> ORGANISM: Artificial Sequence
<220> FEATURE:
```

```
<221> NAME/KEY: source
<222> LOCATION: 1..26
<223> OTHER INFORMATION: /mol_type="DNA"
      /note="Description of artificial sequence: primer"
      /organism="Artificial Sequence"

<400> SEQUENCE: 216
atgaaatgca gctggrtyat sttctt                                    26

<210> SEQ ID NO 217
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="DNA"
      /note="Description of artificial sequence: primer"
      /organism="Artificial Sequence"

<400> SEQUENCE: 217
atggrcagrc ttacwtyytc attcct                                    26

<210> SEQ ID NO 218
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="DNA"
      /note="Description of artificial sequence: primer"
      /organism="Artificial Sequence"

<400> SEQUENCE: 218
atgatggtgt taagtcttct gtacct                                    26

<210> SEQ ID NO 219
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="DNA"
      /note="Description of artificial sequence: primer"
      /organism="Artificial Sequence"

<400> SEQUENCE: 219
atgragwcac akwcycaggt cttt                                      24

<210> SEQ ID NO 220
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="DNA"
      /note="Description of artificial sequence: primer"
      /organism="Artificial Sequence"
<220> FEATURE:
<221> NAME/KEY: variation
<222> LOCATION: 27
<223> OTHER INFORMATION: /replace="n=i"

<400> SEQUENCE: 220
atgaggrccc ctgctcagwt tyttggnwtc tt                             32
```

```
<210> SEQ ID NO 221
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="DNA"
      /note="Description of artificial sequence: primer"
      /organism="Artificial Sequence"

<400> SEQUENCE: 221
atgggcwtca agatgragtc acakwyycwg g                              31
```